US011185249B2

(12) United States Patent
Schlemper et al.

(10) Patent No.: US 11,185,249 B2
(45) Date of Patent: Nov. 30, 2021

(54) SELF ENSEMBLING TECHNIQUES FOR GENERATING MAGNETIC RESONANCE IMAGES FROM SPATIAL FREQUENCY DATA

(71) Applicant: Hyperfine, Inc., Guilford, CT (US)

(72) Inventors: Jo Schlemper, Long Island City, NY (US); Seyed Sadegh Moshen Salehi, Bloomfield, NJ (US); Michal Sofka, Princeton, NJ (US)

(73) Assignee: Hyperfine, Inc., Guilford, CT (US)

( * ) Notice: Subject to any disclaimer, the term of this patent is extended or adjusted under 35 U.S.C. 154(b) by 0 days.

(21) Appl. No.: 16/817,454

(22) Filed: Mar. 12, 2020

(65) Prior Publication Data

US 2020/0294229 A1 Sep. 17, 2020

Related U.S. Application Data

(60) Provisional application No. 62/926,890, filed on Oct. 28, 2019, provisional application No. 62/820,119, (Continued)

(51) Int. Cl.
*A61B 5/055* (2006.01)
*G01R 33/561* (2006.01)
(Continued)

(52) U.S. Cl.
CPC ............ *A61B 5/055* (2013.01); *G01R 33/36* (2013.01); *G01R 33/383* (2013.01);
(Continued)

(58) Field of Classification Search
CPC ....... A61B 5/055; A61B 5/0033; G06T 7/262; G06T 7/38; G06T 2207/20182;
(Continued)

(56) References Cited

U.S. PATENT DOCUMENTS 7,019,524 B2 * 3/2006 Gurr ................. G01R 33/56375
324/314
7,202,663 B2 * 4/2007 Huang ............... G01R 33/5611
324/307
(Continued)

FOREIGN PATENT DOCUMENTS

EP 2194392 A1 6/2010
EP 3467766 A1 4/2019
(Continued)

OTHER PUBLICATIONS

U.S. Appl. No. 16/524,598, filed Jul. 29, 2019, Schlemper et al.
(Continued)

*Primary Examiner* — Manav Seth
(74) *Attorney, Agent, or Firm* — Wolf, Greenfield & Sacks, P.C.

(57) ABSTRACT

Techniques for generating magnetic resonance (MR) images of a subject from MR data obtained by a magnetic resonance imaging (MRI) system, the techniques including: obtaining input MR data obtained by imaging the subject using the MRI system; generating a plurality of transformed input MR data instances by applying a respective first plurality of transformations to the input MR data; generating a plurality of MR images from the plurality of transformed input MR data instances and the input MR data using a non-linear MR image reconstruction technique; generating an ensembled MR image from the plurality of MR images at least in part by: applying a second plurality of transformations to the plurality of MR images to obtain a plurality of transformed MR images; and combining the plurality of transformed MR images to obtain the ensembled MR image; and outputting the ensembled MR image.

20 Claims, 45 Drawing Sheets

US 11,185,249 B2
Page 2

Related U.S. Application Data filed on Mar. 18, 2019, provisional application No. 62/818,148, filed on Mar. 14, 2019.

(51) Int. Cl.

| | |
|---|---|
| *G06N 3/04* | (2006.01) |
| *G06N 3/08* | (2006.01) |
| *G06T 7/38* | (2017.01) |
| *G01R 33/383* | (2006.01) |
| *G01R 33/44* | (2006.01) |
| *G01R 33/56* | (2006.01) |
| *G06T 3/60* | (2006.01) |
| *G06T 11/00* | (2006.01) |
| *G16H 30/40* | (2018.01) |
| *G01R 33/36* | (2006.01) |
| *G06T 7/262* | (2017.01) |
| *G06K 9/62* | (2006.01) |
| *G06K 9/74* | (2006.01) |
| *G06T 7/00* | (2017.01) |

(52) U.S. Cl.
CPC ....... *G01R 33/445* (2013.01); *G01R 33/5608* (2013.01); *G01R 33/5611* (2013.01); *G06K 9/6203* (2013.01); *G06K 9/6245* (2013.01); *G06K 9/741* (2013.01); *G06K 9/748* (2013.01); *G06N 3/0454* (2013.01); *G06N 3/08* (2013.01); *G06N 3/082* (2013.01); *G06T 3/60* (2013.01); *G06T 7/0012* (2013.01); *G06T 7/262* (2017.01); *G06T 7/38* (2017.01); *G06T 11/006* (2013.01); *G06T 11/008* (2013.01); *G16H 30/40* (2018.01); *G06T 2207/10088* (2013.01); *G06T 2207/20056* (2013.01); *G06T 2207/20081* (2013.01); *G06T 2207/20084* (2013.01); *G06T 2207/20182* (2013.01); *G06T 2207/20216* (2013.01); *G06T 2207/20224* (2013.01); *G06T 2207/30016* (2013.01); *G06T 2210/41* (2013.01)

(58) Field of Classification Search
CPC . G06T 2207/20216; G06T 2207/20224; G06T 2207/30016; G06T 2210/41; G06T 5/50; G06T 3/60; G06T 7/0012; G06T 11/006; G06T 11/008; G06T 2207/10088; G06T 2207/20056; G06T 2207/20081; G06T 2207/20084; G16H 30/40; G01R 33/36; G01R 33/383; G01R 33/445; G01R 33/5608; G01R 33/5611; G06K 9/6203; G06K 9/6245; G06K 9/741; G06K 9/748; G06N 3/0454; G06N 3/08; G06N 3/082; G01S 15/8995

See application file for complete search history.

(56) References Cited

U.S. PATENT DOCUMENTS

| | | | | |
|---|---|---|---|---|
| 7,602,183 B2* | 10/2009 | Lustig | ................ | G01R 33/561 324/307 |
| 7,688,068 B2* | 3/2010 | Beatty | ................ | A61B 5/055 324/307 |
| 7,881,511 B2* | 2/2011 | Ye | ................ | G01R 33/561 382/128 |
| 8,170,315 B2* | 5/2012 | Mistretta | ................ | G06T 11/006 382/131 |
| 8,354,844 B2* | 1/2013 | Zaitsev | ................ | G01R 33/5611 324/307 |
| 8,384,383 B2* | 2/2013 | Frahm | ................ | G01R 33/5611 324/309 |
| 8,473,028 B2 | 6/2013 | Mitsouras et al. | | |
| 8,692,549 B2* | 4/2014 | Grady | ................ | G01R 33/5611 324/309 |
| 8,781,197 B2* | 7/2014 | Wang | ................ | G01R 33/563 382/131 |
| 9,224,210 B2* | 12/2015 | Epstein | ................ | G06T 7/0012 |
| 9,256,966 B2* | 2/2016 | Jacobs | ................ | G06T 7/0012 |
| 9,269,127 B2* | 2/2016 | Ding | ................ | G06T 5/002 |
| 9,285,449 B2* | 3/2016 | Liu | ................ | G01R 33/443 |
| 9,396,562 B2* | 7/2016 | Lefebvre | ................ | G01R 33/5611 |
| 9,541,616 B2 | 1/2017 | Rothberg et al. | | |
| 9,547,057 B2 | 1/2017 | Rearick et al. | | |
| 9,625,543 B2 | 4/2017 | Rearick et al. | | |
| 9,625,544 B2 | 4/2017 | Poole et al. | | |
| 9,638,773 B2 | 5/2017 | Poole et al. | | |
| 9,645,210 B2 | 5/2017 | McNulty et al. | | |
| 9,770,223 B2* | 9/2017 | Samsonov | ................ | G01R 33/5611 |
| 9,797,971 B2 | 10/2017 | Rearick et al. | | |
| 9,817,093 B2 | 11/2017 | Rothberg et al. | | |
| 9,921,285 B2* | 3/2018 | Otazo | ................ | A61B 5/7207 |
| 9,964,615 B2* | 5/2018 | Fuderer | ................ | G01R 33/561 |
| 10,026,186 B2* | 7/2018 | Gerganov | ................ | G06T 7/30 |
| 10,073,160 B2* | 9/2018 | Boernert | ................ | G01R 33/56509 |
| 10,139,464 B2 | 11/2018 | Rearick et al. | | |
| 10,145,913 B2 | 12/2018 | Hugon et al. | | |
| 10,145,922 B2 | 12/2018 | Rothberg et al. | | |
| 10,222,434 B2 | 3/2019 | Poole et al. | | |
| 10,222,435 B2 | 3/2019 | Mileski et al. | | |
| 10,241,177 B2 | 3/2019 | Poole et al. | | |
| 10,274,561 B2 | 4/2019 | Poole et al. | | |
| 10,274,563 B2* | 4/2019 | Choi | ................ | G01R 33/4818 |
| 10,281,540 B2 | 5/2019 | Mileski et al. | | |
| 10,281,541 B2 | 5/2019 | Poole et al. | | |
| 10,281,549 B2* | 5/2019 | Takeshima | ................ | G01R 33/5611 |
| 10,295,628 B2 | 5/2019 | Mileski et al. | | |
| 10,310,037 B2 | 6/2019 | McNulty et al. | | |
| 10,324,147 B2 | 6/2019 | McNulty et al. | | |
| 10,330,755 B2 | 6/2019 | Poole et al. | | |
| 10,353,030 B2 | 7/2019 | Poole et al. | | |
| 10,371,773 B2 | 8/2019 | Poole et al. | | |
| 10,379,186 B2 | 8/2019 | Rothberg et al. | | |
| 10,416,264 B2 | 9/2019 | Sofka et al. | | |
| 10,444,310 B2 | 10/2019 | Poole et al. | | |
| 10,466,327 B2 | 11/2019 | Rothberg et al. | | |
| 10,488,482 B2 | 11/2019 | Rearick et al. | | |
| 10,495,712 B2 | 12/2019 | Rothberg et al. | | |
| 10,520,566 B2 | 12/2019 | Poole et al. | | |
| 10,527,692 B2 | 1/2020 | McNulty et al. | | |
| 10,534,058 B2 | 1/2020 | Sofka et al. | | |
| 10,534,059 B2* | 1/2020 | Rich | ................ | G01R 33/5608 |
| 10,539,637 B2 | 1/2020 | Poole et al. | | |
| 10,545,207 B2 | 1/2020 | Poole et al. | | |
| 10,551,452 B2 | 2/2020 | Rearick et al. | | |
| 10,564,239 B2 | 2/2020 | Poole et al. | | |
| 10,588,587 B2* | 3/2020 | Samsonov | ................ | G01R 33/5611 |
| 10,591,561 B2 | 3/2020 | Sacolick et al. | | |
| 10,591,567 B2* | 3/2020 | Saito | ................ | G01R 33/56316 |
| 10,605,878 B2* | 3/2020 | Otazo | ................ | G01R 33/5611 |
| 10,635,943 B1* | 4/2020 | Lebel | ................ | G06T 5/50 |
| 10,650,532 B2* | 5/2020 | Gerganov | ................ | G06T 7/20 |
| 10,663,551 B2* | 5/2020 | Arunachalam | ....... | G01R 33/561 |
| 10,667,691 B2* | 6/2020 | Lee | ................ | G01R 33/4826 |
| 10,709,387 B2 | 7/2020 | Poole et al. | | |
| 10,748,309 B2* | 8/2020 | Seevinck | ........... | G01R 33/5608 |
| 10,803,631 B2* | 10/2020 | Li | ................ | G01R 33/4818 |
| 10,831,997 B2* | 11/2020 | Lin | ................ | G06N 3/0454 |
| 10,950,014 B2* | 3/2021 | Wheaton | ................ | G06T 11/008 |
| 2016/0069968 A1 | 3/2016 | Rothberg et al. | | |
| 2016/0069970 A1 | 3/2016 | Rearick et al. | | |
| 2016/0069971 A1 | 3/2016 | McNulty et al. | | |
| 2016/0069972 A1 | 3/2016 | Poole et al. | | |
| 2016/0069975 A1 | 3/2016 | Rothberg et al. | | |
| 2016/0128592 A1 | 5/2016 | Rosen et al. | | |
| 2016/0131727 A1 | 5/2016 | Sacolick et al. | | |
| 2016/0169992 A1 | 6/2016 | Rothberg et al. | | |
| 2016/0169993 A1 | 6/2016 | Rearick et al. | | |
| 2016/0223631 A1 | 8/2016 | Poole et al. | | |
| 2016/0231399 A1 | 8/2016 | Rothberg et al. | | |
| 2016/0231402 A1 | 8/2016 | Rothberg et al. | | |
| 2016/0231403 A1 | 8/2016 | Rothberg et al. | | |

(56) References Cited

U.S. PATENT DOCUMENTS

| | | |
|---|---|---|
| 2016/0231404 A1 | 8/2016 | Rothberg et al. |
| 2016/0299203 A1 | 10/2016 | Mileski et al. |
| 2016/0334479 A1 | 11/2016 | Poole et al. |
| 2017/0102443 A1 | 4/2017 | Rearick et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2018/0012354 A1 | 1/2018 | Fisher |
| 2018/0024208 A1 | 1/2018 | Rothberg et al. |
| 2018/0038931 A1 | 2/2018 | Rearick et al. |
| 2018/0088193 A1 | 3/2018 | Rearick et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0128989 A1 | 5/2019 | Braun et al. |
| 2019/0162806 A1 | 5/2019 | Poole et al. |
| 2019/0172230 A1 | 6/2019 | Mailhe et al. |
| 2019/0178962 A1 | 6/2019 | Poole et al. |
| 2019/0178963 A1 | 6/2019 | Poole et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0311267 A1 | 10/2019 | Qin et al. |
| 2019/0324098 A1 | 10/2019 | McNulty et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |
| 2020/0011952 A1 | 1/2020 | Rothberg et al. |
| 2020/0018806 A1 | 1/2020 | Rothberg et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0025851 A1 | 1/2020 | Rearick et al. |
| 2020/0033431 A1 | 1/2020 | Schlemper et al. |
| 2020/0034998 A1 | 1/2020 | Schlemper et al. |
| 2020/0041588 A1 | 2/2020 | O'Halloran et al. |
| 2020/0045112 A1 | 2/2020 | Sacolick et al. |
| 2020/0058106 A1 | 2/2020 | Lazarus et al. |
| 2020/0200844 A1 | 6/2020 | Boskamp et al. |
| 2020/0209334 A1 | 7/2020 | O'Halloran et al. |
| 2020/0289019 A1 | 9/2020 | Schlemper et al. |
| 2020/0289022 A1 | 9/2020 | Coumans et al. |
| 2020/0294282 A1 | 9/2020 | Schlemper et al. |
| 2020/0294287 A1* | 9/2020 | Schlemper .......... G06T 7/0012 |
| 2020/0337587 A1 | 10/2020 | Sacolick et al. |
| 2020/0355765 A1 | 11/2020 | Chen et al. |

FOREIGN PATENT DOCUMENTS

| | | |
|---|---|---|
| WO | WO 2018/045274 A1 | 3/2018 |
| WO | WO 2018/187005 A1 | 10/2018 |

OTHER PUBLICATIONS

U.S. Appl. No. 16/524,638, filed Jul. 29, 2019, Schlemper et al.
U.S. Appl. No. 16/541,511, filed Aug. 15, 2019, Lazarus et al.
U.S. Appl. No. 16/817,269, filed Mar. 12, 2020, Schlemper et al.
U.S. Appl. No. 16/817,370, filed Mar. 12, 2020, Schlemper et al.
U.S. Appl. No. 16/817,402, filed Mar. 12, 2020, Schlemper et al.
PCT/US2019/043927, Nov. 22, 2019, Invitation to Pay Additional Fees.
PCT/US2019/043927, Jan. 28, 2020, International Search Report and Written Opinion.
PCT/US2019/046649, Nov. 12, 2019, International Search Report and Written Opinion.
International Search Report and Written Opinion for International Application No. PCT/US2020/022306 dated Oct. 2, 2020.
International Search Report and Written Opinion for Application No. PCT/US2019/046649, dated Nov. 12, 2019.
International Search Report and Written Opinion for Application No. PCT/US2019/043927, dated Jan. 28, 2020.
Invitation to Pay Additional Fees for Application No. PCT/US2019/043927, mailed Nov. 22, 2019
Caballero et al., Application-driven MRI: Joint reconstruction and segmentation from undersampled MRI data. International Conference on Medical Image Computing and Computer-Assisted Intervention Sep. 14, 2014:106-113.
Caballero et al., Dictionary learning and time sparsity for dynamic MR data reconstruction. IEEE transactions on medical imaging. Jan. 17, 2014;33(4):979-94.
Cordero-Grande et al., Three-dimensional motion corrected sensitivity encoding reconstruction for multi-shot multi-slice MRI: application to neonatal brain imaging. Magnetic resonance in medicine. Mar. 2018;79(3):1365-76.
Delattre et al., Spiral demystified. Magnetic resonance imaging. Jul. 1, 2010;28(6):862-81.
Eo et al., KIKI-net: cross-domain convolutional neural networks for reconstructing undersampled magnetic resonance images. Magnetic resonance in medicine. Nov. 2018;80(5):2188-201.
Eo et al., Supporting Information—KIKI-net: cross-domain convolutional neural networks for reconstructing undersampled magnetic resonance images. Magnetic resonance in medicine. Nov. 2018:14 pages.
Fessler et al., Nonuniform fast Fourier transforms using min-max interpolation. IEEE transactions on signal processing. Jan. 22, 2003;51(2):560-74.
Fessler, Model-based image reconstruction for MRI. IEEE Signal Processing Magazine. Jul. 1, 2010;27(4):81-9.
Fessler, on NUFFT-based gridding for non-Cartesian MRI. Journal of Magnetic Resonance. Oct. 1, 2007;188(2):191-5.
Forbes et al., Propeller MRI: clinical testing of a novel technique for quantification and compensation of head motion. Journal of Magnetic Resonance Imaging: An Official Journal of the International Society for Magnetic Resonance in Medicine. Sep. 2001;14(3):215-22.
Gal et al., Dropout as a Bayesian approximation: Representing model uncertainty in deep learning. International conference on machine learning. Jun. 11, 2016:1050-1059.
Greengard et al., Accelerating the nonuniform fast Fourier transform. SIAM review. 2004;46(3):443-54.
Griswold et al., Generalized autocalibrating partially parallel acquisitions (GRAPPA). Magnetic Resonance in Medicine: An Official Journal of the International Society for Magnetic Resonance in Medicine. Jun. 2002;47(6):1202-10.

(56) References Cited

OTHER PUBLICATIONS

Hammernik et al., Learning a variational network for reconstruction of accelerated MRI data. Magnetic resonance in medicine. Jun. 2018;79(6):3055-71.
Han et al., Deep learning with domain adaptation for accelerated projection-reconstruction MR. Magnetic resonance in medicine. Sep. 2018;80(3):1189-205.
Han et al., k-space deep learning for accelerated MRI. arXiv preprint arXiv:1805.03779. May 10, 2018;1;11 pages.
He et al., Deep residual learning for image recognition. In Proceedings of the IEEE conference on computer vision and pattern recognition 2016:770-778.
Hu et al., Squeeze-and-excitation networks. Proceedings of the IEEE conference on computer vision and pattern recognition 2018:7132-7141.
Huang et al.,. Densely connected convolutional networks. Proceedings of the IEEE conference on computer vision and pattern recognition 2017:4700-4708.
Jaderberg et al., Spatial transformer networks. Advances in neural information processing systems. 2015:1-9.
Jin et al., A general framework for compressed sensing and parallel MRI using annihilating filter based low-rank Hankel matrix. arXiv preprint arXiv:1504.00532. Dec. 30, 2015;4:32 pages.
Khalel, Edafa. GitHub. Nov. 26, 2018:3 pages. https://github.com/andrewekhalel/edafa/blob/master/README.md [last accessed Mar. 25, 2020].
Kingma et al., Adam: A method for stochastic optimization. arXiv preprint arXiv:1412.6980. Dec. 22, 2014;1:9 pages.
Knoll et al., Adapted random sampling patterns for accelerated MRI. Magnetic resonance materials in physics, biology and medicine. Feb. 1, 2011;24(1):43-50.
Knoll et al., Second order total generalized variation (TGV) for MRI. Magnetic resonance in medicine. Feb. 2011;65(2):480-91.
Lazarus et al., Sparkling: variable-density k-space filling curves for accelerated T2*-weighted MRI. Magnetic resonance in medicine. Jun. 2019;81(6):3643-61.
Lee et al., 18: An Overview of Deep Learning building blocks, Lecturer: Maruan Al-Shedivat Scribes. XP055641812. May 1, 2017:8 pages.
Lee et al., Acceleration of MR parameter mapping using annihilating filter-based low rank Hankel matrix (ALOHA). Magnetic resonance in medicine. Dec. 2016;76(6):1848-64.
Lee et al., Deep residual learning for accelerated MRI using magnitude and phase networks. IEEE Transactions on Biomedical Engineering. Apr. 2, 2018;65(9):1985-95.
Lundervold et al., An overview of deep learning in medical imaging focusing on MRI. Zeitschrift für Medizinische Physik. May 1, 2019;29(2):102-27.
Lustig et al., Compressed sensing MRI. IEEE signal processing magazine. Mar. 21, 2008;25(2):72-82.
Ma et al., Learning traffic as images: a deep convolutional neural network for large-scale transportation network speed prediction. Sensors. 2017;17(4):818.
Mardani et al., Deep generative adversarial networks for compressed sensing automates MRI. arXiv preprint arXiv:1706.00051. May 31, 2017;1:12 pages.
Pauly, Gridding & NUFFT for Non-Cartesian Image Reconstruction. Proceedings of the International Society for Magnetic Resonance in Medicine. 2013;21:3 pages.
Pawar et al., Moconet: Motion correction in 3D MPRAGE images using a convolutional neural network approach. arXiv preprint arXiv:1807.10831. Jul. 29, 2018: 20 pages.
Perone et al., Unsupervised domain adaptation for medical imaging segmentation with self-ensembling. NeuroImage. Jul. 1, 2019;194:1-11.
Pipe, Motion correction with Propeller MRI: application to head motion and free-breathing cardiac imaging. Magnetic Resonance in Medicine: An Official Journal of the International Society for Magnetic Resonance in Medicine. Nov. 1999;42(5):963-9.
Pluim et al., Mutual-information-based registration of medical images: a survey. IEEE transactions on medical imaging. Jul. 28, 2003;22(8):986-1004.
Pruessmann et al., SENSE: sensitivity encoding for fast MRI. Magnetic Resonance in Medicine: An Official Journal of the International Society for Magnetic Resonance in Medicine. Nov. 1999;42(5):952-62.
Qin et al., Convolutional recurrent neural networks for dynamic MR image reconstruction. arXiv preprint arXiv:1712.01751. Dec. 5, 2017;1:9 pages.
Salehi et al., Real-time deep registration with geodesic loss for Image-to-Template Rigid Registration. arXiv preprint arXiv:1803.05982. Aug. 18, 2018;4:12 pages.
Schlemper et al., A deep cascade of convolutional neural networks for dynamic MR image reconstruction. IEEE transactions on Medical Imaging. Feb. 2013;37(2):491-503.
Schlemper et al., Cardiac MR segmentation from undersampled k-space using deep latent representation learning. International Conference on Medical Image Computing and Computer-Assisted Intervention Sep. 16, 2018:259-267.
Schlemper et al., Nonuniform Variational Network: Deep Learning for Accelerated Nonuniform MR Image Reconstruction. In International Conference on Medical Image Computing and Computer-Assisted Intervention Oct. 13, 2019:57-64.
Sen et al., Compressive image super-resolution. IEEE 2009 Conference Record of the Forty-Third Asilomar Conference on Signals, Systems and Computers. Nov. 1, 2009:1235-1242.
Shi et al., Is the deconvolution layer the same as a convolutional layer? arXiv preprint arXiv:1609.07009. Sep. 22, 2016:8 pages.
Souza et al., A hybrid frequency-domain/image-domain deep network for magnetic resonance image reconstruction. arXiv preprint arXiv:1810.12473. Oct. 30, 2018:1-8.
Tajbakhsh et al., Convolutional neural networks for medical image analysis: Full training or fine tuning? An accepted version of N. arXiv preprint arXiv:1706.0712. Jun. 2, 2017:1-17.
Tamada et al., Method for motion artifact reduction using a convolutional neural network for dynamic contrast enhanced MRI of the liver. arXiv preprint arXiv:1807.06956. Jul. 18, 2018:1-12.
Usman et al., Motion corrected compressed sensing for free-breathing dynamic cardiac MRI. Magnetic resonance in medicine. Aug. 2013;70(2):504-16.
Walsh et al., Adaptive reconstruction of phased array MR imagery. Magnetic Resonance in Medicine: An Official Journal of the International Society for Magnetic Resonance in Medicine. May 2000;43(5):682-90.
Wang et al., Dimension: Dynamic mr imaging with both k-space and spatial prior knowledge obtained via multi-supervised network training. MMR in Biomedicine. arXiv preprint arXiv:1810.00302. Nov. 6, 2018;4:1-13.
Wang et al., Image quality assessment: from error visibility to structural similarity. IEEE transactions on image processing. Apr. 13, 2004;13(4):600-12.
Yang et al., DAGAN: Deep de-aliasing generative adversarial networks for fast compressed sensing MRI reconstruction. IEEE transactions on medical imaging. Jun. 2018;37(6):1310-21.
Zhang et al., Coil compression for accelerated imaging with Cartesian sampling. Magnetic resonance in medicine. Feb. 2013;69(2):571-82.
Zhu et al., HENet: A Highly Efficient Convolutional Neural Networks Optimized for Accuracy, Speed and Storage. arXiv preprint arXiv:1803.02742. Mar. 7, 2018:12 pages.
Zhu et al., Image reconstruction by domain-transform manifold learning. Nature. Mar. 2018;555(7697):487.
Invitation to Pay Additional Fees for Application No. PCT/US2020/022306, mailed Jul. 3, 2020.
Akcakaya et al., Utility of respiratory-navigator-rejected k-space lines for improved signal-to-noise ratio in three-dimensional cardiac MR. Magnetic resonance in medicine. Nov. 2013;70(5): 1332-9.
Campbell-Washburn et al., Using the robust principal component analysis algorithm to remove RF spike artifacts from MR images Magnetic resonance in medicine. Jun. 2016;75(6):2517-25.

(56) References Cited

OTHER PUBLICATIONS

Graham et al., A supervised learning approach for diffusion MRI quality control with minimal. training data. NeuroImage. Sep. 1, 2018;178:668-76.

Lustig et al., SPIRiT: iterative self-consistent parallel imaging reconstruction from arbitrary k-space. Magnetic resonance in medicine. Aug. 2010;64(2):457-71.

Oksuz et al., Detection and correction of cardiac MRI motion artefacts during reconstruction from k-space. arXiv preprint arXiv:1906.05695. Jun. 12, 2019;1:1-8.

\* cited by examiner

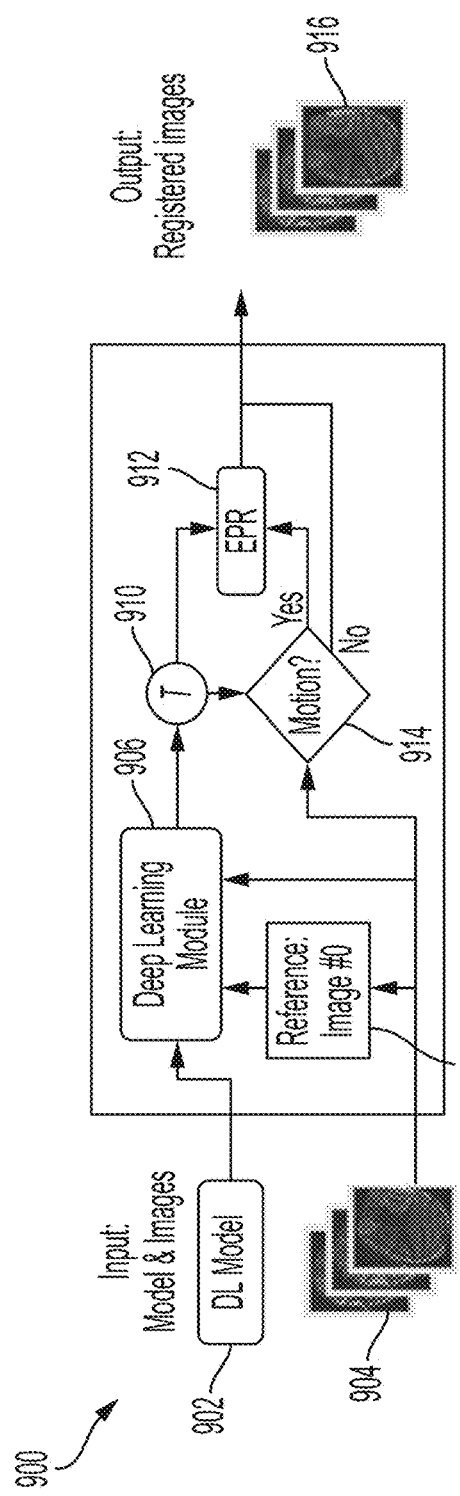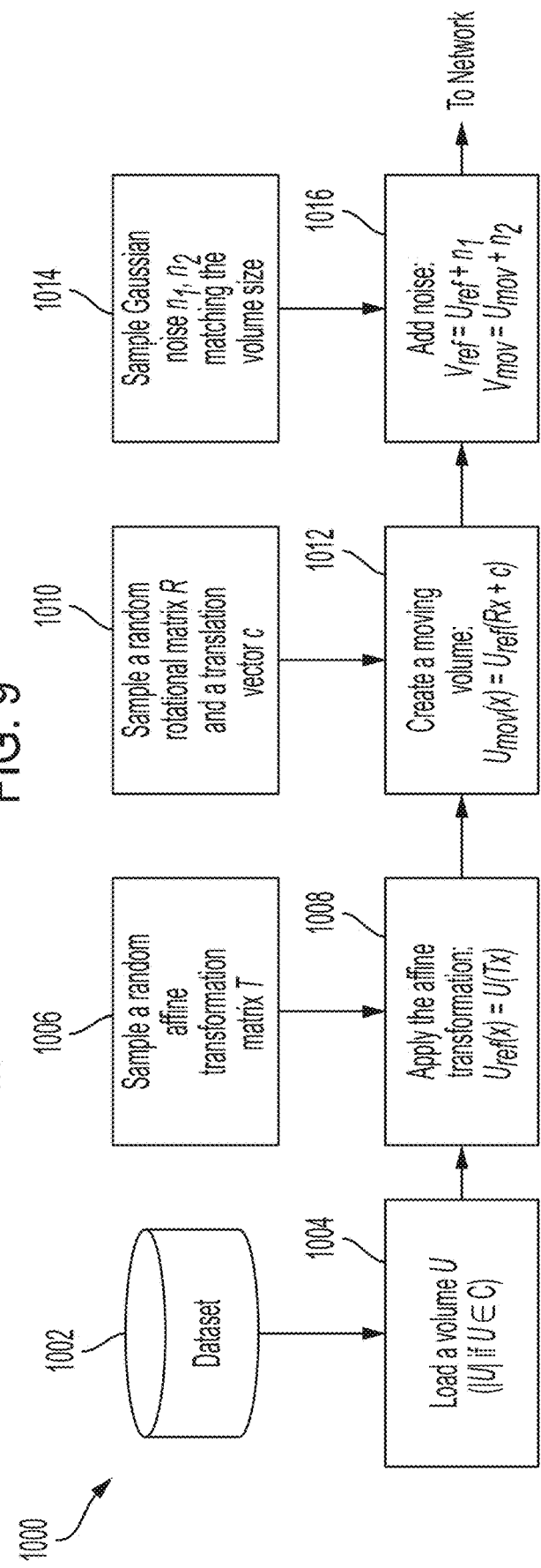
FIG. 9
FIG. 10

SELF ENSEMBLING TECHNIQUES FOR GENERATING MAGNETIC RESONANCE IMAGES FROM SPATIAL FREQUENCY DATA

CROSS-REFERENCE TO RELATED APPLICATIONS

This application claims priority under 35 U.S.C. § 119(e) to U.S. Provisional Application Ser. No. 62/818,148, filed Mar. 14, 2019, and titled "DEEP LEARNING TECHNIQUES FOR MOTION COMPENSATION IN MAGNETIC RESONANCE IMAGING," U.S. Provisional Application Ser. No. 62/820,119, filed Mar. 18, 2019, and titled "END-TO-END LEARNABLE MR IMAGE RECONSTRUCTION", and U.S. Provisional Application Ser. No. 62/926,890, filed Oct. 28, 2019, and titled "SELF ENSEMBLING TECHNIQUES FOR DEEP LEARNING BASED MRI RECONSTRUCTION", each of which is incorporated by reference in its entirety herein.

FIELD

The present disclosure relates generally to generating magnetic resonance (MR) images from input MR spatial frequency data and, more specifically, to machine learning (e.g., deep learning) techniques for processing input MR spatial frequency data to produce MR images.

BACKGROUND

Magnetic resonance imaging (MRI) provides an important imaging modality for numerous applications and is widely utilized in clinical and research settings to produce images of the inside of the human body. MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to its ability to produce non-invasive images having relatively high resolution and contrast without the safety concerns of other modalities (e.g., without needing to expose the subject to ionizing radiation, such as x-rays, or introducing radioactive material into the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring.

SUMMARY

Some embodiments provide for a method for generating magnetic resonance (MR) images of a subject from MR data obtained by a magnetic resonance imaging (MRI) system. The method comprises: obtaining input MR spatial frequency data obtained by imaging the subject using the MRI system; generating an MR image of the subject from the input MR spatial frequency data using a neural network model comprising: a pre-reconstruction neural network configured to process the input MR spatial frequency data; a reconstruction neural network configured to generate at least one initial image of the subject from output of the pre-reconstruction neural network; and a post-reconstruction neural network configured to generate the MR image of the subject from the at least one initial image of the subject.

Some embodiments provide for a magnetic resonance imaging (MRI) system, comprising: a magnetics system having a plurality of magnetics components to produce magnetic fields for performing MRI; and at least one processor configured to perform: obtaining input MR spatial frequency data obtained by imaging the subject using the MRI system; generating an MR image of the subject from the input MR spatial frequency data using a neural network model comprising: a pre-reconstruction neural network configured to process the input MR spatial frequency data; a reconstruction neural network configured to generate at least one initial image of the subject from output of the pre-reconstruction neural network; and a post-reconstruction neural network configured to generate the MR image of the subject from the at least one initial image of the subject.

Some embodiments provide for a system comprising at least one processor configured to perform: obtaining input MR spatial frequency data obtained by imaging the subject using the MRI system; generating an MR image of the subject from the input MR spatial frequency data using a neural network model comprising: a pre-reconstruction neural network configured to process the input MR spatial frequency data; a reconstruction neural network configured to generate at least one initial image of the subject from output of the pre-reconstruction neural network; and a post-reconstruction neural network configured to generate the MR image of the subject from the at least one initial image of the subject.

Some embodiments provide for at least one non-transitory computer readable storage medium storing processor-executable instructions that, when executed by at least one processor, cause the at least one processor to perform a method for generating magnetic resonance (MR) images of a subject from MR data obtained by a magnetic resonance imaging (MRI) system. The method comprises: obtaining input MR spatial frequency data obtained by imaging the subject using the MRI system; generating an MR image of the subject from the input MR spatial frequency data using a neural network model comprising: a pre-reconstruction neural network configured to process the input MR spatial frequency data; a reconstruction neural network configured to generate at least one initial image of the subject from output of the pre-reconstruction neural network; and a post-reconstruction neural network configured to generate the MR image of the subject from the at least one initial image of the subject.

Some embodiments provide a method for generating magnetic resonance (MR) images of a subject from MR data obtained by a magnetic resonance imaging (MRI) system. The method comprising: obtaining first input MR data obtained by imaging the subject using the MRI system; obtaining second input MR data obtained by imaging the subject using the MRI system; generating a first set of one or more MR images from the first input MR data; generating a second set of one or more MR images from the second input MR data; aligning the first set of MR images and the second set of MR images using a neural network model to obtain aligned first and second sets of MR images, the neural network model comprising a first neural network and a second neural network, the aligning comprising: estimating, using the first neural network, a first transformation between the first set of MR images and the second set of MR images; generating a first updated set of MR images from the second set of MR images using the first transformation; estimating, using the second neural network, a second transformation between the first set of MR images and the first updated set of MR images; and aligning the first set of MR images and the second set of MR images at least in part by using the first transformation and the second transformation; combining the aligned first and second sets of MR images to obtain a combined set of one or more MR images; and outputting the combined set of one or more MR images.

Some embodiments at least one non-transitory computer-readable storage medium storing processor-executable instructions that, when executed by at least one processor, cause the at least one processor to perform a method for generating magnetic resonance (MR) images of a subject from MR data obtained by a magnetic resonance imaging (MRI) system. The method comprises: obtaining first input MR data obtained by imaging the subject using the MRI system; obtaining second input MR data obtained by imaging the subject using the MRI system; generating a first set of one or more MR images from the first input MR data; generating a second set of one or more MR images from the second input MR data; aligning the first set of MR images and the second set of MR images using a neural network model to obtain aligned first and second sets of MR images, the neural network model comprising a first neural network and a second neural network, the aligning comprising: estimating, using the first neural network, a first transformation between the first set of MR images and the second set of MR images; generating a first updated set of MR images from the second set of MR images using the first transformation; estimating, using the second neural network, a second transformation between the first set of MR images and the first updated set of MR images; and aligning the first set of MR images and the second set of MR images at least in part by using the first transformation and the second transformation; combining the aligned first and second sets of MR images to obtain a combined set of one or more MR images; and outputting the combined set of one or more MR images.

Some embodiments provide for a magnetic resonance imaging (MRI) system, comprising: a magnetics system having a plurality of magnetics components to produce magnetic fields for performing MRI; and at least one processor configured to perform: obtaining first input MR data by imaging the subject using the MRI system; obtaining second input MR data by imaging the subject using the MRI system; generating a first set of one or more MR images from the first input MR data; generating a second set of one or more MR images from the second input MR data; aligning the first set of MR images and the second set of MR images using a neural network model to obtain aligned first and second sets of MR images, the neural network model comprising a first neural network and a second neural network, the aligning comprising: estimating, using the first neural network, a first transformation between the first set of MR images and the second set of MR images; generating a first updated set of MR images from the second set of MR images using the first transformation; estimating, using the second neural network, a second transformation between the first set of MR images and the first updated set of MR images; and aligning the first set of MR images and the second set of MR images at least in part by using the first transformation and the second transformation; combining the aligned first and second sets of MR images to obtain a combined set of one or more MR images; and outputting the combined set of one or more MR images.

Some embodiments provide for a system, comprising at least one processor configured to perform: obtaining first input MR data obtained by imaging the subject using the MRI system; obtaining second input MR data obtained by imaging the subject using the MRI system; generating a first set of one or more MR images from the first input MR data; generating a second set of one or more MR images from the second input MR data; aligning the first set of MR images and the second set of MR images using a neural network model to obtain aligned first and second sets of MR images, the neural network model comprising a first neural network and a second neural network, the aligning comprising: estimating, using the first neural network, a first transformation between the first set of MR images and the second set of MR images; generating a first updated set of MR images from the second set of MR images using the first transformation; estimating, using the second neural network, a second transformation between the first set of MR images and the first updated set of MR images; and aligning the first set of MR images and the second set of MR images at least in part by using the first transformation and the second transformation; combining the aligned first and second sets of MR images to obtain a combined set of one or more MR images; and outputting the combined set of one or more MR images.

Some embodiments provide for a method for generating magnetic resonance (MR) images of a subject from MR data obtained by a magnetic resonance imaging (MRI) system, the method comprising: obtaining input MR data obtained by imaging the subject using the MRI system; generating a plurality of transformed input MR data instances by applying a respective first plurality of transformations to the input MR data; generating a plurality of MR images from the plurality of transformed input MR data instances and the input MR data using a non-linear MR image reconstruction technique; generating an ensembled MR image from the plurality of MR images at least in part by: applying a second plurality of transformations to the plurality of MR images to obtain a plurality of transformed MR images; and combining the plurality of transformed MR images to obtain the ensembled MR image; and outputting the ensembled MR image.

Some embodiments provide for at least one non-transitory computer-readable storage medium storing processor-executable instructions that, when executed by at least one processor, cause the at least one processor to perform a method for generating magnetic resonance (MR) images of a subject from MR data obtained by a magnetic resonance imaging (MRI) system, the method comprising: obtaining input MR data obtained by imaging the subject using the MRI system; generating a plurality of transformed input MR data instances by applying a respective first plurality of transformations to the input MR data; generating a plurality of MR images from the plurality of transformed input MR data instances and the input MR data using a non-linear MR image reconstruction technique; generating an ensembled MR image from the plurality of MR images at least in part by: applying a second plurality of transformations to the plurality of MR images to obtain a plurality of transformed MR images; and combining the plurality of transformed MR images to obtain the ensembled MR image; and outputting the ensembled MR image.

Some embodiments provide for at least one a magnetic resonance imaging (MRI) system configured to capture a magnetic resonance (MR) image, the MRI system comprising: a magnetics system having a plurality of magnetics components to produce magnetic fields for performing MRI; and at least one processor configured to perform: obtaining input MR data obtained by imaging the subject using the MRI system; generating a plurality of transformed input MR data instances by applying a respective first plurality of transformations to the input MR data; generating a plurality of MR images from the plurality of transformed input MR data instances and the input MR data using a non-linear MR image reconstruction technique generating an ensembled MR image from the plurality of MR images at least in part by: applying a second plurality of transformations to the plurality of MR images to obtain a plurality of transformed MR images; and combining the plurality of transformed MR images to obtain the ensembled MR image; and outputting the ensembled MR image.

Some embodiments provide for a system, comprising at least one processor configured to perform: obtaining input MR data obtained by imaging the subject using the MRI system; generating a plurality of transformed input MR data instances by applying a respective first plurality of transformations to the input MR data; generating a plurality of MR images from the plurality of transformed input MR data instances and the input MR data using a non-linear MR image reconstruction technique; generating an ensembled MR image from the plurality of MR images at least in part by: applying a second plurality of transformations to the plurality of MR images to obtain a plurality of transformed MR images; and combining the plurality of transformed MR images to obtain the ensembled MR image; and outputting the ensembled MR image.

Some embodiments provide for a method for generating magnetic resonance (MR) images from MR data obtained by a magnetic resonance imaging (MRI) system comprising a plurality of RF coils configured to detect RF signals. The method comprising: obtaining a plurality of input MR datasets obtained by the MRI system to image a subject, each of the plurality of input MR datasets comprising spatial frequency data and obtained using a respective RF coil in the plurality of RF coils; generating a respective plurality of MR images from the plurality of input MR datasets by using an MR image reconstruction technique; estimating, using a neural network model, a plurality of RF coil profiles corresponding to the plurality of RF coils; generating an MR image of the subject using the plurality of MR images and the plurality of RF coil profiles; and outputting the generated MR image.

Some embodiments provide for a magnetic resonance imaging (MRI) system, comprising: a magnetics system having a plurality of magnetics components to produce magnetic fields for performing MRI, the magnetics system comprising a plurality of RF coils configured to detect MR signals; and at least one processor configured to perform: obtaining a plurality of input MR datasets obtained by the MRI system to image a subject, each of the plurality of input MR datasets comprising spatial frequency data and obtained using a respective RF coil in the plurality of RF coils; generating a respective plurality of MR images from the plurality of input MR datasets by using an MR image reconstruction technique; estimating, using a neural network model, a plurality of RF coil profiles corresponding to the plurality of RF coils; generating an MR image of the subject using the plurality of MR images and the plurality of RF coil profiles; and outputting the generated MR image.

Some embodiments provide for a system comprising at least one processor configured to perform: obtaining a plurality of input MR datasets obtained by an MRI system to image a subject, each of the plurality of input MR datasets comprising spatial frequency data and obtained using a respective RF coil in a plurality of RF coils of the MRI system; generating a respective plurality of MR images from the plurality of input MR datasets by using an MR image reconstruction technique; estimating, using a neural network model, a plurality of RF coil profiles corresponding to the plurality of RF coils; generating an MR image of the subject using the plurality of MR images and the plurality of RF coil profiles; and outputting the generated MR image.

Some embodiments provide for at least one non-transitory computer readable storage medium storing processor-executable instructions that, when executed by at least one processor, cause the at least one processor to perform a method for generating magnetic resonance (MR) images of a subject from MR data obtained by a magnetic resonance imaging (MRI) system having a plurality of RF coils configured to detect MR signals. The method comprises: obtaining a plurality of input MR datasets obtained by the MRI system to image a subject, each of the plurality of input MR datasets comprising spatial frequency data and obtained using a respective RF coil in the plurality of RF coils; generating a respective plurality of MR images from the plurality of input MR datasets by using an MR image reconstruction technique; estimating, using a neural network model, a plurality of RF coil profiles corresponding to the plurality of RF coils; generating an MR image of the subject using the plurality of MR images and the plurality of RF coil profiles; and outputting the generated MR image.

Some embodiments provide for a method for generating magnetic resonance (MR) images from MR data obtained by a magnetic resonance imaging (MRI) system comprising a plurality of RF coils configured to detect RF signals. The method comprises: obtaining a plurality of input MR datasets obtained by the MRI system to image a subject, each of the plurality of input MR datasets comprising spatial frequency data and obtained using a respective RF coil in the plurality of RF coils; generating, from the plurality of input MR datasets and using a geometric coil compression technique, a plurality of virtual input MR datasets having fewer input MR datasets than the first plurality of input MR datasets; generating a plurality of MR images from the plurality of virtual input MR datasets by applying a neural network MR image reconstruction technique to the plurality of virtual input MR datasets; generating an MR image of the subject by combining the plurality of MR images; and outputting the generated MR image.

Some embodiments provide for a magnetic resonance imaging (MRI) system, comprising: a magnetics system having a plurality of magnetics components to produce magnetic fields for performing MRI, the magnetics system comprising a plurality of RF coils configured to detect MR signals; and at least one processor configured to perform: obtaining a plurality of input MR datasets obtained by the MRI system to image a subject, each of the plurality of input MR datasets comprising spatial frequency data and obtained using a respective RF coil in the plurality of RF coils; generating, from the plurality of input MR datasets and using a geometric coil compression technique, a plurality of virtual input MR datasets having fewer input MR datasets than the first plurality of input MR datasets; generating a plurality of MR images from the plurality of virtual input MR datasets by applying a neural network MR image reconstruction technique to the plurality of virtual input MR datasets; generating an MR image of the subject by combining the plurality of MR images; and outputting the generated MR image.

The foregoing is a non-limiting summary of the invention, which is defined by the attached claims.

BRIEF DESCRIPTION OF THE DRAWINGS

Various aspects and embodiments of the disclosed technology will be described with reference to the following figures. It should be appreciated that the figures are not necessarily drawn to scale.

FIG. 9 illustrates a block diagram of an example pipeline for motion correction, in accordance with some embodiments of the technology described herein.

FIG. 10 is a flowchart of an illustrative process 1000 for generating training data to train a neural network for aligning one or more images, in accordance with some embodiments of the technology described herein.

DETAILED DESCRIPTION

Figure 1:
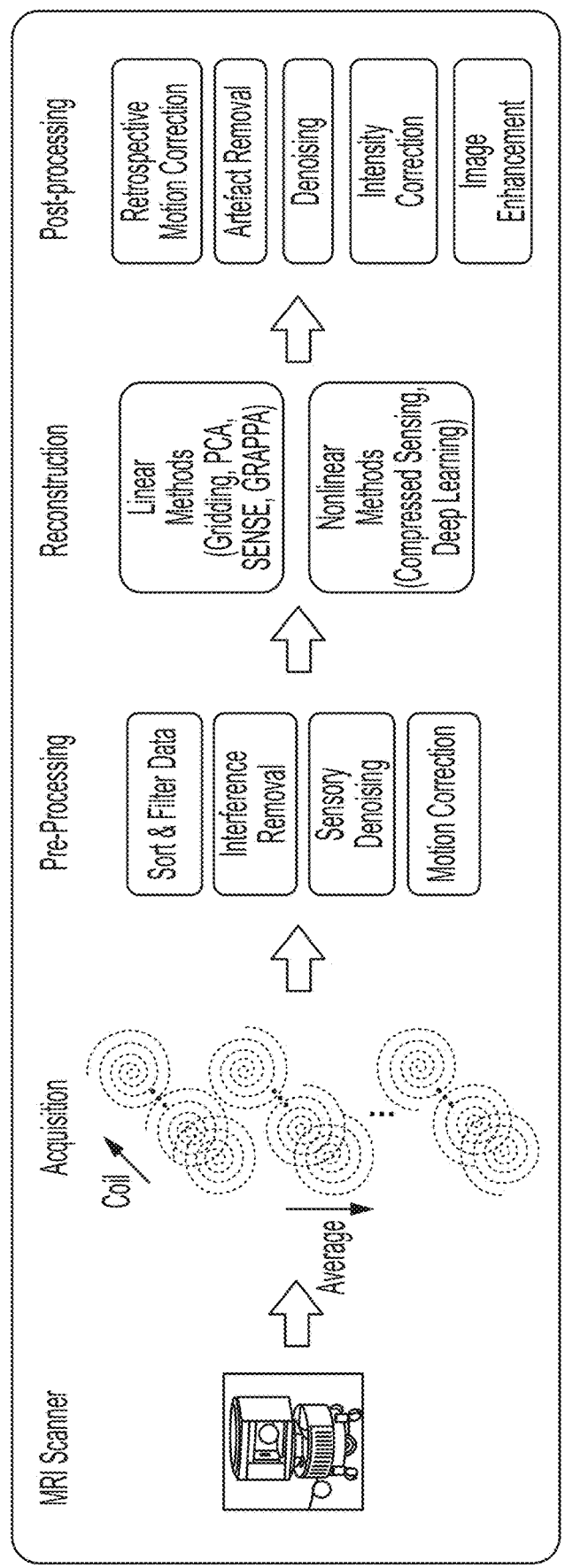
FIG. 1 is a diagram illustrating various types of processing performed on data collected by an MRI system while imaging a subject to generate an MR image of the subject.

Conventional techniques for processing MRI data to generate MR images of patients involve applying different computational tools to perform different tasks part of the processing pipeline for generating MR images from the MRI data. For example, as shown in FIG. 1, the processing pipeline may involve performing various pre-processing, reconstruction, and post-processing tasks on data acquired by an MRI system. The pre-processing tasks may include sorting and filtering of data, correcting the data for motion, and suppressing RF artefacts (e.g., external RF interference generated by any device(s) external to the MRI system, internal RF interference generated by any component(s) of the MRI system outside of its imaging region, and noise generated by the receive circuitry of the MRI system) in the data. After pre-processing, the pipeline may involve reconstructing MR images from the pre-processed data using linear methods (e.g., gridding, principle components analysis (PCA), sensitivity encoding (SENSE), generalized auto-calibrating partial parallel acquisition (GRAPPA) or non-linear methods (e.g., compressed sensing, deep learning)). Next, the resulting images may be post processed to perform retrospective motion correction, artefact removal, denoising, intensity correction, and/or image enhancement.

The inventors have appreciated that a fundamental limitation of such conventional MRI data processing techniques is that each of the tasks in the processing pipeline is tacked individually. Even though performance of the tasks is sequenced, solving each such task individually can result in loss of information at intermediate stages. Moreover, features that can be mutually exploited in multiple stages may be missed. As a result, the performance of the overall pipeline is sub-optimal resulting in lower quality and lower-SNR images, especially in settings (e.g., low-field MRI, undersampled data) where the sensor data is noisy and incomplete.

To address shortcomings of conventional MRI processing pipelines, the inventors have developed a unified deep-learning processing pipeline for processing MRI data to generate MR images of patients. The deep learning processing pipeline developed by the inventors involves using multiple neural networks to perform different pipeline tasks. Examples of such tasks include removing artefacts (e.g., interference, noise, corrupted readout lines) from input MR spatial frequency data, reconstructing images from the input MR spatial frequency data, combining MR images generated from data collected by different RF coils, aligning sets of MR images to one another to compensate for patient motion, combining aligned sets of MR images to increase the image signal to noise (SNR), correcting for inhomogeneous intensity variations. In some embodiments, at least some (e.g., all) of these tasks may be performed by respective neural networks.

In some embodiments, the neural networks in the processing pipeline may be jointly trained. In this way, parameters of neural networks for performing different tasks (e.g., interference removal, RF coil profile estimation, reconstruction, and motion correction) may be optimized jointly using a common set of training data and using a common objective metric. In some embodiments, the common objective metric may be a weighted combination of loss functions for learning parameters of the neural networks in the deep learning processing pipeline. Each of the neural networks in the pipeline may be trained to perform a respective task and the common objective metric may include one or more loss function (e.g., as part of the weighted combination) for the respective task. Examples of such loss functions are provided herein.

This "end-to-end" deep learning processing pipeline allows any improvements made in individual earlier processing stages to propagate to and be used by subsequent processing stages in the pipeline. As a result, the quality and SNR of MR images generated by the deep learning pipeline is higher than that produced by conventional processing pipelines, which is an improvement in MRI technology. In addition, since neural network calculations may be performed efficiently using specialized hardware (e.g., one or more graphics processing units (GPUs)), these calculations may be offloaded to such hardware freeing up resources of other onboard processors to perform different tasks—the overall load on the CPUs is reduced. This is a benefit that cannot be achieved using conventional pipelines as many of the algorithms used in conventional pipelines (e.g., compressed sensing) are not designed for efficient implementation on GPUs. Thus, the techniques described herein also provide an improvement to computing technology.

Accordingly, some embodiments provide for a method for generating magnetic resonance (MR) images of a subject from MR data obtained by a magnetic resonance imaging (MRI) system. The method comprises: (1) obtaining input MR spatial frequency data obtained by imaging the subject using the MRI system; and (2) generating an MR image of the subject from the input MR spatial frequency data using a neural network model comprising: (a) a pre-reconstruction neural network (e.g., pre-reconstruction neural network 210) configured to process the input MR spatial frequency data; (b) a reconstruction neural network (e.g., reconstruction neural network 212) configured to generate at least one initial image of the subject from output of the pre-reconstruction neural network; and (c) a post-reconstruction neural network (e.g., post-reconstruction neural network 214) configured to generate the MR image of the subject from the at least one initial image of the subject.

In some embodiments, the input MR spatial frequency data may be under-sampled relative to a Nyquist criterion. For example, in some embodiments, the input MR spatial frequency data may include less than 90% (or less than 80%, or less than 75%, or less than 70%, or less than 65%, or less than 60%, or less than 55%, or less than 50%, or less than 40%, or less than 35%, or any percentage between 25 and 100) of the number of data samples required by the Nyquist criterion. In some embodiments, the reconstruction neural network was trained to reconstruct MR images from spatial frequency MR data under-sampled relative to a Nyquist criterion.

In some embodiments, the input MR spatial frequency data may have been obtained using a non-Cartesian (e.g., radial, spiral, rosette, variable density, Lissajou, etc.) sampling trajectory, which may be used to accelerate MRI acquisition and/or be robust to motion by the subject.

In some embodiments, the pre-reconstruction neural network comprises a first neural network configured to suppress RF interference (e.g., neural network 224), the first neural network comprising one or more convolutional layers. Additionally or alternatively, the pre-reconstruction neural network comprises a second neural network configured to suppress noise (e.g., neural network 226), the second neural network comprising one or more convolutional layers. Additionally or alternatively, the pre-reconstruction neural network comprises a third neural network configured to perform line rejection (e.g., neural network 220), the third neural network comprising one or more convolutional layers.

In some embodiments, the reconstruction neural network is configured to perform data consistency processing using a non-uniform Fourier transformation for transforming image data to spatial frequency data. In some embodiments, the reconstruction neural network is configured to perform data consistency processing using the non-uniform Fourier transformation at least in part by applying the non-uniform Fourier transformation on data by applying a gridding interpolation transformation, a fast Fourier transformation, and a de-apodization transformation to the data.

In some embodiments, the MRI system comprises a plurality of RF coils, the at least one initial image of the subject comprises a plurality of images, each of the plurality of images generated from a portion of the input MR spatial frequency data collected by a respective RF coil in a plurality of RF coils, and the post-reconstruction neural network comprises a first neural network (e.g., neural network 232) configured to estimate a plurality of RF coil profiles corresponding to the plurality of RF coils. In some such embodiments, the method further comprises: generating the MR image of the subject using the plurality of MR images and the plurality of RF coil profiles.

In some embodiments, the at least one initial image of the subject comprises a first set of one or more MR images and a second set of one or more MR images, and the post-reconstruction neural network comprises a second neural network (e.g., neural network 234) for aligning the first set of MR images and the second set of MR images.

In some embodiments, the post-reconstruction neural network comprises a neural network (e.g., neural network 238) configured to suppress noise in the at least one initial image and/or at least one image obtained from the at least one initial image.

In some embodiments, the pre-reconstruction neural network, the reconstruction neural network, and the post-reconstruction neural network are jointly trained with respect to a common loss function. In some embodiments, the common loss function is a weighted combination of a first loss function for the pre-reconstruction neural network, a second loss function for the reconstruction neural network, and a third loss function for the post-reconstruction neural network.

The neural networks described herein may be configured to operate on data in any suitable domain. For example, one or more of the neural networks described herein may be configured to receive as input, data in the "sensor domain", "spatial-frequency domain" (also known as k-space), and/or the image domain. Data in the "sensor domain" may comprise raw sensor measurements obtained by an MRI system. Sensor domain data may include measurements acquired line-by-line for a set of coordinates specified by a sampling pattern. A line of measurements may be termed a "readout" line. Each measurement may be a spatial frequency. As such, sensor domain data may include multiple readout lines. For example, if p readout lines were measured and each readout line included m samples, the sensor domain data may be organized in an m×p matrix. Knowing the k-space coordinates associated with each of the m×p samples, the sensor domain data may be re-organized into the corresponding k-space data, and may be then considered to be spatial frequency domain data. Data in the sensor domain as well as the data in k-space is spatial frequency data, but the spatial frequency data is organized differently in these two domains. Image-domain data may be obtained by applying an inverse Fourier transformation (e.g., an inverse fast Fourier transform if the samples fall on a grid) to k-space data.

In addition, it should be appreciated that the sensor domain, k-space, and image domain are not the only domains on which the neural networks described herein may operate. For example, the data in a source domain (e.g., sensor domain, k-space, or image domain) may be further transformed by an invertible transformation (e.g., 1D, 2D, or #d Fourier, Wavelet, and/or short-time Fourier transformation, etc.) to a target domain, the neural network may be configured to receive as input data in the target domain, and after completing processing, the output may be transformed back to the source domain.

A neural network may be configured to operate on data in a particular domain being trained to operate on input in the particular domain. For example, a neural network configured to operate on data in domain D, may be trained on input-output pairs, with the input in the pairs being the domain D. In some embodiments, the output of a neural network may be in the same domain as its input, but in other embodiments, the input is not in the same domain as its input (e.g., the reconstruction neural network 212 may receive input data in the spatial frequency domain and output images in the image domain).

As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 mT are referred to herein as "ultra-low field."

In some embodiments, the techniques described herein for generating MR images from input MR spatial frequency data may be adapted for application to spatial frequency data collected using a low-field MRI system, including, by way of example and not limitation, any of the low-field MR systems described herein and/or any low-field MR systems described in U.S. Pat. No. 10,222,434, filed on Jan. 24, 2018, titled "Portable Magnetic Resonance Imaging Methods and Apparatus," which is incorporated by reference in its entirety.

Following below are more detailed descriptions of various concepts related to, and embodiments of, methods and apparatus for generating MR images from spatial frequency domain data. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

Figure 2A:
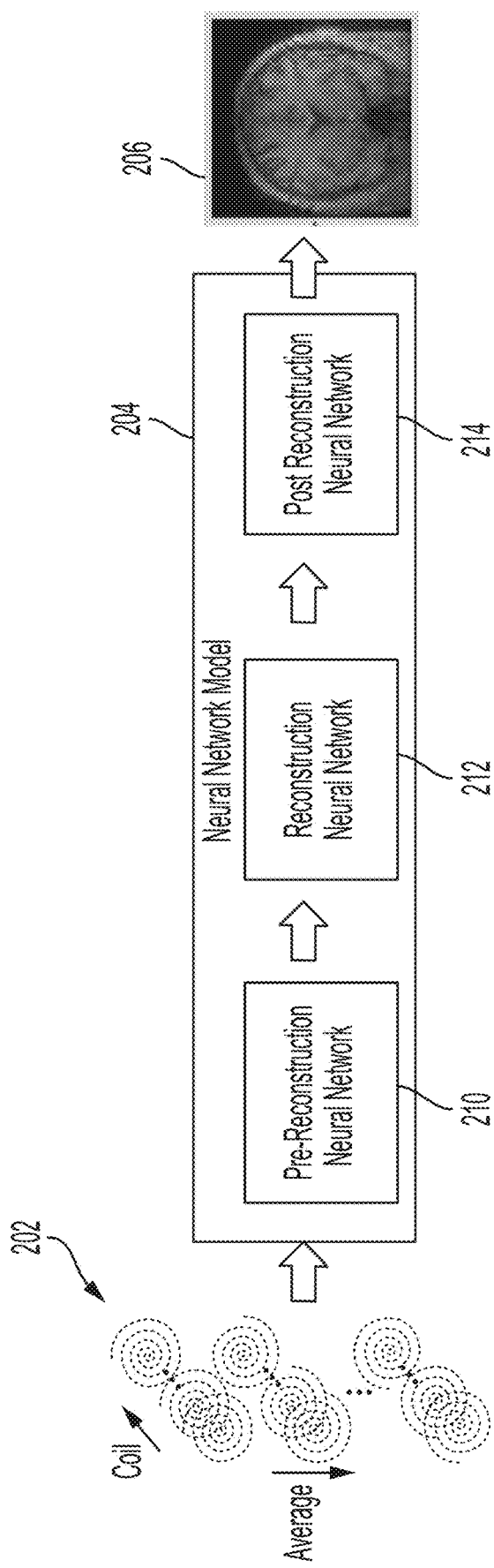
FIG. 2A is a diagram illustrating processing performed by a neural network model on data collected by an MRI system while imaging a subject to generate an MR image of the subject, in accordance with some embodiments of the technology described herein.

FIG. 2A is a diagram illustrating processing performed by a neural network model on data collected by an MRI system while imaging a subject to generate an MR image of the subject, in accordance with some embodiments of the technology described herein. As shown in FIG. 2A, neural network model 204 may be configured to implement a deep learning pipeline to estimate one or more MR images 206 from input MR spatial frequency data 202. The neural network model 204 may include multiple neural networks for performing various processing pipeline tasks. In some embodiments, at least some (e.g., all) of the neural networks part of neural network model 204 may be trained jointly on a common set of training data and with respect to a common loss function.

It should be appreciated that although, in some embodiments, all tasks in the pipeline for generating MR images from input MR spatial frequency data are performed by respective neural networks (e.g., part of neural network 204), in other embodiments, one or more such tasks may be performed by techniques other than neural networks. Notwithstanding, in such embodiments, the neural networks that are part of the processing pipeline may be trained jointly on a common set of training data and with respect to a common loss function.

In the illustrated embodiment, neural network model 204 includes pre-reconstruction neural network 210 configured to perform one or more pre-processing tasks (e.g., motion correction, RF interference removal, noise removal), reconstruction neural network 212 configured to reconstruct one or more images from the output of the neural network 210 (e.g., including when the MR data is undersampled), and post-reconstruction neural network 214 configured to perform one or more post-processing tasks (e.g., combining images generated from data collected by different coils, image registration, signal averaging, denoising, and correction for intensity variation) on the MR images generated by the reconstruction neural network 212. Aspects of the pre-reconstruction neural network 210 are described herein, including with reference to FIGS. 2B, and 4A-4D. Aspects of the reconstruction neural network 212 are described herein, including with reference to FIGS. 3A-3E. Aspects of the post-reconstruction neural network 214 are described herein, including with reference to FIGS. 2C and 6-14. Aspects of training neural network model 204 are described herein including with reference to FIG. 5.

In some embodiments, input MR spatial frequency data 202 may be collected by one or multiple RF coils of an MRI system. The data 202 may be collected using a Cartesian sampling trajectory or any suitable type of non-Cartesian sampling trajectory (e.g., radial, spiral, rosette, variable density, Lissajou, etc.). In some embodiments, the data 202 may be fully-sampled data (data collected by sampling spatial frequency space so that the corresponding Nyquist criterion is not violated). In some embodiments, the data 202 may be under-sampled data (data containing fewer points than what is required by spatial Nyquist criteria). In some embodiments, the data 202 may exhibit artefacts due to the presence of external RF interference, internal RF interference, and/or noise generated by the MR receiver chain and/or a subject (or object) being imaged. In some embodiments, the data may include distortions caused by movement of the patient during imaging.

Figure 2B:
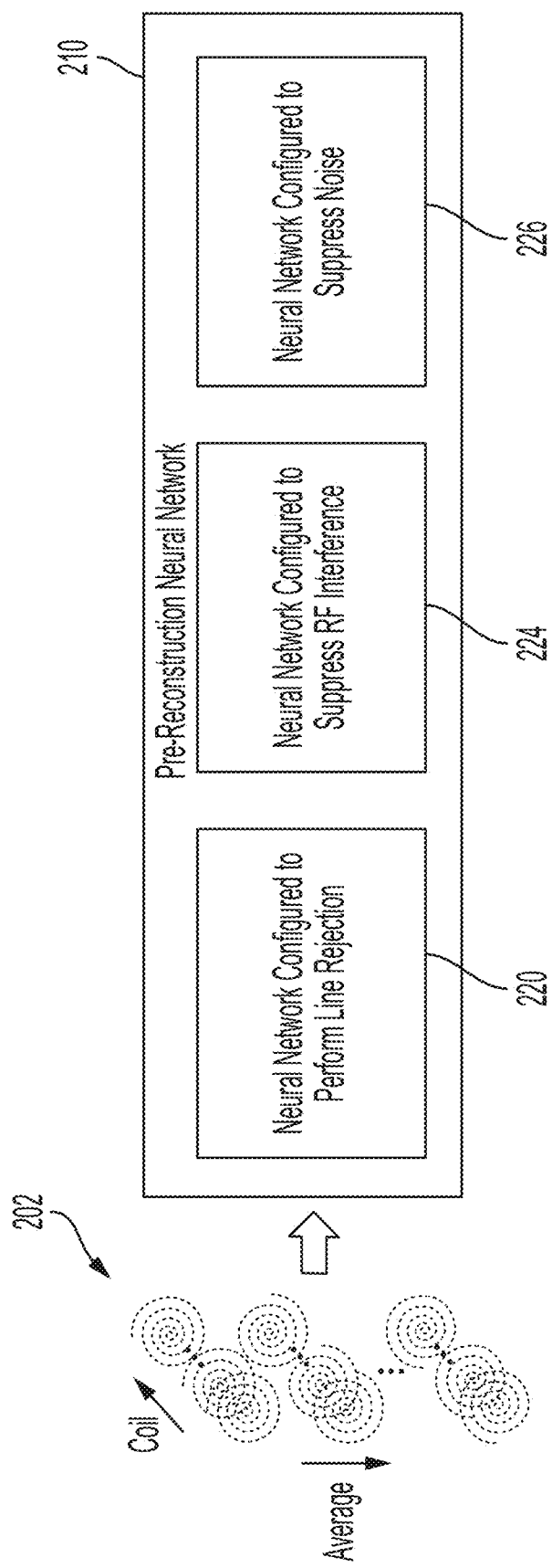
FIG. 2B is a diagram of illustrative components of the pre-reconstruction neural network part of the neural network model of FIG. 2A, in accordance with some embodiments of the technology described herein.

FIG. 2B is a diagram of illustrative components of the pre-reconstruction neural network 210 part of the neural network model 204 of FIG. 2A, in accordance with some embodiments of the technology described herein. The pre-reconstruction neural network 210 may include one, two, three, four, and/or any other suitable number of neural networks each configured to perform a pre-processing task in the overall data processing pipeline.

In the illustrated embodiment of FIG. 2B, pre-reconstruction neural network 210 includes three neural networks: (1) a neural network 220 configured to perform line rejection; (2) a neural network 224 configured to suppress RF interference (external and/or internal RF interference); and (3) a neural network 226 configured to suppress noise. In the illustrated embodiment, pre-reconstruction neural network 210 includes all three neural networks 220, 224, and 226. In other embodiments, neural network 210 may include any one or any two of the neural networks 220, 224, 226. Also, neural network 210 may include one or more other neural networks for performing pre-processing tasks in the pipeline, as aspects of the technology described herein are not limited in this respect.

In some embodiments, neural network 220 may be configured to process portions (e.g., readout lines) of sensor data 202 to determine whether any of these portions are corrupted, for example, due to motion of the patient during their acquisition. In some embodiments, the input to neural network 220 may be a portion (e.g., a readout line) of data 202, and the output of the neural network may provide an indication of whether or not the portion of data 202 is corrupted (e.g., due to patient motion).

In some embodiments, the input to neural network 220 may further include data from one or more auxiliary sensors (e.g., one or more optical sensors, one or more RF sensors, one or more accelerometers and/or gyroscopes) configured to detect patient movement. Such sensors may be part of the MRI system that acquired the data 202 (e.g., one or more RF sensors, accelerometers, and/or gyroscopes may be coupled to a helmet housing one or more RF receive coils) or may be external to the MRI system but deployed so as to monitor patient movement (e.g., one or more cameras may be positioned to observe the imaging region and/or the patient to detect patient movement).

In some embodiments, the neural network 220 may be a convolutional neural network and may have one or more convolutional layers, one or more transpose convolutional layers, one or more non-linearity layers, and/or one or more fully connected layers. The neural network 220 may be implemented using any of the neural network architectures described herein including with reference to FIG. 3D by way of example and not limitation. Alternatively, a ResNet type architecture may be used where convolutional blocks have residual connections.

In some embodiments, the neural network 220 may be applied to the data 202 after that data has been processed (e.g., by neural networks 224 and 226) to suppress (e.g., reduce and/or eliminate) RF artefacts such as RF interference and RF noise. In other embodiments, the neural network 220 may be applied to the data 202 before it has been processed to suppress RF artefacts.

Returning to FIG. 2B, in some embodiments, neural network 224 may be configured to suppress RF interference. As described herein, RF interference may be external RF interference generated by one or more devices external to the MRI system, as the case may be for low-field MRI systems deployed outside of shielded rooms (e.g., Faraday cages) in various environments (e.g., emergency room, an ICU, an ambulance, a doctor's office, etc.) and in the presence of various devices (medical equipment, smart phones, televisions, etc.). RF interference may also include internal RF interference generated by one or more components of the MRI system located outside of its imaging region (e.g., power supply, gradient coils, gradient coil amplifiers, RF amplifiers, etc.).

In some embodiments, the neural network 224 may be a convolutional neural network, and may have one or more convolutional layers, one or more transpose convolutional layers, one or more non-linearity layers, one or more pooling layers (e.g., average, spectral, maximum) and one or more corresponding unpooling layers, and/or one or more fully connected layers. The neural network 224 may be implemented using any of the neural network architectures described herein including with reference to FIGS. 4A-4D by way of example and not limitation. Alternatively, a ResNet type architecture may be used where convolutional blocks have residual connections.

In some embodiments, the neural network 224 may be trained using particular loss functions described next. First, some notation is introduced. An MRI system may have one or multiple RF coils configured to detect MR signals in the imaging region of the MR system. Let the number of such RF coils be denoted by $N_C$. For each RF coil c configured to detect MR signals in the imaging region, let $s_c$ denote the detected signal. This detected signal contains three different components as follows: (1) the target MR signal data, $x_c$ for coil c; (2) the noise $n_c$ corrupting the signal (e.g., noise generated by the MR receiver chain for coil c, noise generated by the subject (or object) being imaged); and (3) external and/or internal RF interference $i_c$. Accordingly, $s_c = x_c + n_c + i_c$. Moreover, by locating $N_P$ RF coils outside of the system noise observed outside of the system (which is correlated with $s_c$'s) called $s_c^{nz}$ may be acquired. Thus, the observed signal may expressed according to:

$$s_c = x_c + n_c + i_c = s_c^{NI} + i_c.$$

In some embodiments, the neural network 224 may be trained to suppress RF interference $i_c$. To this end, training data may be created that includes all of the components of $s_c$ separately so that ground truth is available. For example, each of $x_c$, $n_c$, and $i_c$, may be generated synthetically using a computer-based simulation and/or data observed using an MRI system. For example, to generate $i_c$ one can synthetically add structured noise lines to $s_c$ or acquire $s_c$ while no object is located inside of the system. As another example, an MRI system may have one or more RF coils outside of the imaging region that may be used to observe artefacts outside of the imaging region (without also detecting MR signals) and this coil or coils may be used to measure RF interference.

The input to the neural network 224 may be: (1) the signal $s_c$ for each coil, so that the neural network suppresses RF interference for each coil separately; (2) the signals $s_c$ for all the coils as separate channels, so that the neural network suppresses RF interference for all coils at the same time; or (3) the signals $s_c$ for each coil, as separate channels, as well as the signals $s_c^{nz}$'s as extra information in other channels (not to be suppressed, but rather to suppress RF interference in the signals $s_c$. The output produced by the neural network 224, corresponding to the input, may be: (1) $s_c^{NI}$ for each coil c separately; or (2) all $s_c^{NI}$'s as separate channels (when the input is of the latter two cases). Additionally, in some embodiments, the input to this block can be $s_c$ of all $N_{avg}$ averages together to incorporate even more information. In this case the output will be all denoise coil data for all averages together. This may be helpful when multiple observations are made by each coil.

Any of numerous types of loss functions may be used for training a neural network for suppressing RF interference, and various examples of loss functions are provided herein. As one example, for training a neural network 224 for suppressing RF interference in data acquired using a single coil, the following loss function may be employed:

$$\mathcal{L}(\theta) = \|F(s_c^{NI}) - f_{CNN}(F(s_c)|\theta)\|_2^2 + \|f_{CNN}(\nabla F(s_c)|\theta)\|_1 + \|W(s_c^{NI} - f_{CNN}(s_c|\theta))\|$$

where W is the weighting matrix, F is a 1D Fourier (spectral) transform, $\nabla$ is an image gradient, and $\theta$ represents parameters of the neural network 224 denoted in the equations by $f_{CNN}$.

In the multi-channel setting, the following loss function may be employed for training neural network 224:

$$\mathcal{L}(\theta) = \sum_{c=1}^{N_{coil}} \left( \|F(s_c^{NI}) - f_{CNN}(F(s)|\theta)_c\|_2^2 + \|f_{CNN}(\nabla F(s)|\theta)_c\|_1 + \|W(s_c^{NI} - f_{CNN}(s|\theta)_c)\| \right)$$

where $N_{coil}$ is the number of coils and $f_{CNN}(s)_c$ is denoised sensor data for coil c, where s includes all the signals $s_c$ arranged channel-wise.

Returning to FIG. 2B, in some embodiments, neural network 226 may be configured to suppress noise. For example, neural network 226 may be configured to suppress noise generated by operation of circuitry involved in the processing of signals recorded by the RF coil(s) of the MRI system, which circuitry may be termed the "MR receiver chain". The MR receiver chain may include various types of circuitry such as analog circuitry (e.g., one or more amplifiers, a decoupling circuit, an RF transmit/receive switch circuit, etc.), digital circuitry (e.g., a processor) and/or any suitable combination thereof. Some examples of MR receiver chain circuitry are described in U.S. Pat. App. Pub. No.: 2019/0353723, filed on May 21, 2019 (as application Ser. No. 16/418,414), titled "Radio-Frequency Coil Signal Chain For a Low-Field MRI System", which is incorporated by reference in its entirety.

In some embodiments, the neural network 226 may be a convolutional neural network, and may have one or more convolutional layers, one or more transpose convolutional layers, one or more non-linearity layers, one or more pooling layers (e.g., average, spectral, maximum) and one or more corresponding unpooling layers, and/or one or more fully connected layers. The neural network 226 may be implemented using any of the neural network architectures described herein including with reference to FIGS. 4A-4D by way of example and not limitation. Alternatively, a ResNet type architecture may be used where convolutional blocks have residual connections.

In some embodiments, the input to the neural network 226 may be: (1) $s_c$ for suppressing noise from each coil c separately; (2) all $s_c$'s as separate channels, for suppressing noise in all coils at the same time; (3) all $s_c$'s as separate channels as well as the data detected by coils outside of the imaging region ($s_p^{nz}$) as an additional information to use for denoising. In some embodiments, the output of the trained neural network may be: (1) $x_c$ or (2) all $x_c$'s for the multiple coils.

Any of numerous types of loss functions may be used for training the neural network 226 for suppressing noise. For example, for training a neural network for suppressing noise in data acquired using a single coil, the following loss function may be employed:

$$\mathcal{L}(\theta) = \|F(x) - f_{CNN}(F(s_c)|\theta)\|_2^2 + \|f_{CNN}(\nabla F(s_c)|\theta)\|_1 + \|W(x_c - f_{CNN}(s_c|\theta))\|$$

In some embodiments, when training neural network 2266 for suppressing noise in data acquired using multiple coils, the following loss function may be employed:

$$\mathcal{L}(\theta) = \sum_{C=1}^{N_{coil}} (\|F(x_c) - f_{CNN}(F(s)|\theta)_c\|_2^2 + \|f_{CNN}(\nabla F(s)|\theta)\|_1 + \|W(x_c - f_{CNN}(s|\theta)_c)\|).$$

Figure 2C:
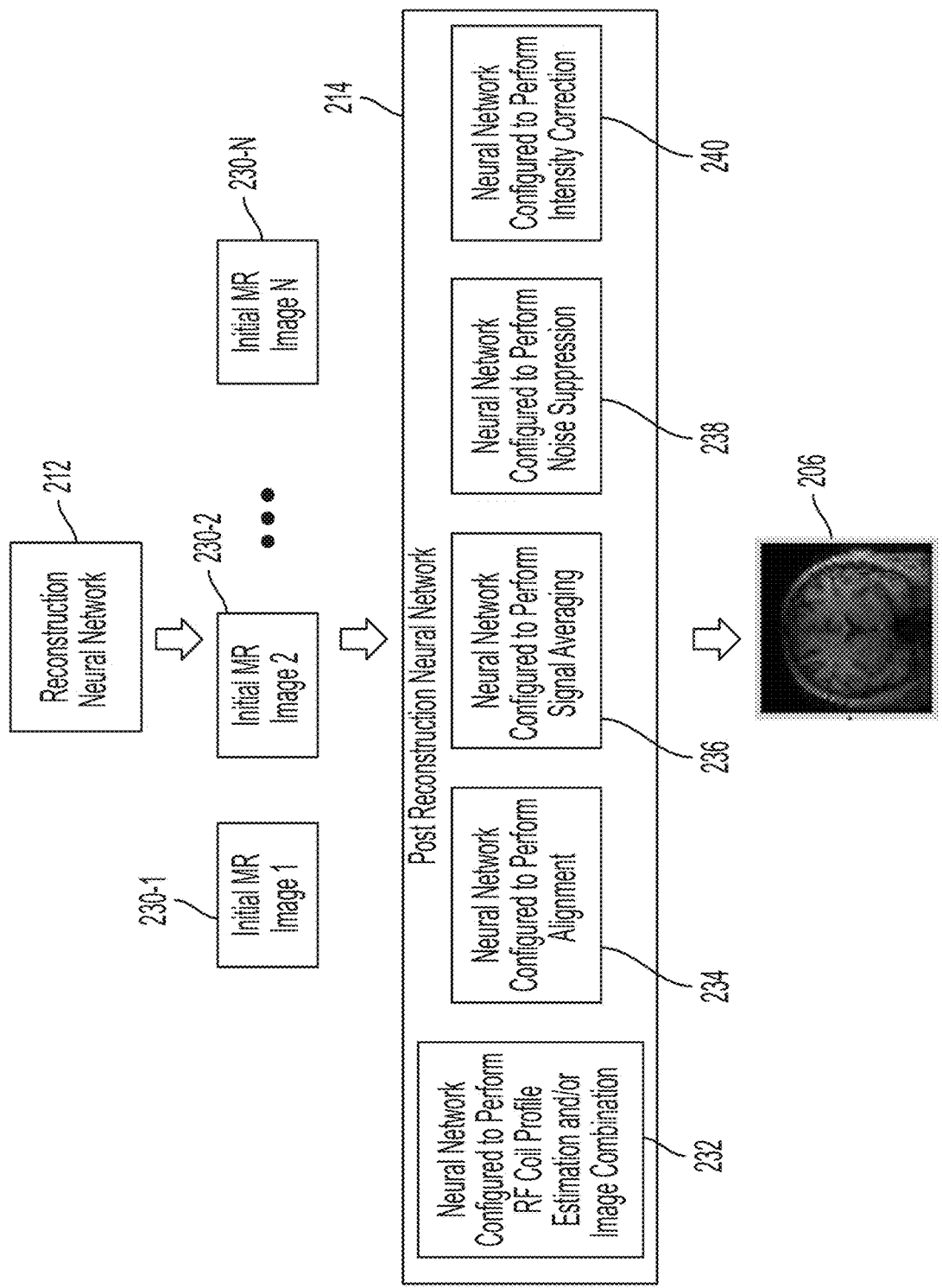
FIG. 2C is a diagram of illustrative components of the post-reconstruction neural network part of the neural network model of FIG. 2A, in accordance with some embodiments of the technology described herein.

FIG. 2C is a diagram of illustrative components of the post-reconstruction neural network 214 part of the neural network model 204 of FIG. 2A, in accordance with some embodiments of the technology described herein. As shown in FIG. 2C, reconstruction neural network 212 may generate one or multiple MR images upon reconstruction—these are the initial MR images 230-1, 230-2, . . . , 230-N.

There are multiple reasons for why reconstruction neural network 212 may generate multiple MR images. For example, in some embodiments, an MRI system may include multiple RF coils and the reconstruction neural network 212 may generate, for each particular one of the multiple RF coils, one or more MR images from data detected by that particular RF coil. Moreover, multiple images may be generated by the neural network 212 even from data collected by a single RF coil because: (1) each line may be acquired multiple times (for subsequent averaging to boost SNR); and (2) the data collected by a single RF coil may include data corresponding to each of multiple two-dimensional slices of a patient's anatomy. Accordingly, in some embodiments, the initial images 230-1, . . . , 230-N, may include multiple sets of MR images, with each of the sets of MR images generated using data collected by a respective RF coil from among the multiple RF coils of the MRI system, and each set of images may include one or multiple volumes of data (e.g., K volumes of data each including M slices per volume). However, in some embodiments, the collected MR data may be such that the reconstruction neural network 212 may generate only a single MR image, as aspects of the technology described herein are not limited in this respect.

In the illustrated embodiment of FIG. 2C, post-reconstruction neural network 214 includes five neural networks: (1) a neural network 232 configured to perform RF coil profile estimation and/or image combination across RF coils; (2) a neural network 234 configured perform alignment among multiple sets of one or more MR images to correct for patient motion; (3) a neural network 236 configured to perform signal averaging; (4) a neural network 238 configured to perform noise suppression; and (5) a neural network 240 configured to perform intensity correction.

In the illustrated embodiment of FIG. 2C, post-reconstruction neural network 214 includes all five neural networks 232, 234, 236, 238, and 240. In other embodiments, neural network 214 may include any one, or any two, or any three, or any four of the neural networks 232, 234, 236, 238, and 240. Also, neural network 214 may include one or more other neural networks for performing post-processing tasks in the pipeline, as aspects of the technology described herein are not limited in this respect.

Neural network 232 may be used in embodiments in which the MRI system collects data using multiple RF coils. In such embodiments, the neural network 232 may be used to combine the images (from among initial images 232) generated from data collected by different RF coils, but corresponding to the same slices. As described in more detail below in the "Coil Estimation" Section below, neural network 232 may be used to either estimate such a combined image directly or to estimate sensitivity profiles for the different RF coils, which in turn may be used to combine the images.

In some embodiments, the neural network 232 may be a convolutional neural network having one or more convolutional layers, one or more transpose convolutional layers, one or more non-linearity layers, one or more pooling layers and one or more corresponding unpooling layers, and/or one or more fully connected layers. For example, in some embodiments, the neural network 232 may have the architecture shown in FIG. 20B. Alternatively, a ResNet type architecture may be used where convolutional blocks have residual connections.

Returning to FIG. 2C, in some embodiments, neural network 234 may be configured to align two sets of one or more MR images to each other. In some instances, each set of MR images may correspond to a set of images for a given volume (e.g., a number of 2D slices that may be stacked to constitute a volume). Such an alignment allows for the sets of MR images to be averaged to increase the SNR. Performing the averaging without first performing alignment would introduce blurring due to, for example, movement of the patient during acquisition of the data being averaged.

In some embodiments, neural network 234 may be configured to align sets of one or more MR images by estimating one or more transformations (e.g., non-rigid, affine, rigid) between the sets of MR images. In some embodiments, neural network 234 may be implemented at least in part by using estimated parameter resampling (EPR). Aspects of illustrative implementations the neural network 234 are described herein including in the "Motion Correction" Section below.

Returning to FIG. 2C, in some embodiments, neural network 236 may be configured to perform signal averaging to increase the SNR of the final reconstructed MR image. Conventionally, this is performed by averaging multiply acquired data from the same imaging protocol (e.g., the same pulse sequence being repeatedly applied). An assumption underlying this conventional approach is that the images being averaged have almost independent and identically distributed (iid) noise, which will cancel when the images are combined. In practice, however, this assumption may be violated because the reconstruction is non-linear and because bias and correlation may be introduced by the MRI system.

The inventors have recognized that improved performance may be achieved if, instead of averaging images, a neural network is used to learn how to combine them. This would take into account various characteristics of the noise and MRI system that result in the iid assumption beneath the conventional averaging approach being violated. Suppose x is the ground truth target to be reconstructed. Suppose also that $N_{avg}$ measurements of x are acquired and individually reconstructed, yielding images $x_1, \ldots, x_{N_{avg}}$. Instead of averaging these images, the combination may be performed by neural network 236 denoted by $f_{cnn}(\cdot|\theta)$, which takes all $N_{avg}$ images as input and outputs a single combined image $x_{rec}$.

In some embodiments, the neural network 236 may be applied after neural network 234 is used to align corresponding sets of images so that blurring is not introduced through the combination performed by neural network 236.

The neural network 236 may be a convolutional neural network having one or more convolutional layers, one or more transpose convolutional layers, one or more non-linearity layers, one or more pooling layers and one or more corresponding unpooling layers, and/or one or more fully connected layers. For example, the network 236 may have a U-net type architecture. Alternatively, a ResNet type architecture may be used where convolutional blocks have residual connections.

In some embodiments, given the dataset $\mathcal{D}$, the neural network may be trained using the following loss function:

$$\mathcal{L}(\theta) = \sum_{j=1}^{|\mathcal{D}|} \|x^{(j)} - x_{rec}^{(j)}\|_2$$

Returning to FIG. 2C, in some embodiments, neural network 238 may be configured to suppress artefacts in the image domain. The neural network 238 may be a convolutional neural network, and may have one or more convolutional layers, one or more transpose convolutional layers, one or more non-linearity layers, one or more pooling layers (e.g., average, spectral, maximum) and one or more corresponding unpooling layers, and/or one or more fully connected layers. The neural network 238 may be implemented using any of the neural network architectures described herein including with reference to FIGS. 4A-4D by way of example and not limitation. Alternatively, a ResNet type architecture may be used where convolutional blocks have residual connections.

Suppressing artefacts in the image domain may facilitate reducing or removing noise generated by the acquisition system (e.g., MR receiver chain). The effects of such noise are more pronounced in low-field MRI system leading to a lower signal to noise ratio. Conventional techniques for suppressing noise in MR images involve using parametric filtering techniques such as anisotropic diffusion or non-local means filtering. The goal of these parametric filtering techniques is to remove noise in uniform image regions while preserving sharpness of the edges around anatomical structures. When the level of noise is high (as the case may be in low-field systems), applying the parametric filters typically results in smooth-looking images with loss of detail in low-contrast image regions. By contrast, using deep learning to suppress artefacts (e.g., noise) in the image domain using the neural network 238 results in sharp-looking images, while preserving structure even in low-contrast regions.

In some embodiments, training data may be created to reflect the effect of noise on MR images. The noise may be measured (e.g., using an MRI system) or synthesized. For example, a synthetic noise signal $e_c$ may be added to the image $x_c$ as follows: $x_c^n = x_c + e_c$, where the noise may be drawing from a Gaussian $e_c \sim N(0, \sigma_c)$ or Rician distribution, (assuming there is no correlation among coils for simplicity). In some embodiments, the neural network 238 may be trained, given a dataset $\mathcal{D}$, using content loss (structural similarity index (SSIM) loss or mean squared error loss) and an adversarial loss given by:

$$\mathcal{L}(\theta_G, \theta_D) = \sum_{i=1}^{|\mathcal{D}|} -D_{\theta_D}(G_{\theta_G}(x_c), x_c^n) + \lambda(1 - SSIM(x_c x_c^n)).$$

In the above expression for loss, the generator G is the filtering network and the discriminator D is trained to best differentiate between images filtered with the network G and original noise-free images (ground truth). In some embodiments, the parameters of the generator ($\theta_G$) and discriminator ($\theta_D$) neural networks may be optimized by establishing a minimax game between the generator and discriminator neural networks. The generator network may be trained to produce filtered images as close as possible to the ground truth and thus fool the discriminator neural network. On the other hand, the discriminator network may be trained to classify the input images as filtered or ground truth. Using an adversarial loss, like the one described above, helps to achieve sharp-looking filtered images while preserving structures even in low-contrast regions.

Returning to FIG. 2C, in some embodiments, neural network 240 may configured to suppress (e.g., reduce and/or eliminate) inhomogeneous intensity variations across image regions, which may result from combining images generated from data collected by different RF coils (e.g., via the application of neural network 232).

In some embodiments, the neural network 240 may be a convolutional neural network, and may have one or more convolutional layers, one or more transpose convolutional layers, one or more non-linearity layers, one or more pooling layers (e.g., average, spectral, maximum) and one or more corresponding unpooling layers, and/or one or more fully connected layers. The neural network 240 may be implemented using a U-Net architecture. Alternatively, a ResNet type architecture may be used where convolutional blocks have residual connections.

To generate training data for training neural network 240, image augmentation may be employed to simulate the intensity variations using unperturbed input images and a random histogram augmentation function $I_{(x)}$:

$$x''=I(x')$$

In some embodiments, the histogram augmentation function may be designed to enhance image contrast. Other image acquisition artifacts can be modeled this way as well. For example, geometric transformations applied to images, such as affine or nonlinear deformations T(r) yielding:

$$x''=I(x'(T(r))).$$

Figure 2D:
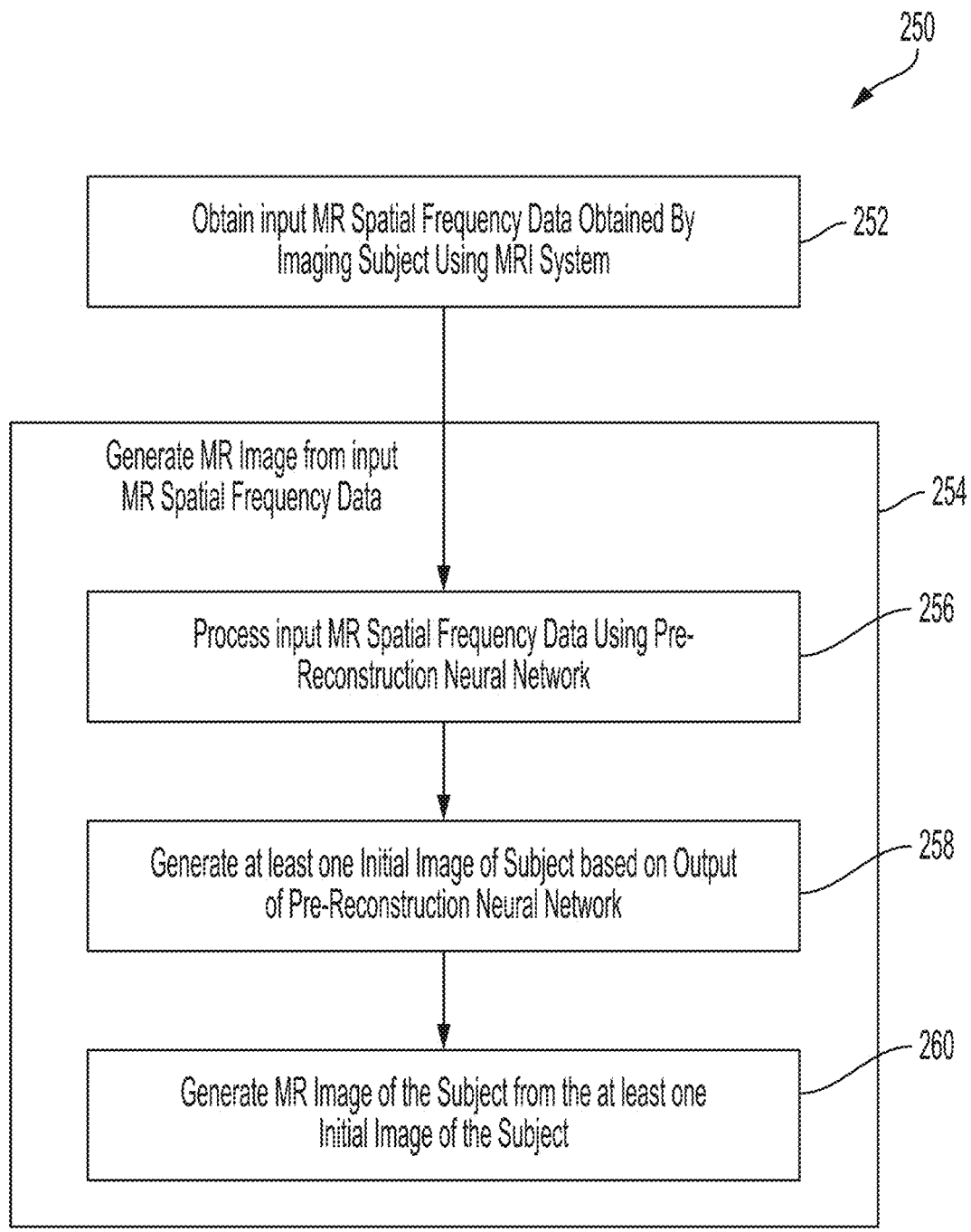
FIG. 2D is a flowchart of an illustrative process for generating an MR image from input MR spatial frequency data, in accordance with some embodiments of the technology described herein.

FIG. 2D is a flowchart of an illustrative process 250 for generating an MR image from input MR spatial frequency data, in accordance with some embodiments of the technology described herein. Process 250 may be performed by any suitable computing device(s). For example, process 250 may be performed by one or more processors (e.g., central processing units and/or graphics processing units) part of the MRI system and/or by one or more processors external to the MRI system (e.g., computers in an adjoining room, computers elsewhere in a medical facility, and/or on the cloud).

Process 250 begins at act 252, where the system performing process 250 obtains (e.g., accesses from memory or other non-transitory computer readable storage medium, receives over a network) input MR spatial frequency data obtained by imaging a subject using an MRI system. In the illustrative embodiment of FIG. 2D, the imaging itself is not part of process 250. However, in other embodiments, process 250 may include performing the imaging using the MRI system.

The input MR spatial frequency data may include data collected by one or multiple RF coils of the MRI system. The data 252 may be collected using a Cartesian sampling trajectory or any suitable type of non-Cartesian sampling trajectory (e.g., radial, spiral, rosette, variable density, Lissajou, etc.). In some embodiments, the data 252 may be fully-sampled data (data collected by sampling spatial frequency space so that the corresponding Nyquist criterion is not violated). In some embodiments, the data 252 may be under-sampled data (data containing fewer data points than what is required by spatial Nyquist criteria). In some embodiments, the data 252 may be data corresponding to a slice or multiple slices, and may include multiple acquisitions of the same slice or volume so that these acquisitions may be subsequently averaged.

Next, process 250 proceeds to act 254, where one or more MR images are generated from the input MR spatial frequency data. The MR image(s) may be generated using a neural network model (e.g., neural network model 204, described herein with reference to FIG. 2A). In some embodiments, the neural network model may include: a pre-reconstruction neural network (e.g., neural network 210), a reconstruction neural network (212), and a post-reconstruction neural network (214). Example architectures and other aspects of such networks are described herein.

Accordingly, in some embodiments, generating MR image(s) from input MR spatial frequency data at act 254 comprises: (1) processing, at 256, input MR spatial frequency data using a pre-reconstruction neural network (e.g., neural network 210); (2) generating, at 258 and based on output of the pre-reconstruction neural network, at least one initial image of the subject using a reconstruction neural network (e.g. neural network 212); and (3) generating, at 260, at least one MR image of the subject from the at least one initial image of the subject obtained using the reconstruction neural network. The image(s) generated at act 260 may then be saved, sent to another system, displayed, or output in any other suitable way.

It should be appreciated that any of the convolutional neural network models described herein may be two-dimensional or three-dimensional convolutional neural networks that operate on two-dimensional data (e.g., data corresponding to a single image, for example, an image of a slice of a patient's anatomy) or three-dimensional data (e.g., data corresponding to multiple images, for example, a stack of images in a volume each of which corresponds to a respective slice of the patient's anatomy), as aspects of the technology described herein are not limited in this respect.

Example Neural Network Architectures for Generating MR Images from Undersampled Data As described herein, the inventors have developed neural network models for reconstructing MR images from spatial frequency data obtained using non-Cartesian sampling trajectories. For example, as described with reference to FIG. 2A, the reconstruction may be performed by reconstruction neural network 212, in some embodiments. Reconstruction neural network 212 may be implemented in any suitable way including in any of the ways described next with reference to FIGS. 3A-3E and/or in any of the ways described in U.S. Pat. Pub. No.: 2020/0034998, filed Jul. 29, 2019 (as U.S. application Ser. No. 16/524,598), titled "Deep Learning Techniques for Magnetic Resonance Image Reconstruction", which is incorporated by reference in its entirety.

Figure 3A:
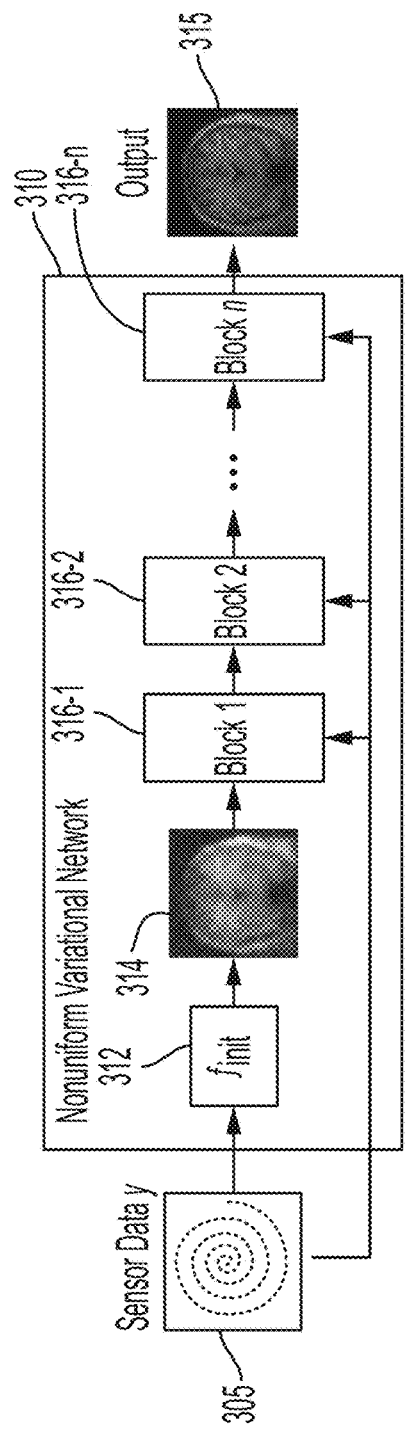
FIG. 3A is a diagram of an illustrative of architecture of an example neural network model for generating MR images from input MR spatial frequency data, in accordance with some embodiments of the technology described herein.

FIG. 3A is a diagram of an illustrative architecture of an example neural network model 310, which generates MR images from input MR spatial frequency data in stages. Input MR spatial frequency data 305 is first processed using initial processing block 312 to produce an initial image 314, and then the initial image 314 is processed by a series of neural network blocks 316-1, 316-2, . . . , 316-n.

In some embodiments, one or more of the blocks 316-1, 316-2, . . . , 316-n may operate in the image domain. In some embodiments, one or more of the blocks 316-1, 316-2, . . . , 316-n may transform the input data to a different domain, including but not limited to the spatial frequency domain, perform processing in the different domain, and subsequently transform back to the image domain.

In some embodiments, the initializer block transforms the input MR spatial frequency data to the image domain to generate an initial image for subsequent processing by the neural network model 310. The initializer block may be implemented in any suitable way, and in some embodiments, the initializer block may employ a Fourier transformation, a non-uniform Fourier transformation, or a gridding reconstruction to obtain the initial image.

Figure 3B:
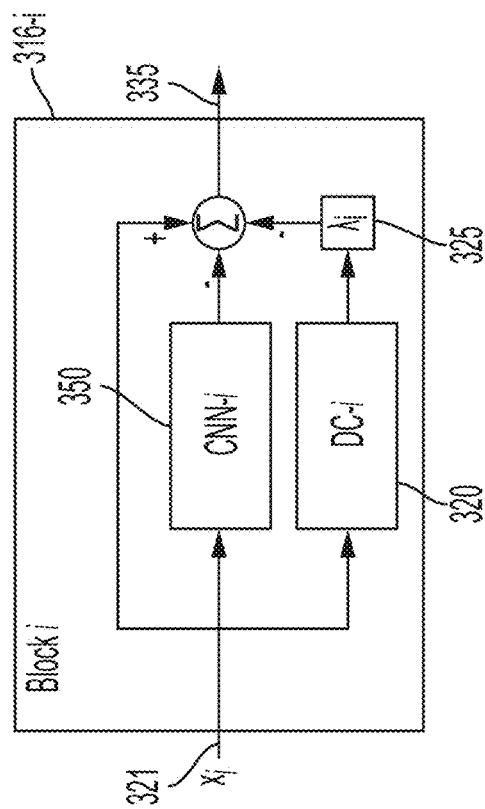
FIG. 3B is a diagram of one type of architecture of a block of the neural network model of FIG. 3A, in accordance with some embodiments of the technology described herein.

In some embodiments, one or more of the blocks 316-1, 316-2, . . . , 316-n may have the architecture of illustrative block 316-i in FIG. 3B, which includes a data consistency block 320, and a convolutional neural network block 350, both of which are applied to the input $x_i$, labeled 321. The input $x_i$ may represent the MR image reconstruction generated by neural network 310 at the completion of the $(i-1)^{st}$ neural network block. The output 335 of the block 316-i is obtained by applying the data consistency block 320 to the input $x_i$, to obtain a first result, applying the convolutional neural network block 350 to $x_i$, to obtain a second result, and subtracting from $x_i$ a linear combination of the first result and the second result, where the linear combination is calculated using the block-specific weight $\lambda_i$.

In some embodiments, the data consistency block 320 may perform data consistency processing by transforming the input image represented by $x_i$ to the spatial frequency domain using a non-uniform Fourier transformation, comparing the result with the initial MR spatial frequency data 305, and transforming the difference between the two back to the image domain using an adjoint of the non-uniform Fourier transformation.

Figure 3C:
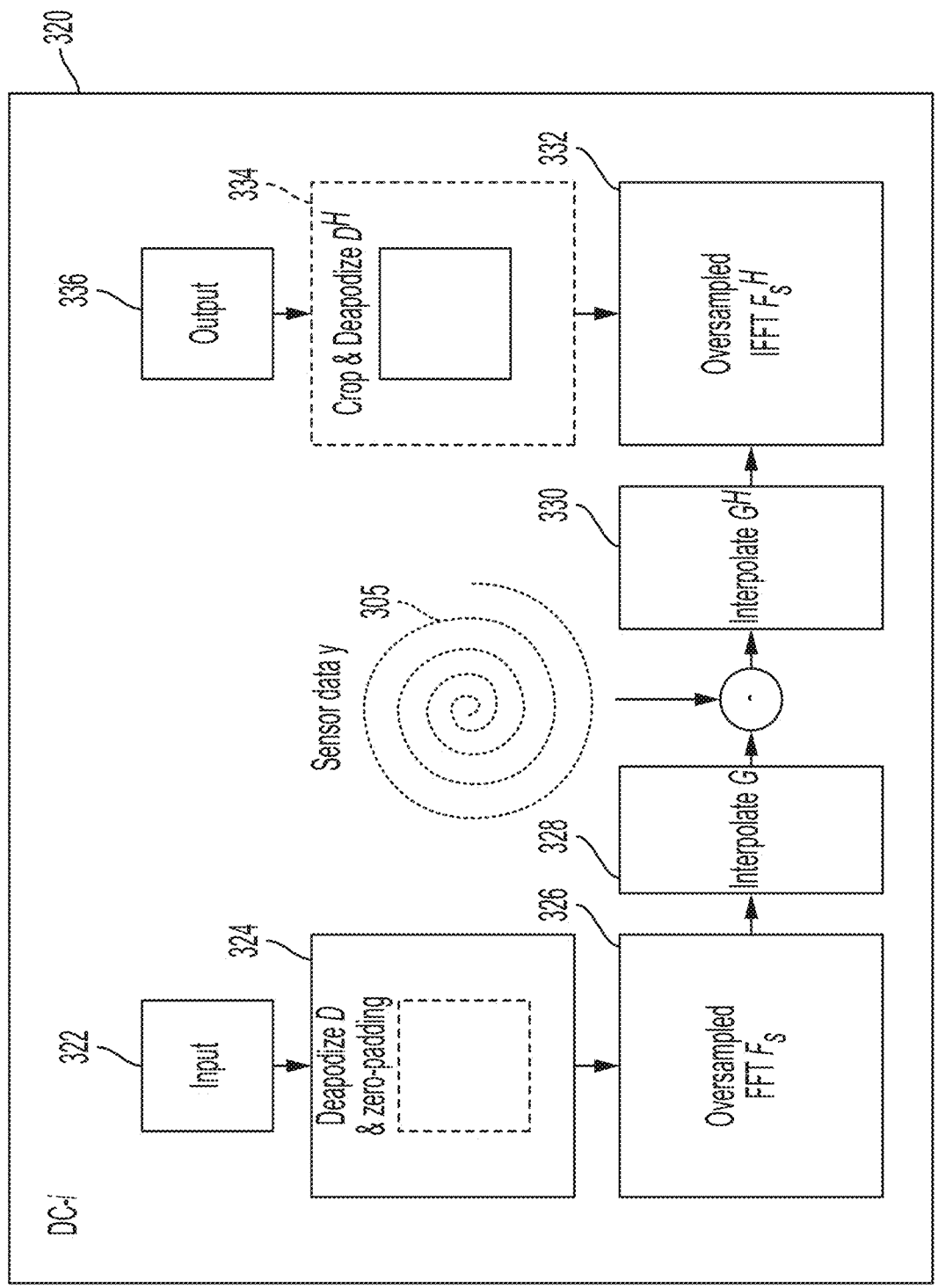
FIG. 3C is a diagram of an illustrative architecture of a data consistency block, which may be part of the block shown in FIG. 3B, in accordance with some embodiments of the technology described herein.

FIG. 3C shows an example implementation of data consistency block 320, in which the image domain input 322, is transformed to the spatial frequency domain through a series of transformations 324, 326, and 328, whose composition is used to implement a non-uniform fast Fourier transformation from the image domain to the spatial frequency domain. The transformation 324 is a de-apodization and zero-padding transformation D, the transformation 326 is an over-sampled FFT transformation $F_s$, and the transformation 328 is the gridding interpolation transformation G. The non-uniform fast Fourier transformation A is represented by the composition of these transformations according to: $A = G F_s D$. Example realizations of these constituent transformations are described herein.

After the image domain input 322 is transformed to the spatial frequency domain, it is compared with the initial MR spatial frequency domain 305, and the difference between the two is transformed back to the image domain using the transformations 330, 332, and 334, in that order. The transformation 330 is the adjoint of the gridding interpolation transformation 328. The transformation 332 is the adjoint of the oversampled FFT transformation 326. The transformation 334 is the adjoint of the de-apodization transformation 324. In this way, the composition of the transformations 330, 332, 334, which may be written as $D^H F_s^H G^H = A^H$, represents the adjoint $A^H$ of the non-uniform Fourier transformation A.

Figure 3D:
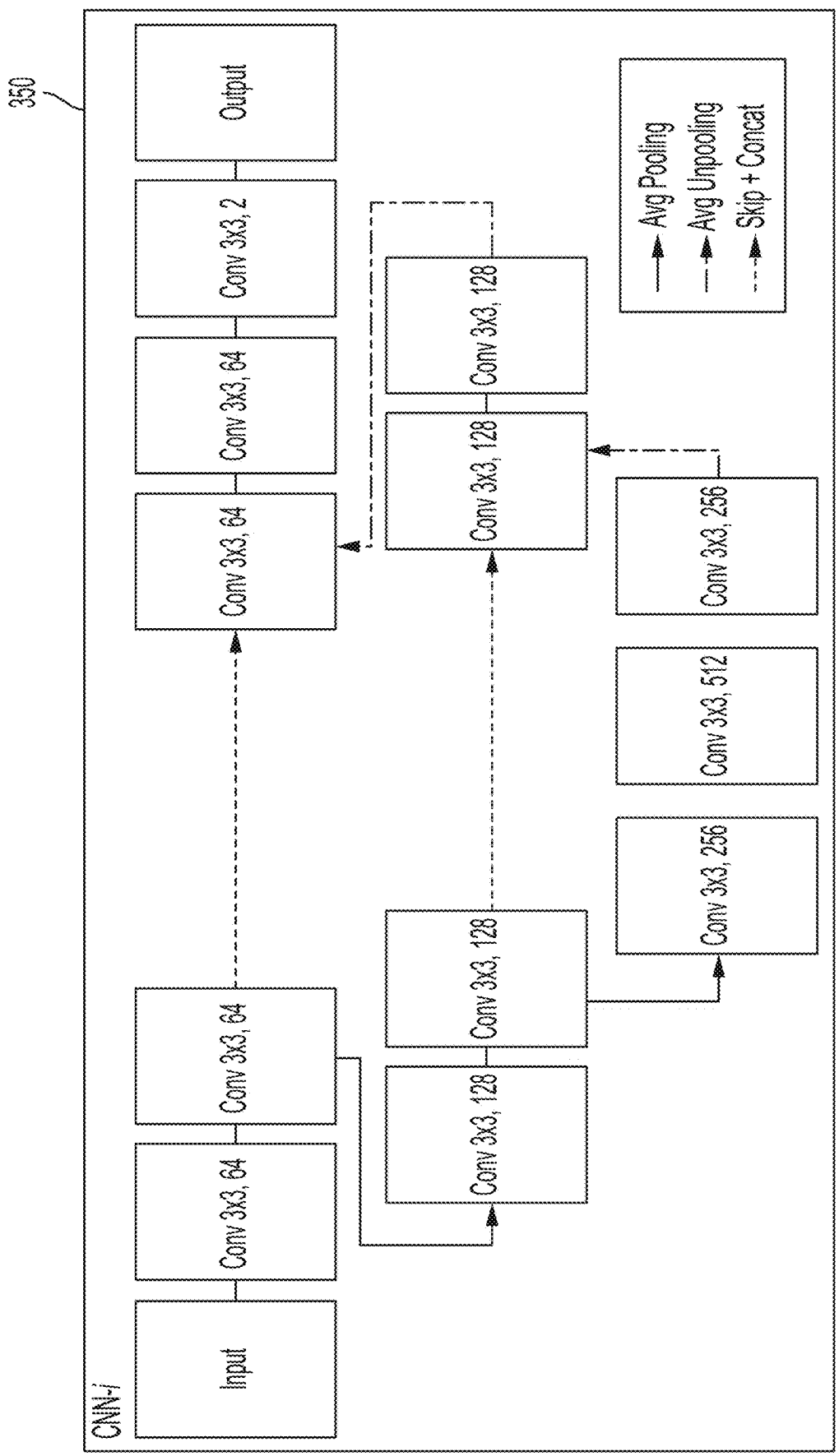
FIG. 3D is a diagram of an illustrative architecture of a convolutional neural network block, which may be part of the block shown in FIG. 3B, in accordance with some embodiments of the technology described herein.

In some embodiments, the convolutional neural network block 350 may have multiple convolutional layers. For example, as shown in FIG. 3D, the block 350 may have a U-net structure, whereby multiple convolutional layers downsample the data and subsequent transpose convolutional layers upsample the data. In the example of FIG. 3D, input to the convolutional network block 350 is processed by a downsampling path followed an upsampling path. In the downsampling path, the input is processed by repeated application of two convolutions with 3×3 kernels, each followed by application of a non-linearity (e.g., a ReLU), an average 2×2 pooling operation with stride 2 for downsampling. At each downsampling step the number of feature channels is doubled from 64 to 128 to 256. In the upsampling path, the data is processed be repeated upsampling of the feature map using an average unpooling step that halves the number of feature channels, a concatenation with the corresponding feature map from the downsampling path, and two 3×3 convolutions, each followed by application of a non-linearity.

Figure 3E:
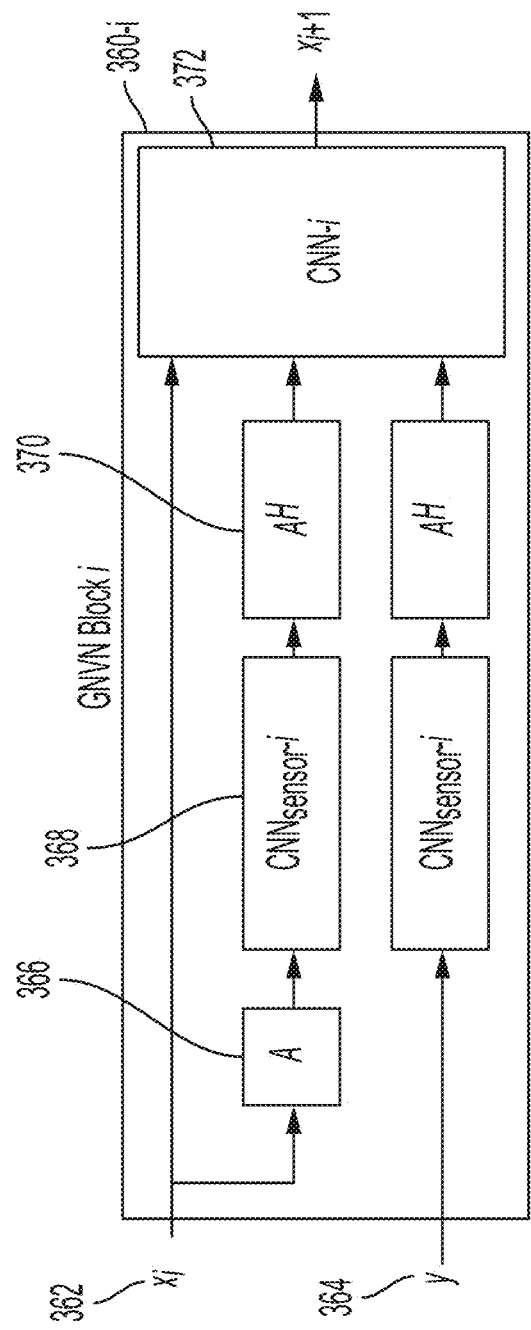
FIG. 3E is a diagram of another type of architecture of a block of the neural network model of FIG. 3A, in accordance with some embodiments of the technology described herein.

FIG. 3E is a diagram of another type of architecture of a block that may be used within the neural network model of FIG. 3A. A neural network model with blocks having the architecture like the one shown in FIG. 3E may be termed a "generalized non-uniform variational network" or "GNVN". It is "generalized" in the sense that, while data consistency blocks are not used directly, features similar to the image features generated by such blocks may be useful to incorporate into a neural network model.

As shown in FIG. 3E, the $i^{th}$ GNVN block 360-$i$ takes as input: (1) the image domain data $x_i$, labeled as 362; and (2) the initial MR spatial frequency data 364. The input $x_i$ may represent the MR image reconstruction generated by neural network 310 at the completion of the $(i-1)^{st}$ GNVN block (360-($i-1$)). These inputs to the block 360-$i$ are used to generate input to the convolutional neural network (CNN) block 372 part of block 360-$i$. In turn, the CNN block 372 generates the next MR image reconstruction denoted by $x_{i+1}$.

In the embodiment of FIG. 3E, the inputs 362 and 364 are used to generate three inputs to the CNN block 372: (1) the reconstruction $x_i$ itself is provided as input to the CNN block; (2) the result of applying, to the reconstruction $x_i$, the non-uniform Fourier transformation 366 followed by a spatial frequency domain CNN 368, followed by the adjoint non-uniform Fourier transformation 370; and (3) the result of applying, to the initial MR spatial frequency data 364, the spatial frequency domain convolutional neural network 368 followed by an adjoint non-uniform Fourier transform 370. The non-uniform Fourier transformation 366 may be the transformation A expressed as a composition of three transformations: the de-apodization transformation D, an oversampled Fourier transformation $F_s$, and a local gridding interpolation transformation G such that $A = G F_s D$. The spatial frequency domain CNN 368 may be a five-layer convolutional neural network with residual connections. In other embodiments, the network 368 may be any other type of neural network (e.g., a fully convolutional network, a recurrent network, and/or any other suitable type of neural network), as aspects of the technology described herein are not limited in this respect.

A discussion of further aspects and details of neural network models for MR image reconstruction from non-Cartesian data, such as the neural network models illustrated in FIGS. 3A-3E, follows next. Let $x \in \mathbb{C}^N$ denote a complex-valued MR image to be reconstructed, represented as a vector with $N = N_x N_y$, where $N_x$ and $N_y$ are width and height of the image. Let $y \in \mathbb{C}^M$ ($M \ll N$) represent the under-sampled k-space measurements from which the complex-valued MR image x is to be reconstructed. Reconstructing x from y may be formulated as an unconstrained optimization problem according to:

$$\underset{x}{\operatorname{argmin}} \frac{\lambda}{2} \|Ax - y\|_2^2 + \mathcal{R}(x), \qquad \text{(Eq. 1)}$$

where the operator A is a non-uniform Fourier sampling operator, $\mathcal{R}$ expresses regularisation terms on x, and $\lambda$ is a hyper-parameter associated to the noise level. When the k-space measurements y are obtained using a Cartesian sampling trajectory, the operator A may expressed according to: $A = MF$ where M is a sampling mask, and F is discrete Fourier transform. In the case of a non-Cartesian sampling trajectory, the measurements no longer fall on a uniform k-space grid and the sampling operator A is now given by a non-uniform discrete Fourier transform of type I:

$$y((k_x, k_y)) = \sum_{l=0}^{N_x} \sum_{m=0}^{N_y} x_{lm} e^{2\pi i \left(\frac{l}{N_x} k_x + \frac{m}{N_y} k_y\right)} \qquad \text{(Eq. 2)}$$

where $(k_x, k_y) \in \mathbb{R}^2$ (rather than $(k_x, k_y) \in \mathbb{Z}^2$). An efficient implementation of the above forward model may be implemented using the so-called non-uniform Fast Fourier Transform (NUFFT), whereby Eq. 2 is approximated by the decomposition: $A = GF_s D$, where G is a gridding interpolation kernel, $F_s$ is fast Fourier transform (FFT) with an oversampling factor of s, and D represents a de-apodization weights.

Inversion of A is more involved. For the (approximately) fully-sampled case, one can consider direct inversion ($\mathcal{O}(N^3)$) or a more computationally efficient gridding reconstruction, which has the form $x_{gridding}=A^H Wy$, where W is a diagonal matrix used for the density compensation of non-uniformly spaced measurements. For the undersampled case, the inversion is ill-posed, and Eq. 1 should be solved by iterative algorithms.

The inventors have developed a new deep learning algorithm to approximate the solution to the optimization problem of Eq. 1. The approach begins by considering a gradient descent algorithm, which provides a locally optimal solution to Eq. 1, specified by the following equations for initialization and subsequent iterations:

$$x_0 = f_{init}(A,y); \quad \text{(Eq. 3)}$$

$$x_{i+1} = x_i - \alpha_i \nabla_x f(x)_{x=x_i}, \quad \text{(Eq. 4)}$$

where $f_{init}$ is an initializer, $\alpha$ is a step size and $\nabla f$ is the gradient of the objective functional, which is given by:

$$\nabla_x f(x) = \lambda A^H(Ax - y) + \nabla_x \mathcal{R}(x). \quad \text{(Eq. 5)}$$

In some embodiments, the initializer may be the adjoint $f_{init}(A,y) = A^H y$ reconstruction or the gridding reconstruction $f_{init}(A,y) = A^H Wy$. The deep learning approach to solving Eq. 1 involves unrolling the sequential updates of Eq. 4 into a feed-forward model, and approximating the gradient term $\nabla \mathcal{R}$ by a series of trainable convolutional (or other types of neural network) layers and non-linearities. This approach results in an end-to-end trainable network with $N_{it}$ blocks given by:

$$x_0 = f_{init-cnn}(A, y | \theta_0) \quad \text{(Eq. 6)}$$

$$x_{i+1} = x_i - \underbrace{\lambda_i A^H(Ax_i - y)}_{DC-i} - \underbrace{f_{cnn}(x_i | \theta_i)}_{CNN-i} \quad \text{(Eq. 7)}$$

where the learnable parameters are $\{\theta_0, \ldots, \theta_{N_{it}}, \lambda_1, \ldots, \lambda_{N_{it}}\}$. The step size $\alpha_i$ may be absorbed in the learnable parameters. In this way, a general non-convex regularization functional is used, which may be approximated by convolutional neural networks. For example, the neural network models of FIGS. 3A-3D may implemented based on Equations 6 and 7. For example, the data consistency term DC-i in Eq. 6 may be implemented as shown in FIG. 3C, and the CNN-i term in Eq. 6 may be implemented is shown in FIG. 3D.

Further details of the decomposition of the forward operator $A=GF_sD$ are described next. The spatial frequency domain may be indexed using two-dimensional or three-dimensional coordinates (e.g. ($k_x$, $k_y$) or ($k_x$, $k_y$, $k_z$)). Each entry of the vector y representing input MR spatial frequency data represents a value associated to a specific k-space coordinate. A regular grid in k-space refers to a regularly-spaced grid of points k-space such that there is a fixed distance $\Delta$ between each k-space coordinate that can be indexed. Generally, the input MR spatial frequency data y may include k-space samples spaced on a regular-grid or irregularly spaced. Regularly spaced points are sometimes termed Cartesian data points. Irregularly spaced points are sometimes termed non-Cartesian (data) points.

The interpolation transformation G operates to interpolate non-Cartesian sensor data y onto a regular k-space grid. When the transformation is represented as a matrix G, each row in the matrix corresponds to a specific regular grid point in k-space, and the entry j in the row i (i.e., the entry $G_{ij}$) expresses how much weight is associated between ith regular grid and jth k-space sample. In some embodiments, the interpolation matrix entries may be computed using any one of the following four functions:

- Two term cosine $\alpha + (1-\alpha)\cos\left(\frac{2\pi}{W}u\right)$
- Three-term cosine: $\alpha + \beta\cos\left(\frac{2\pi}{W}u\right) + (1-\alpha-\beta)\cos\left(\frac{4\pi}{W}u\right)$
- Gaussian: $\exp\left[-\frac{1}{2}\left(\frac{u}{\sigma}\right)^2\right]$
- Kaiser-Bessel $\frac{1}{W}I_0\left[\beta\sqrt{1-(2u/W)^2}\right]$ where u is a distance between ith regular grid point and jth non-Cartesian data coordinate. The parameters $\alpha$, $\beta$, W, $\sigma$ are free design parameters to be specified by user, and $I_0$ is the zeroth-order modified Bessel function of the first kind. Other functions may be used to compute interpolation matrix entries instead of or in addition to the above example functions.

In some embodiments, the Fourier transformation F may be represented by an oversampled Fourier matrix $F_s$, which is a dense matrix in which each entry is a complex exponential of the form $e^{i\gamma}$ for $\gamma$ which depends on the index. The role of this matrix is to perform Fourier transform. In some embodiments, $F_s$ may be implemented using the fast Fourier transform with oversampling factor s. For example, if the image to be reconstructed x is N×N pixels, then oversampling FFT is performed for image size sN×sN.

In some embodiments, the de-apodization transformation may be represented by a matrix D that will weigh each pixel in the image by a corresponding weight to reduce the interpolation error of approximating A with the given decomposition. In some embodiments, this may be implemented via a pixel-wise weighting of the intermediate reconstruction in the image domain. For example, the pixel-wise weighting may be implemented using a spatially-varying low-order smooth polynomial. In some embodiments, the matrix D may be set as described in Section IV-C of Fessler, J. A., Sutton B. P.: Non-uniform fast Fourier transforms using min-max interpolation. IEEE Transactions of Signal Processing 51(2), 560-574 (2003), which is incorporated by reference in its entirety.

The neural network architectures described herein with reference to FIGS. 3A-3D, may be considered as embodiments of a more general neural network model that may be expressed according to the following:

$$x_{rec} = f_{rec}(A, y | \theta) \quad \text{(Eq. 8)},$$

which accepts as input any input that is a combination of the forward operator A and raw spatial frequency data y. The learnable parameters $\theta$ may be adjusted during training process.

The input to the neural network of Eq. 8 may be data obtained by one or multiple RF coils of an MRI system. The input data y may have been obtained using multiple contrasts and/or different sets of acquisition parameters (e.g., by varying repetition time (TR), echo time (TE), flip angle $\theta$, etc.). In some embodiments, input into the network may be, but is not limited to, the raw data y. Additionally or alternatively, the input to the network may be the adjoint reconstruction $A^H y$ where $(\cdot)^H$ is the conjugate transpose of the matrix.

In some embodiments, where the data y includes data collected by multiple RF coils, these data y may be split into $N_{coil}$ separate data sets, denoted $y^{(i)}$ for $i=1, \ldots, N_{coil}$. In some such embodiments, the neural network input may be the adjoint reconstruction of each coil images $x_0^{(1)} = A^H y^{(1)}$, and $x_0^{(1)}$ for $i=1, \ldots, N_{coil}$ can be stacked together and form the input to the network (e.g., to the convolutional layers part of the network).

In some embodiments, the raw data y may include multiple measurements obtained by each of one or more RF coils. For example, if the data is measured multiple times, say $N_{avg}$ times, then these data, or the adjoint reconstruction of these data, or any other function of these data measurements and the forward operator A, may form an input to the neural network. For example, multiple measurements may be obtained for signal averaging and/or as part of acquiring images with different contrast.

It should also be appreciated that the neural network of Eq. 8 need not operate on the raw data y, and in some embodiments these data may be pre-processed. For example, in some embodiments these data may be pre-processed to perform operations such as interference removal, denoising, filtering, smoothing, image prewhitening, etc. The output $x_{rec}$ of the neural network in Eq. 8, the output may include one or more images per respective RF coil. For example, if the input data contains data from each of $N_{coil}$ RF coils, the output may include one MR image for each such RF coil or multiple MR images for each such coil (e.g., when each coil performs multiple acquisitions, for example, using different contrasts).

Example Neural Network Architectures for Pre-Reconstruction Artefact Suppression As described above with reference to FIG. 2B, pre-reconstruction neural network 210 may be configured to suppress various types of artefacts in the MR spatial frequency data. The suppression may involve rejecting lines of collected data (e.g., using neural network 220), suppressing RF interference (e.g., using neural network 224), and/or suppressing noise (e.g., using neural network 226). The neural networks 224 and/or 226 may be implemented in any suitable way including in any of the ways described next with reference to FIGS. 4A-4D and/or in any of the ways described in U.S. Pat. Pub. No.: 2020/0058106, filed Aug. 15, 2019 (as U.S. application Ser. No. 16/541,511), titled "Deep Learning Techniques for Suppressing Artefacts in Magnetic Resonance Images," which is incorporated by reference in its entirety. As yet another example, the neural networks 224 and/or 26 may be implemented using one or more other architectures such as, for example, a ResNet architecture comprising convolutional blocks with residual connections, as described in He K, Zhang X, Ren S, Sun J. "Deep residual learning for image recognition." In Proceedings of the IEEE conference on computer vision and pattern recognition 2016 (pp. 770-778), which is incorporated by reference in its entirety.

In some embodiments, the neural network 224 for suppressing RF interference may be implemented as a neural network having a "U" structure with convolutional layers being first applied to a sequence of successively lower-resolution versions of the data (along the down-sampling path) and, second, to a sequence of successively higher-resolution versions of the data (along the up-sampling path). An example of such an architecture is shown in FIG. 4A as architecture 430.

Figure 4A:
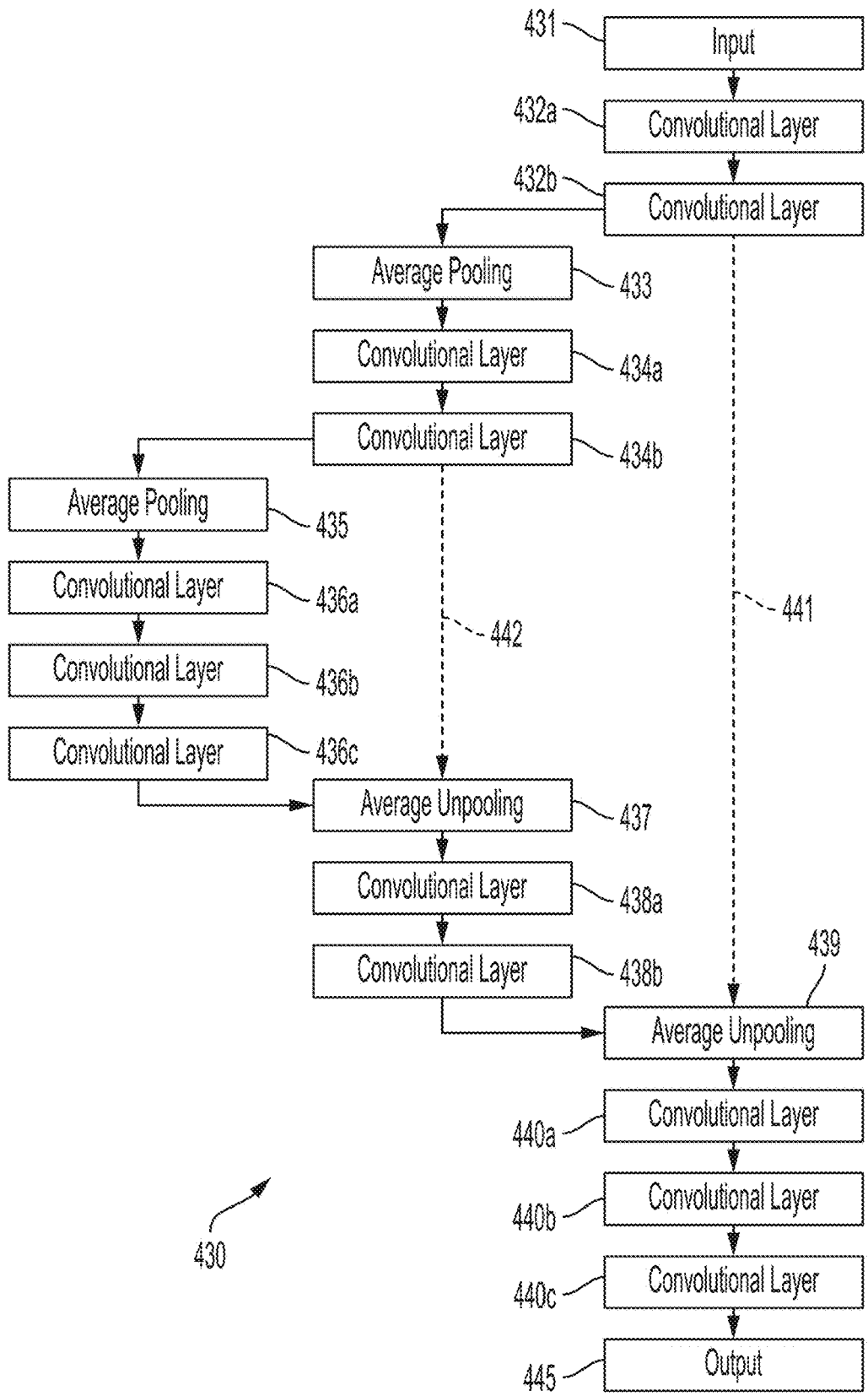
FIG. 4A illustrates the architecture of an example convolutional neural network block having a "U" structure and an average pooling layer, which block may be part of the pre-reconstruction neural network model, in accordance with some embodiments of the technology described herein.

As shown in FIG. 4A, in the down-sampling path, convolutional layers 432a and 432b are applied to input 431. An average pooling layer 433 is then applied to the output of convolutional layer 432b, and convolutional layers 434a and 434b are applied to the lower-resolution data produced by the average pooling layer 433. Next, another average pooling layer 435 is applied to the output of convolutional layer 434b, and convolutional layers 436a, 436b, and 436c are applied to the output of the average pooling layer 435.

Next, in the up-sampling path, the output of convolutional layer 436c is processed by the average unpooling layer 437. The output of the average unpooling layer 437 is processed by convolutional layers 438a and 438b. The output of convolutional layer 438b is processed by average unpooling layer 439, and the output of average unpooling layer 439 is processed by convolutional layers 440a-c to generate output 445.

The architecture 430 also includes skip connections 441 and 442, which indicates that the input to the average unpooling layers consists from output by the immediately preceding convolutional layer and output having a higher resolution generated by another (not immediately) preceding convolutional layer. For example, the input to the average unpooling layer 437 is the output of convolutional layers 434b (as indicated by the skip connection 442) and 436c. The output of convolutional layer 434b has a higher resolution than that of layer 436c. As another example, the input to the average unpooling layer 439 is the output of convolutional layers 432b (as indicated by the skip connection 442) and 438b. The output of convolutional layer 432b has a higher resolution than that of layer 438b. In this way, high frequency information that is lost through the application of pooling layers along the down-sampling path is re-introduced (and not lost) as input to the unpooling layers along the up-sampling path. Although not expressly shown in FIG. 4A, a non-linearity layer (e.g., a rectified linear unit or ReLU, sigmoid, etc.) may be applied after one or more (e.g., convolutional) layers shown in the architecture 430. In addition, batch normalization may be applied at one or more points along the architecture 430 (e.g., at the input layer).

Figure 4B:
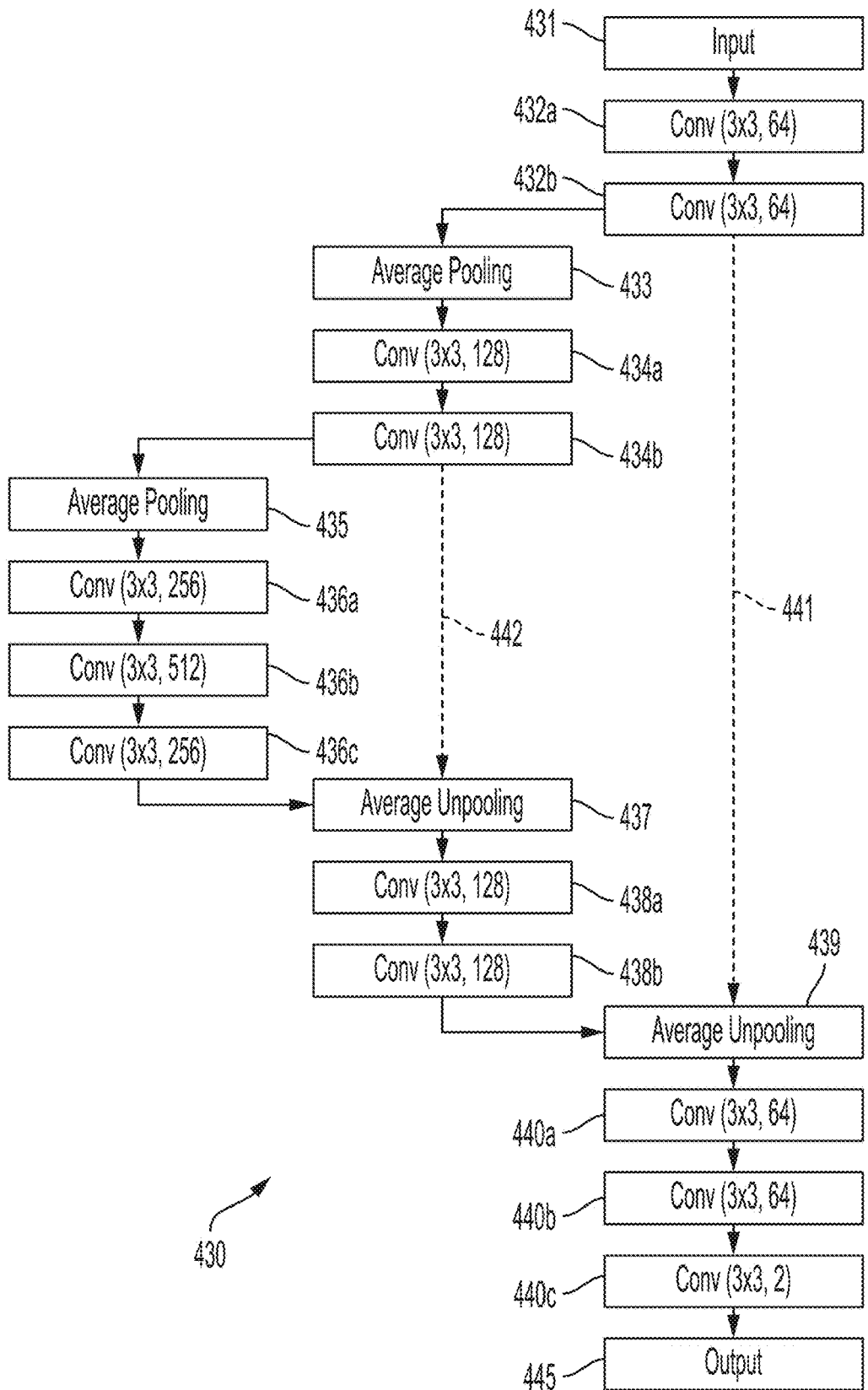
FIG. 4B illustrates a specific example of the architecture of an example convolutional neural network block shown in FIG. 4A, in accordance with some embodiments of the technology described herein.

FIG. 4B illustrates a specific example of the architecture of the neural network shown in FIG. 4A. As shown in FIG. 4B, all of the convolutional layers apply a 3×3 kernel. In the down-sampling path, the input at each level is processed by repeated application of two (or three at the bottom level) convolutions with 3×3 kernels, each followed by an application of a non-linearity, an average 2×2 pooling operation with stride 2 for down-sampling. At each down-sampling step the number of feature channels is doubled from 64 to 128 to 256. The number of feature channels is also doubled from 256 to 512 at the bottom layer. In the up-sampling path, the data is processed by repeated up-sampling of the feature maps using an average unpooling step that halves the number of feature channels (e.g., from 256 to 128 to 64), concatenating with the corresponding feature map from the down-sampling path and one or more convolutional layers (using 3×3 kernels), each followed by application of a non-linearity. The last convolutional layer 440c reduces the number of feature maps to 2.

Figure 4C:
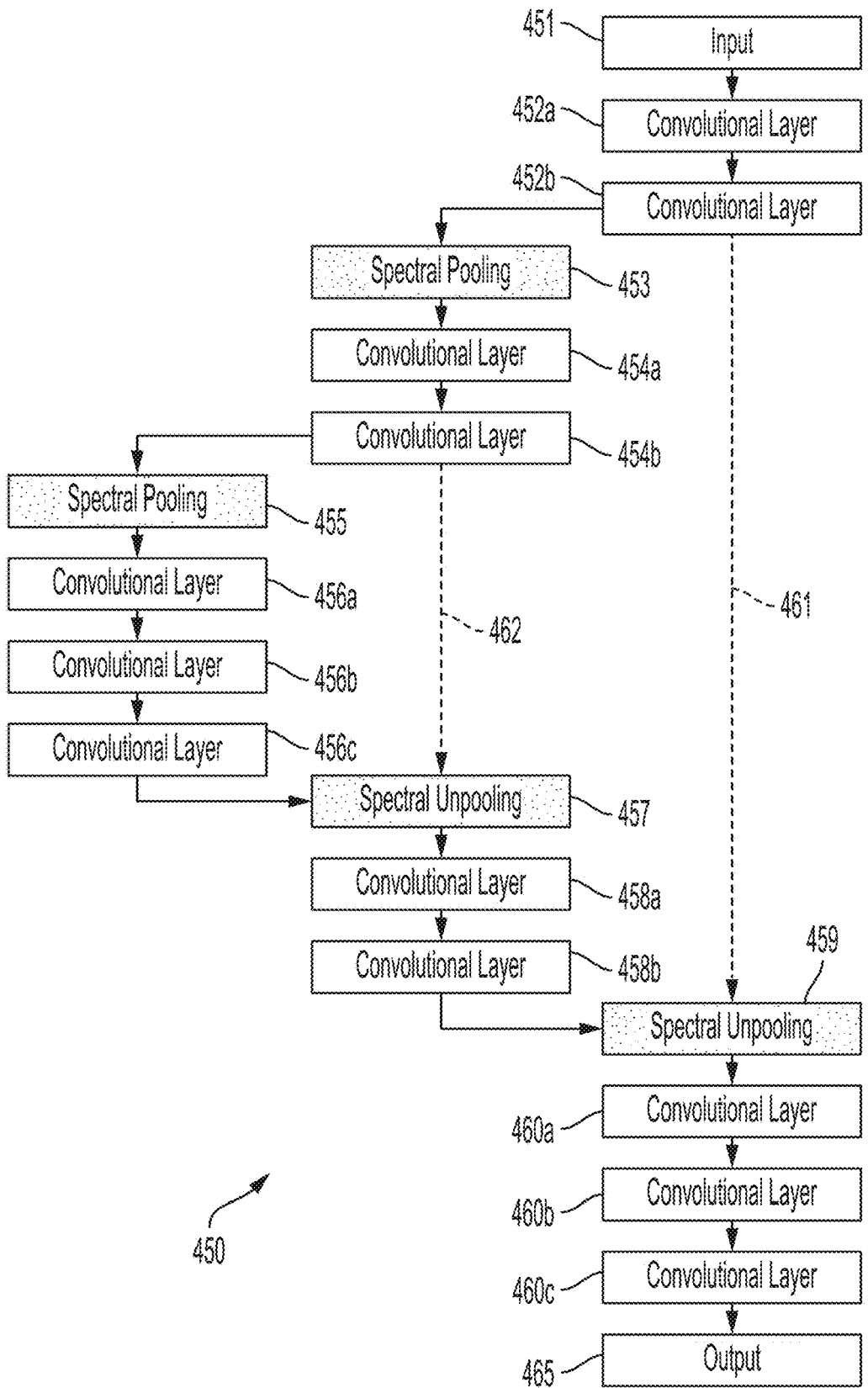
FIG. 4C illustrates the architecture of an example convolutional neural network block having a "U" structure and a spectral unpooling layer, which block may be part of the pre-reconstruction neural network model, in accordance with some embodiments of the technology described herein.

In some embodiments, a neural network for suppressing RF interference or noise may include "spectral pooling" and "spectral unpooling" layers, as shown, for example, in FIG. 4C that illustrates the architecture 450 of a CNN having a "U" structure and spectral pooling and unpooling layers instead of the average pooling and unpooling layers.

As shown in FIG. 4C, in the down-sampling path, convolutional layers 452a and 452b are applied to input 451. A spectral pooling layer 453 is then applied to the output of convolutional layer 452b, and convolutional layers 454a and 454b are applied to the lower-resolution data produced by the spectral pooling layer 453. Another spectral pooling step 455 is applied to the output of convolutional layer 454b, and convolutional layers 436a, 436b, and 436c are applied to the output of spectral pooling layer 455. In the up-sampling path, the output of convolutional layer 456c is processed by the spectral unpooling layer 457 whose output is in turn processed by convolutional layers 458a and 458b. The output of convolutional layer 458b is processed by spectral unpooling layer 459, whose output is processed by convolutional layers 460a-c to generate output 465. A spectral pooling layer may be implemented by simply removing higher spatial frequency content from the data, which may be implemented efficiently since the data may be already in the spatial frequency domain, and a Discrete Fourier Transform (DFT) is not needed.

The architecture 450 also includes skip connections 461 and 462. Thus, the input to spectral unpooling layer 457 is the output of convolutional layers 454b and 456c (with the output of layer 454b including higher frequency content than the output of layer 456c). The input to spectral unpooling layer 459 is the output of layers 452b and 458b (with output of layer 452b including higher frequency content than output of layer 458b).

The architecture 450 may be implemented in a manner analogous to that of architecture 430 in FIG. 4B. For example, 3×3 kernels may be used and the number of feature channels may increase from 64 to 128 to 256 to 512 along the down-sampling path and decrease from 512 to 256 to 128 to 64 and to 2 along the up-sampling path. However, any other suitable implementation (e.g., number of feature channels, kernel size, etc.) may be used, as aspects of the technology described herein are not limited in this respect.

Figure 4D:
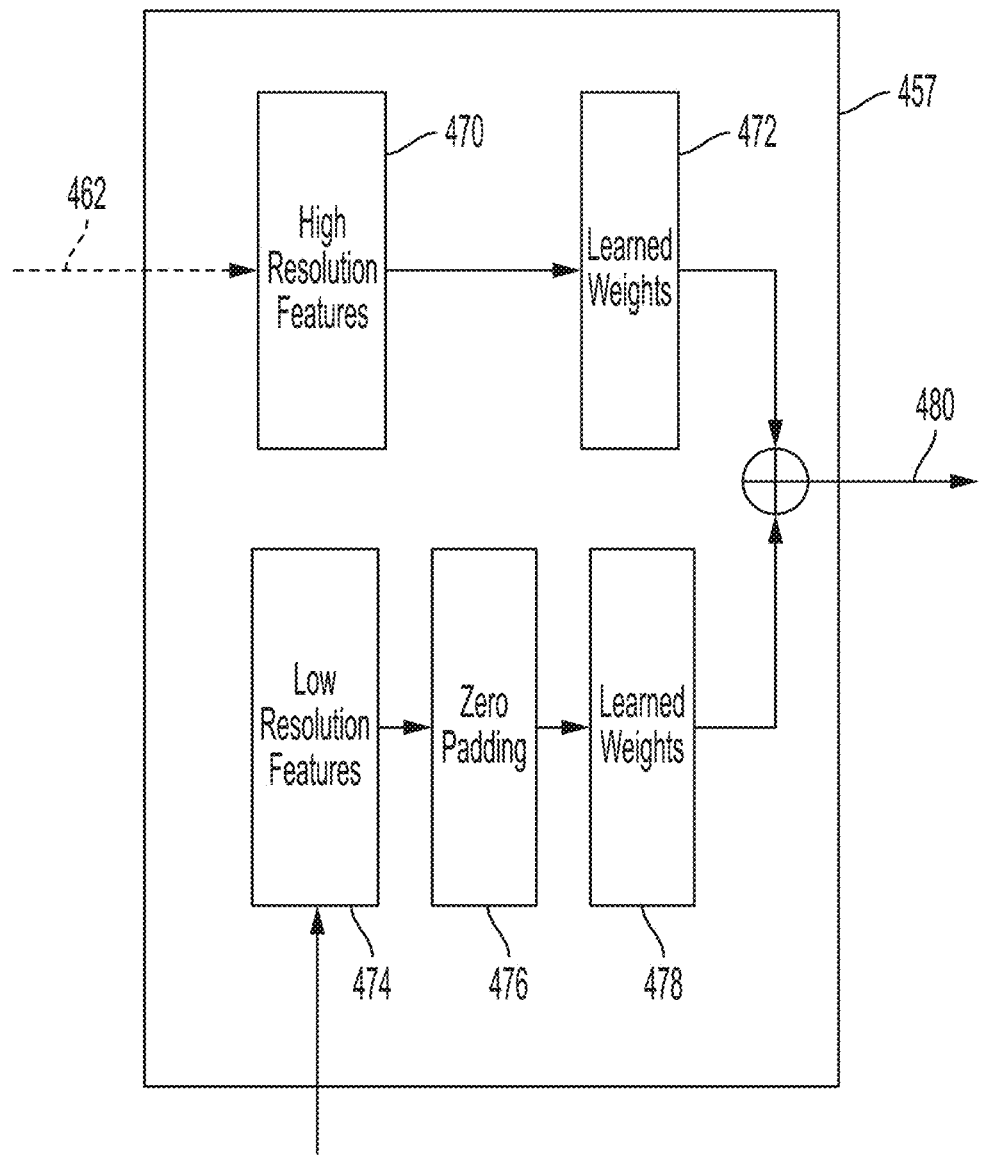
FIG. 4D illustrates the architecture of an example spectral unpooling layer, in accordance with some embodiments of the technology described herein.

FIG. 4D illustrates an example architecture of spectral unpooling layer 457 part of architecture 450. In FIG. 4D, the output 480 of spectral unpooling layer 457 is generated from two inputs: (1) high resolution features 470 provided via skip connection 462 (from output of convolutional layer 452b); and (2) low resolution features 474 provided as output from convolutional layer 458b. The high resolution features 470 include higher (spatial) frequency content than the low resolution features 474. As one specific example, the low-resolution features 474 may include one or more (e.g., 128) feature channels each comprising 64×64 complex values and the high-resolution features may include one or more (e.g., 64) feature channels each comprising 128×128 complex values. A high-resolution 128×128 feature channel and a corresponding low-resolution 64×64 feature channel may be combined by: (1) zero padding the 64×64 feature channel to obtain a 128×128 zero-padded set of values; and (2) adding the high resolution 128×128 feature channel (weighted by weights 472) to the 128×128 zero-padded set of values (weighted by weights 478).

In the illustrated embodiment, the spectral unpooling layer 457 combines the high resolution features and low resolution features 474 by: (1) zero padding the low resolution features 474 using zero padding block 476; and (2) computing a weighted combination of the zero-padded low-resolution features (weighted using weights 478) with the high resolution features (weighted by weights 472). In some embodiments, the weights 472 and 478 may be set manually, in others they may be learned from data.

The neural networks 220, 224, and 226 may be implemented in any suitable domain. For example, in some embodiments, each of one or more of these networks may be applied in the sensor domain, spectral domain, log spectral domain, time domain, spatial frequency domain, wavelet domain, and/or any other suitable domain, as aspects of the technology described herein are not limited in this respect.

Neural Network Training

The neural network models described herein may be trained using any suitable neural network training algorithm(s), as aspects of the technology described herein are not limited in this respect. For example, in some embodiments, the neural network models described herein may be trained by using one or more iterative optimization techniques to estimate neural network parameters from training data. For example, in some embodiments, one or more of the following optimization techniques may be used: stochastic gradient descent (SGD), mini-batch gradient descent, momentum SGD, Nesterov accelerated gradient, Adagrad, Adadelta, RMSprop, Adaptive Moment Estimation (Adam), AdaMax, Nesterov-accelerated Adaptive Moment Estimation (Nadam), and AMSGrad.

In some embodiments, training data for training a neural network may be generated synthetically from available MR images. In particular, in some embodiments, magnitude MR images (phase information is typically discarded) may be used to generate corresponding spatial frequency data and the resulting (spatial frequency data, MR image) pairs may be used to train a neural network model, including any of the neural network models described herein, for example, by using any of the above-described algorithms.

In some embodiments, the process of synthesizing spatial frequency data from MR image data for training a neural network may take into account one or more characteristics of MRI system that will collect patient data that the neural network is being trained to process once the neural network is deployed. Non-limiting, examples of such characteristics include, but are not limited to, size of the field of view of the MRI system, sampling patterns to be used by the MRI system during imaging (examples of various sampling patterns are provided herein), number of RF coils in the MRI system configured to detect MR data, geometry and sensitivity of RF coils in the MRI system, pulse correlation among signals received by the RF coils of the MRI system, RF interference (external and internal) that the MRI system is expected to experience during operation, RF noise (e.g., from the MR signal receive chain) that the MRI system is expected to experience during operation, pulse sequences to be used during imaging, and field strength of the MRI system.

Using characteristics of the MRI system that will collect patient data to generate training data allows for the neural network to learn these characteristics and use them to improve its performance on tasks in the reconstruction pipeline. Moreover, this approach allows the trained neural network models to reconstruct MR images of comparably high quality based on sensor data acquired using MRI hardware and software that produces comparatively lower quality sensor measurements due to various hardware and software characteristics (including constraints and imperfections).

Figure 5A:
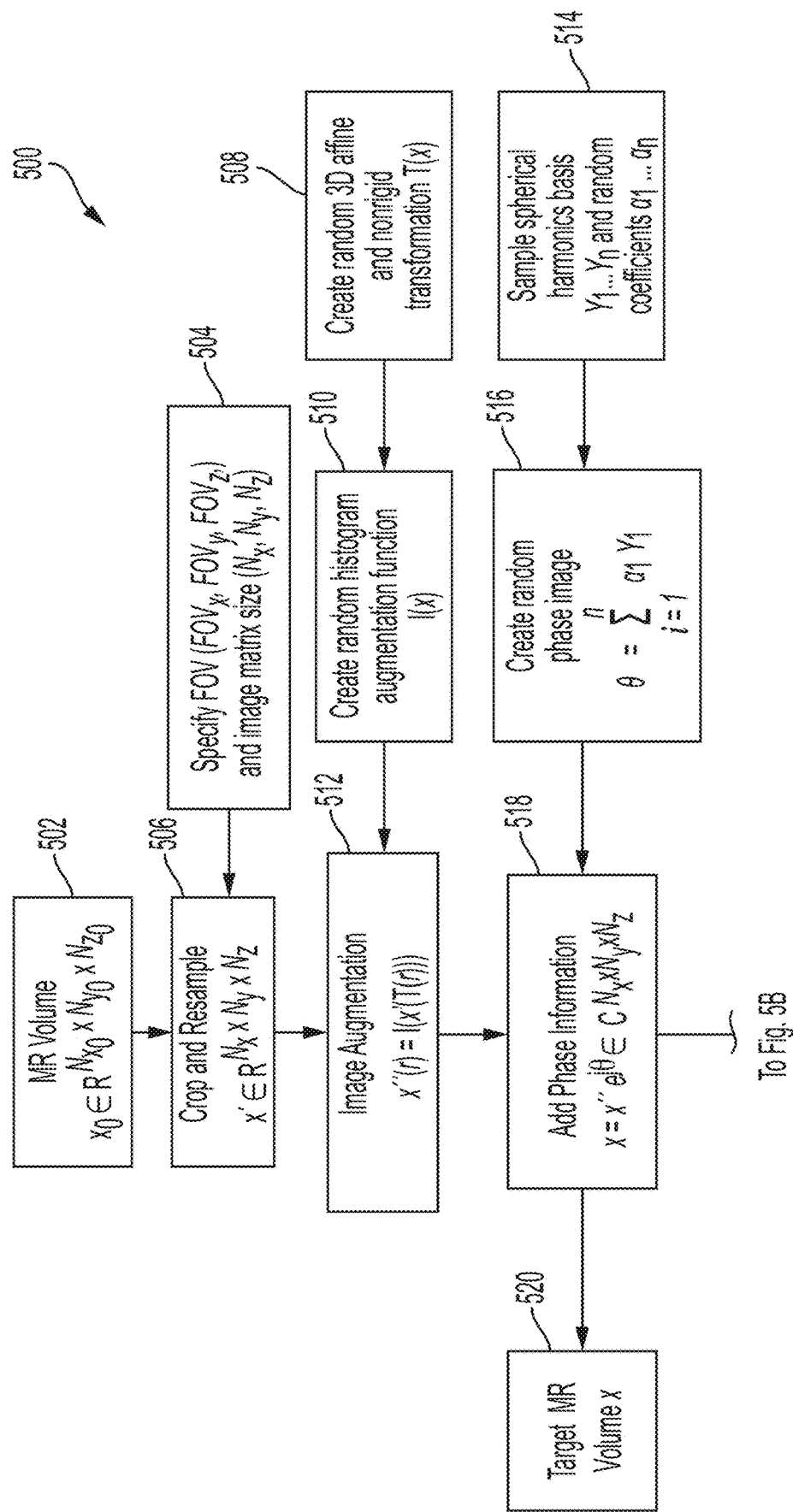
FIGS. 5A-5C show an illustrative diagram of a process for generating training data from MR images for training the neural network models described herein, in accordance with some embodiments of the technology described herein.
Figure 5B:
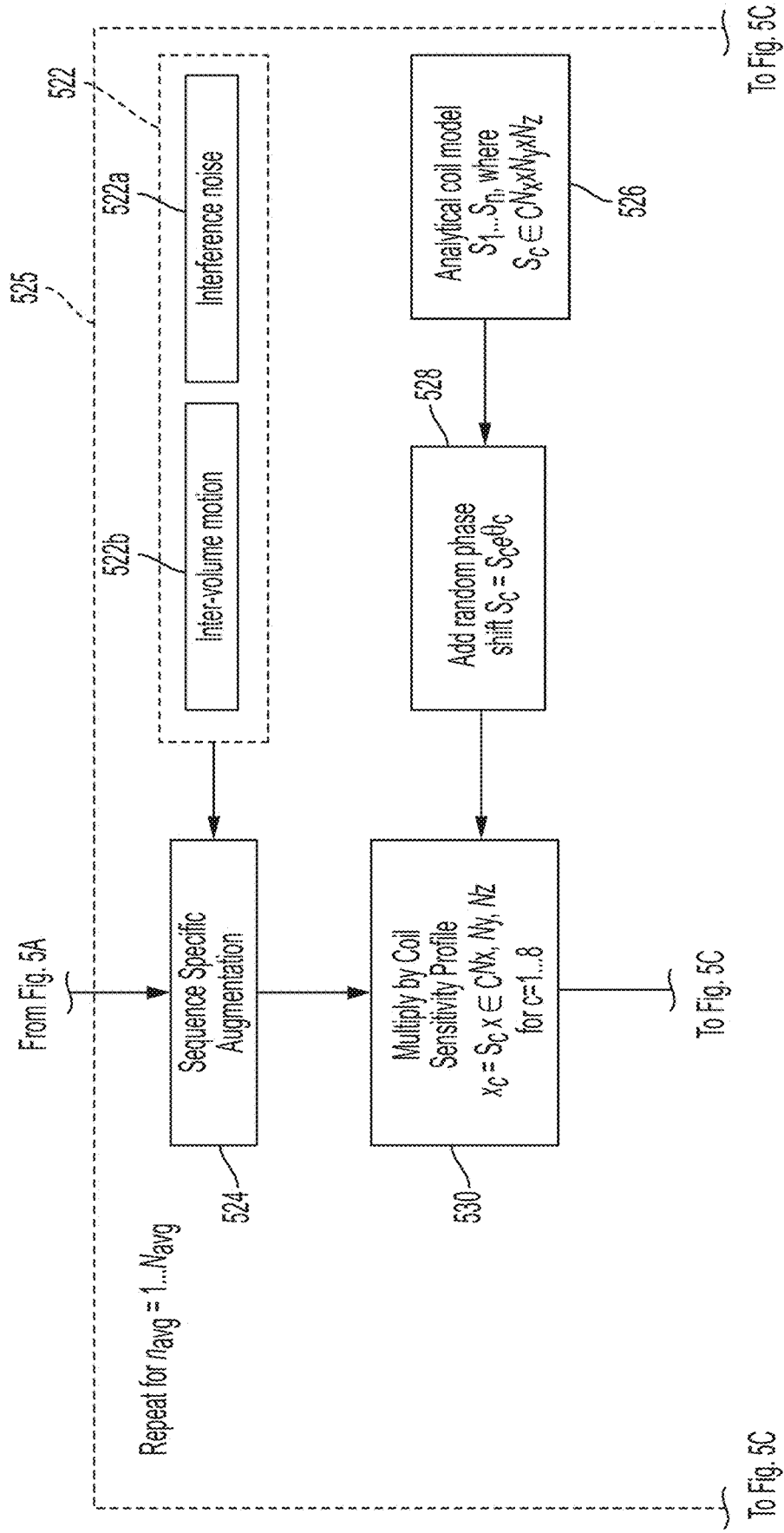
Figure 5C:
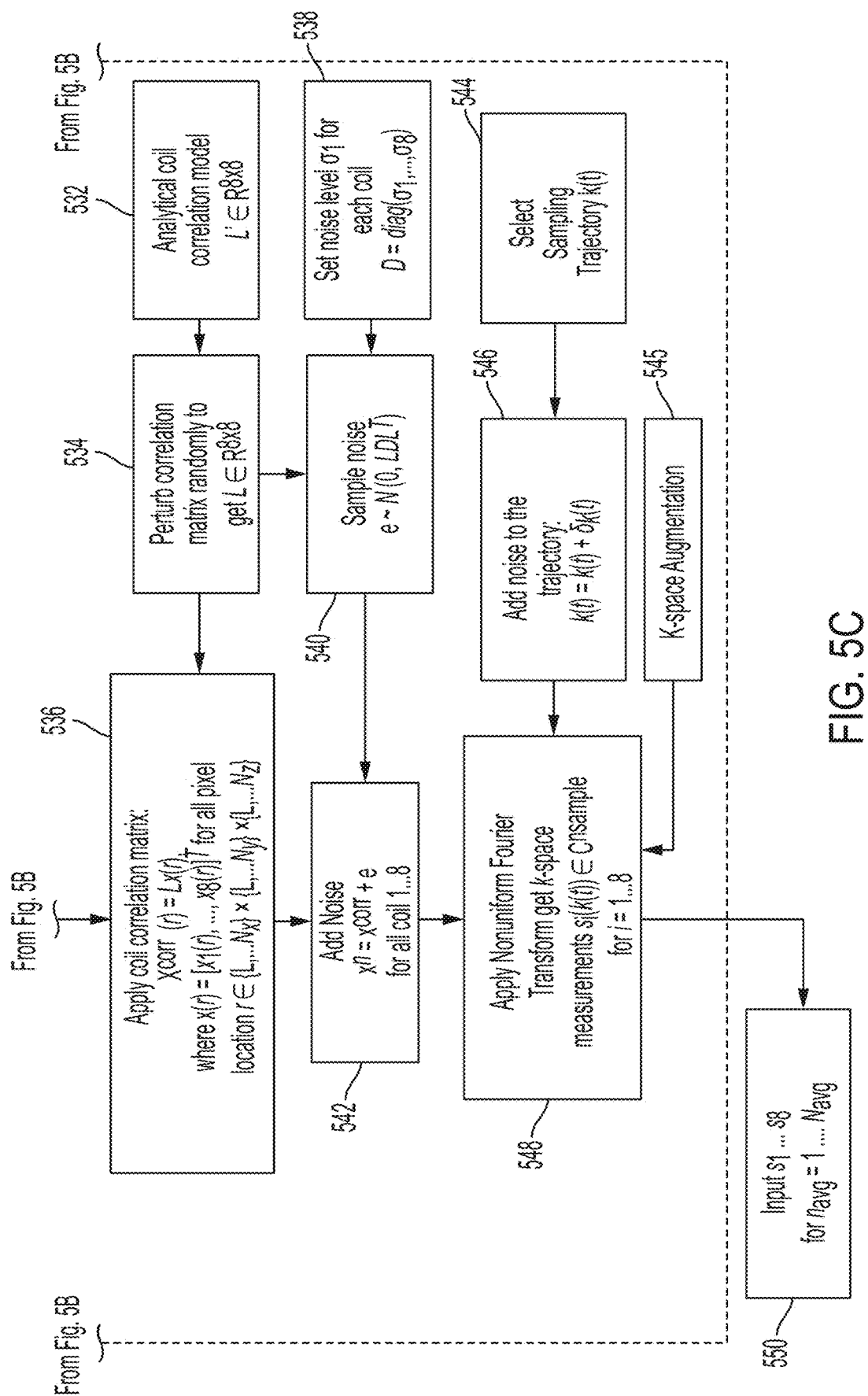

FIGS. 5A-5C show an illustrative diagram of a process 500 for generating training data from MR images for training the neural network models described herein, in accordance with some embodiments of the technology described herein. The process 500 starts with a magnitude MR volume 502 using various specified characteristics of an MRI system generates spatial frequency data 550, which includes spatial frequency data collected multiple times ($N_{avg}$ times in this example) by each of multiple RF cols of the MRI system (8 in this example). Process 500 may be performed by any suitable computing device(s) and, in some embodiments, may be performed in a cloud computing environment, for example.

In some embodiments, process 500 may be repeated multiple times by starting from the same MR volume 502 to generate different spatial frequency data 550, since multiple portions of the process 500 can be made to vary across different runs since these portions sample certain variations and parameters at random. Repeating process 500 multiple times by starting from the same MR volume, but varying the process parameters (e.g., transformations applied to the image at acts 508, 510, and 512) enables the generation of multiple training data pairs from a single MR volume, which is a type of data augmentation that not only increases the diversity and coverage of the training data, but also reduces the demand to obtain greater amounts of real-world MRI images needed for training, which can be expensive, time-consuming, and impractical.

As shown in FIGS. 5A-5C, process 500 begins by accessing a reference magnitude MR volume 502. The MR volume 502 may comprise one or multiple images. Each of the image(s) may represent an anatomical slice of a subject being imaged. The MR volume 502 may include one or more magnitude images obtained by a clinical MRI system. In some embodiments, for example, the MR volume 502 may be obtained from one or more publically-accessible databases (e.g., the Human Connectome Project) and/or data associated with one or more publications. The MR volume 502 may include brain MR images. Additionally or alternatively, the MR volume 502 may include MR images of other body parts. The MR volume 502 may be represented mathematically $$x_0 \in \mathbb{R}^{N_{x_0} \times N_{y_0} \times N_{z_0}},$$

where $N_{x_0} \times N_{y_0} \times N_{z_0}$ are the dimensions of the volume (e.g., in pixels).

Next, at 504, desired field of field view FOV(FOV$_x$, FOV$_y$, FOV$_z$) and image resolution (N$_x$,N$_y$,N$_z$) may be specified, and at 506 the MR volume 502 may be cropped and/or resampled to obtain an updated MR volume x' having the desired field of view and image resolution, such that x'∈ $\mathbb{R}^{N_x \times N_y \times N_z}$.

Next, in some embodiments, the updated MR volume x' may be further modified, at 512, by the application of one or more transformations T(x) (generated at 508) and/or application of a histogram augmentation function I(x) (generated at 510) to obtain the updated MR volume x"(r)=I(x' (T(r))). Such modifications permit generating multiple different training examples from a single underlying MR volume (i.e., MR volume 502), which is a type of training data augmentation, as described above.

In some embodiments, the transformation(s) T(x) (generated at 508) may include one or more 2D or 3D rigid transformations, one or more 2D or 3D affine transformations (e.g., one or more translations, one or more rotations, one or more scalings) and/or one or more 2D or 3D non-rigid transformations (e.g., one or more deformations). In some embodiments, each such transformation may be implemented by using a data augmentation matrix (e.g., a 3×3 matrix for a rigid transformation, a 4×4 matrix for an affine transformation, and a dense deformation grid (e.g., of the same dimensionality as the MR volume) for a non-rigid transformation).

In some embodiments, an affine transformation T(x) may be generated at random at 508 to simulate a realistic variation of how different positions and orientations of a patient's anatomy may be positioned within the MRI system. For example, if the field of view of the image is 22 cm, transformations sampled at 508 may translate the MR volume by a distance of up to 5 cm and/or rotate the MR volume by up to 30 degrees along the axial angle. A non-rigid transformation T(x) may be generated at random at 508 to simulate the effect of inhomogeneity of the B$_0$ field, eddy currents and/or encoding error of the MRI system.

In some embodiments, the histogram augmentation function I(r) generated at 510 may be used to change the intensity variations in regions of the image to simulate various effects, including, but not limited to the effect of RF coil correlation and/or to provide different contrasts that may occur in multi-echo pulse sequences.

Next, at acts 514, 516, and 518, synthetic phase is generated from a linear combination of spherical harmonic basis functions to generate the target complex-valued volume x 520. In some embodiments, coefficients $\alpha_i$ of N spherical harmonic basis functions $Y_i$ are sampled, at 514, at random to generate a phase image, at 516, according to: $\theta = \sum_{i=1}^{N} \alpha_i Y_i$. In turn, the complex-valued target vole 520 may be given by: x=x"(r)e$^{i\theta}$. In some embodiments, the number of spherical harmonics is selected by the user—the greater the number, the more complex the resulting phase. In some embodiments, the range of values for each spherical harmonic coefficient $\alpha_i$ may be set by user, for example, empirically.

Next, after the target image 520 is generated, act 525 (which includes acts 522-544 is repeated) multiple times (N$_{avg}$ times in this example) to generate multiple sets of spatial frequency data, each set including spatial frequency data for N$_{coil}$ RF coils (8 in this example). Within act 525, first sequence specific augmentation is performed at acts 522 and 524.

In some embodiments, one or more transformations may be generated, at 522, at random, to apply to target MR volume 520, and subsequently be applied to the target MR volume at 524. Generating the transformations, at 522, may include: (1) generating, at 522a, RF artefacts (e.g., internal RF interference, noise) to simulate the types of RF artefacts that may be expected to be observed during a particular pulse sequence; and (2) generating, at 522b, one or more affine or non-rigid transformations to simulate the effect of patient motion during a particular pulse sequence (inter-volume motion).

Next, at acts 526 and 528, an RF coil sensitivity profile is generated for each of the N$_{coil}$ RF coils to obtain multiple RF coil sensitivity profiles S$_i$, i=1 ... N$_{coil}$. Each generated RF coil sensitivity profile S$_i$ is complex-valued, with the magnitudes generated at act 526 using one or more RF coil models and with the phases generated (e.g., randomly) at 528. The resulting RF sensitivity profiles are applied to the MR volume (e.g., to the result of performing, at 524, pulse sequence specific augmentation on target MR volume 520) to obtain multiple MR volumes, each of the multiple MR volumes obtained by applying a respective RF coil sensitivity profile to the MR volume resulting at the output of 524.

The RF coil model used at 524 may be of any suitable type. For example, in some embodiments, the RF coil model used at 526 may be a physics-based RF coil model, which may be configured to calculate the sensitivity of a particular RF coil given its geometry. The physics-based model may be performed for multiple coils simultaneously to determine any RF coil coupling and/or inductance effects (e.g., the results of that calculation may be used at 532, as discussed below). In other embodiments, the RF coil model may be a statistical model having a Gaussian profile for the amplitude and smooth complex phase. In yet other embodiments, a non-uniform map having the same dimension as each volume slice may be employed, where each pixel is weighted by a smooth amplitude reduction map and noise is added to determine an overall reduction in SNR that is to be applied.

Next at 532, a coil correlation matrix L' may be determined. This matrix may model the effect of RF coil coupling and/or inductance. The coil correlation matrix L' may be determined based on a model of RF coil inductance (e.g., a physics-based model as described above). Next, at 534, the coil correlation matrix may be perturbed (e.g., randomly) to obtain a coil correlation matrix L. At 536, the coil correlation matrix L is applied to the pixel data.

Next, at 538 and 540, correlated Gaussian noise is generated and added, at 542, to the multiple MR volumes produced at 536. In some embodiments, the Gaussian noise may be generated by: (1) determining, at 538, a noise level $\sigma_i$ for each of the coils; and (2) generating, at 540, Gaussian noise having the covariance of $LDL^T$, where D is a diagonal matrix with $D_{ii}=\sigma_i$, and L is the coil correlation matrix determined at 534.

Next, at 544, a k-space sampling trajectory is selected. The sampling trajectory may be of any suitable type. It may be Cartesian or non-Cartesian (e.g., radial, spiral, rosette, variable density, Lissajou, etc.). Next, at 546, noise $\delta k(t)$ is added to sampling trajectory $k(t)$. The noise may be added to simulate for various MRI system imperfections and/or any other reason. Next, at 548, a non-uniform Fourier transform is applied to the noise-corrupted coil-weighted MR volumes produced at 542.

As a last step, at 545, k-space augmentation may be performed to perform further sequence-specific augmentation. For example, this may be done to model them impact of the basebanging artefact in bSSFP (balanced stead state free precession) sequences or warping artefacts in DWI (diffusion weighted imaging).

The resulting spatial frequency data are then output, at 550. These data may be used for training any of the neural network models described herein.

It should be appreciated that the process 500 is illustrative and that there are variations thereof. For example, one or more of the acts of process 500 may be omitted, in some embodiments. For example, when generating data for training a neural network to operate on data collected by an MRI system having a single RF coil, acts 532-542 may be omitted, in some embodiments. As another example, one or more of the augmentation acts (e.g., k-space augmentation at 545) may be omitted, in some embodiments.

Unsupervised Learning with Low-Field Data

As described herein, including above with reference to FIG. 5, in some embodiments, neural network models developed by the inventors and described herein may be trained using training data generated from existing high-field image data. Indeed, a training dataset of (sensor input data, image) pairs may be generated by, for each pair, starting with a high-field source image $x_h$ and using a model of the "forward process" (e.g., the forward process described with reference to FIG. 5) to generate input sensor data $y_h$, thereby forming the pair $(y_h, x_h)$. However, the inventors have recognized that generating training data from high-field data, training neural network models on such training data, and then applying the trained neural network models to process low-field data (e.g., data collected using an MRI system having a $B_0$ field strength between 0.02 T and 0.2 T) results in worse performance as compared to when the trained neural network models are applied to the type of high-field data that their training dataset was generated from. This problem is often referred to as "domain shift."

One way of mitigating domain shift is to a train neural network from low-field data when the trained neural network is to be applied to low-field data and to train neural networks from high-field data when the trained neural network is to be applied to high-field data. However, there is simply insufficient low-field MR data from which to train and the existing data is noisy, making it very difficult to generate low-field (k-space data, image) pairs. As a result, training a neural network from purely low-field data is not always possible.

The inventors have recognized that this problem may be addressed by training the neural network with data pairs derived from high-field data (as above), but also augmenting the loss function with losses computed with respect to available low-field images. The key insight is that, even if a neural network were trained using high-field data, the resulting network should reconstruct the same image from both: (1) a first set of low-field k-space data; and (2) a second set of low-field data obtained by applying a geometric transformation to the first set of low-field k-space data, where the image reconstruction should be invariant under the transformation.

For example, rotating the input sensor domain data along by a particular rotation angle, should simply cause the reconstructed image to be rotated by the same angle. Other non-limiting examples of geometric transformations with respect to which the image reconstruction should be invariant include linear shift, phase shift, conjugation, and flipping.

Accordingly, in some embodiments, the loss function for training a neural network model for performing image reconstruction (e.g., neural network model 212), may incorporate a loss applied on low-field data. Formally, let $x \in \mathbb{C}^N$ denote a complex-valued MR image to be reconstructed, represented as a vector with $N=N_x N_y$, where $N_x$ and $N_y$ are width and height of the image. Let $y \in \mathbb{C}^M$ ($M<<N$) represent the under-sampled k-space measurements. Denote the image reconstruction by a trained neural network f that generates x from y. Then, in some embodiments, the neural network may be trained using the following loss function:

$$\mathcal{L}_{self} = E_{y \sim p(y_h)}[\mathcal{L}_1] + E_{y \sim p(y)}[\mathcal{L}_2 + \mathcal{L}_3],$$

where the constituent loss functions are given by:

$$\mathcal{L}_1 = \|f(y_h) - x_h\|, \mathcal{L}_2 = \|f(y) - T^{-1}(f(T(y)))\|, \mathcal{L}_3 = \mathcal{R}(f(y)).$$

Here, the loss function $\mathcal{L}_1$ penalizes errors in reconstruction of high-field images; it is based on the available data pairs generated from high-field images. The loss function $\mathcal{L}_2$ penalizes errors between image reconstructions of a data set and a geometric transformation thereof, where the reconstruction should be invariant to action by the geometric transformation. The loss function $\mathcal{L}_3$ implements a regularization term, such as total variation norm, which is typically applied in compressed sensing type reconstructions. In some embodiments, the loss function $\mathcal{L}_{self}$ may be a weighted combination of the individual loss functions $\mathcal{L}_1$, $\mathcal{L}_2$ and $\mathcal{L}_3$.

Additionally or alternatively, another way to generate a training dataset is to use source images of higher quality $x_o$, such as those obtained from low-field scanners, but using more data samples. The sensor data can be obtained directly by collecting the scanner measurements $y_o$. The higher quality data $x_o$ and input data x are related by a mask in the sensor domain, i.e. $y=M \cdot y_o$. The training loss can then be written as:

$$\mathcal{L}_4 = \|f(y) - x_o\|$$

Motion Correction and Alignment

As described herein, multiple MR images of a single slice of a patient's anatomy may be acquired in order to enhance MR image quality by averaging the multiple MR images to increase the resulting SNR. Multiple sets of images covering a same volume of the patient's anatomy (e.g., a volume containing multiple slices of the patient's anatomy) may be acquired and averaged for the same reason. However, performing multiple acquisitions (e.g. of the same slice and/or of the same volume) increases the overall total acquisition time, which in turn increases the likelihood that the patient moves during imaging. On the other hand, patient motion causes misalignment between the multiple acquisitions. Averaging such misaligned acquisitions would not improve SNR as is desirable and, instead, may degrade the images, for example, through blurring.

As described herein, the inventors have developed deep learning techniques for aligning sets of images obtained by multiple acquisitions of the same slice and/or volume. In some embodiments, the deep learning techniques involve using a cascade of two or more neural networks configured to estimate a transformation (e.g., a non-rigid, an affine, a rigid transformation) between two sets of MR images (each set having one or multiple MR images), and aligning the two sets of images using the estimated transformation. In turn, the two sets of images may be averaged to obtain a combined set of images having a higher SNR than the sets of images themselves.

In some embodiments, the estimated transformation may indicate one or more rotations and/or translations to align the two sets of images. In some embodiments, the deep learning techniques described herein may be used as part of neural network 234 part of post-reconstruction neural network 214, as described herein including in connection with FIG. 2C.

Accordingly, some embodiments provide for a system and/or a method for generating MR images of a subject from MR data obtained by an MRI system. In some embodiments, the method includes: (1) obtaining first input MR data obtained by imaging the subject using the MRI system; (2) obtaining second input MR data obtained by imaging the subject using the MRI system; (3) generating a first set of one or more MR images from the first input MR data (e.g., by reconstructing the first set of MR images from the first input MR data); (4) generating a second set of one or more MR images from the second input MR data (e.g., by reconstructing the second set of MR images from the second input MR data); (5) aligning the first set of MR images and the second set of MR images using a neural network model to obtain aligned first and second sets of MR images, the neural network model comprising a first neural network and a second neural network; (6) combining the aligned first and second sets of MR images to obtain a combined set of one or more MR images; and (7) outputting the combined set of one or more MR images.

In some embodiments, the aligning may include: (a) estimating, using the first neural network, a first transformation (e.g., a first rigid transformation expressed as a combination of one or more translations and/or one or more rotations) between the first set of MR images and the second set of MR images; (b) generating a first updated set of MR images from the second set of MR images using the first transformation; (c) estimating, using the second neural network, a second transformation (e.g., a second rigid transformation expressed as a combination of one or more translations and/or one or more rotations) between the first set of MR images and the first updated set of MR images; and (d) aligning the first set of MR images and the second set of MR images at least in part by using the first transformation and the second transformation (e.g., by using a composition of the estimated two transformations. In some embodiments, a software program may perform the above-described acts. Alternately, one or more of these acts may be implemented using hardware. Accordingly, the MR image generation techniques described herein may be implemented using hardware, software, or any suitable combination of hardware and software.

In some embodiments, obtaining the second input MR data may be performed after obtaining the first input MR data. For example, the first input MR data may contain MR data for each of multiple slices of a volume, the second input MR data may contain MR data for the same slices of the same volume, and all of the second input MR data may be acquired after the first input MR data. In other embodiments, the acquisition of the first and second input MR data may be interlaced: MR data for a first slice is obtained twice (the first instance will be part of the first set of input MR data and the second instance will be part of the second set of input MR data), then MR data for a second slice is obtained twice (the first instance will be part of the first set of input MR data and the second instance will be part of the second set of input MR data), then MR data for a third slice is obtained twice (the first instance will be part of the first set of input MR data and the second instance will be part of the second set of input MR data), and so on.

In some embodiments, generating the first updated set of MR images from the second set of MR images, comprises applying the first transformation to the second set of MR images. The first transformation may, for example, be a rigid transformation. In some embodiments, the first transformation may include one or more translations and/or one or more rotations determined by the first neural network. The translations may describe one or more translations along the x-, y-, and/or z-directions. The rotations may describe one or more rotations about the x, y, and/or z axes. In some embodiments, the rotations may be described by rotation angles (e.g., Euler rotation angles). In some embodiments, estimating the first transformation may be performed at least in part by using the aligning is performed by at least one graphics processing unit (GPU) part of the MRI system.

In some embodiments, generating the first updated set of MR images additionally comprises interpolating results of applying the first transformation to the second set of MR images. For example, a pixel value of an image of the second set of MR images may be, after a transformation is applied, located "between" pixels of the pixel array of the transformed MR image. Pixel values of the transformed MR image may be interpolated based on, for example, an average of signal values within a vicinity of each pixel or in any other suitable way, as aspects of the technology described herein are not limited in this respect.

In some embodiments, aligning the first set of MR images and the second set of MR images may comprise calculating a composed transformation by composing the first and second transformations. For example, in some embodiments, the composed transformation may be obtained by composing the rotation and translation parameters of the first and second transformations. The composed transformation may be applied to the second set of MR images to obtain a set of MR images aligned to the first set of MR images.

Alternatively, in some embodiments, aligning the first set of MR images and the second set of MR images may comprise obtaining a set of MR images aligned to the first set of MR images from the first set of updated MR images. In some embodiments, the aligning may be performed by at least one processor part of the MRI system.

In some embodiments, the neural network model additionally includes a third neural network. In such embodiments, the aligning of the first set of MR images and the second set of MR images further comprises: (e) generating a second updated set of MR images from the first updated set of MR images using the second transformation; (f) estimating, using the third neural network, a third transformation between the first updated set of MR images and the second updated set of MR images; and (g) aligning the first set of MR images and the second set of MR images at least in part by using the first transformation, the second transformation, and the third transformation (e.g., by composition of at least the first, second, and third transformations).

In some embodiments, the first neural network comprises one or more two-dimensional (2D) convolutional layers. In some embodiments, the first neural network comprises one or more three-dimensional (3D) convolutional layers configured to simultaneously process data in multiple images of the first set of MR images (e.g., to process volumetric data).

In some embodiments, the first set of MR images may consist of one image and the second set of MR images may consist of one MR image. In such embodiments, the first set of MR images and the second set of MR images may describe a single slice of the imaging volume. Alternately, the alignment of first and second sets of MR images may be performed by the neural network an image-at-a-time (e.g., by comparing single MR images rather than comparing multiple MR images that describe the entire imaging volume).

In some embodiments, combining the aligned first and second sets of MR images comprises averaging images of the aligned first and second sets of MR images. For example, images of the aligned first and second sets of MR images corresponding to a same slice of the imaging volume may be averaged to increase SNR in the resulting combined image.

Figure 6:
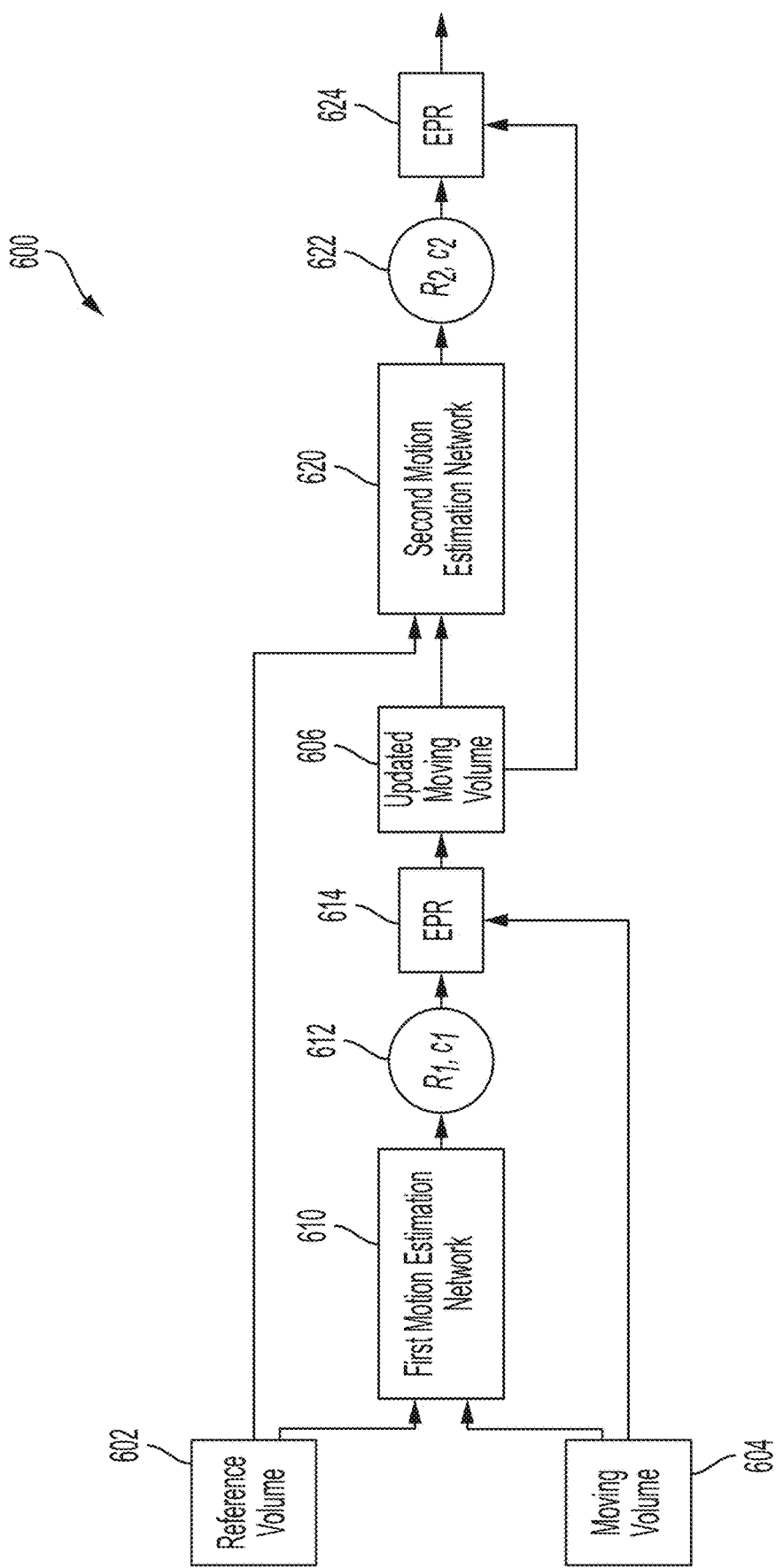
FIG. 6 is a diagram of an example neural-network based architecture for aligning one or more MR images, in accordance with some embodiments of the technology described herein.

FIG. 6 is a diagram of an example neural-network based architecture 600 for aligning one or more MR images, in accordance with some embodiments of the technology described herein. As can be appreciated from FIG. 6, the architecture 600 is cascaded because it comprises a cascade of neural networks, each configured to estimate a respective transformation between two sets of MR images. Since the transformation may account for patient motion during collection of the two sets of MR images, these neural networks are termed motion estimation networks.

In the embodiment of FIG. 6, the cascaded architecture 600 includes two motion estimation networks: first motion estimation network 610 and second motion estimation network 620 configured to determine motion transformation parameters (e.g., rotation and/or translation parameters) between reference volume 602 and moving volume 604. Though it should be appreciated that, in other embodiments, the cascaded architecture may include more than two motion estimation neural networks (e.g., three, four, five, six, seven, eight nine, ten, etc.), as aspects of the technology described herein are not limited to using exactly two motion estimation networks.

The inventors have appreciated that using a cascade of multiple neural networks to estimate a series of transformations to align the sets of images may lead to improved performance relative to the implementation where only one motion estimation neural net is used because a single transformation may not achieve a perfect alignment, but a series of transformations, each aligning a moving volume successively closer to the reference volume, may achieve a much higher degree of alignment. Though it should be appreciated that, in some embodiments, a single motion estimation neural network may be used.

In some embodiments, the reference volume 602 may include a set of one or more MR images generated based on a first set of MR data obtained by imaging a patient using the MRI system. In some embodiments, the set of MR images may be real-valued images (phase information may be discarded). For example, the reference volume 602 may include multiple MR images, each of which corresponds to a different volumetric slice of the imaged patient (e.g., the multiple MR images may include multiple sagittal slices, multiple axial slices, or multiple coronal slices) obtained from a first instance of an MR imaging protocol (e.g., a series of one or more pulse sequences for imaging the patient). In some embodiments, the reference volume 602 may be provided as an input to each of the motion estimation networks 610 and 620 of the cascaded architecture 600.

In some embodiments, the moving volume 604 may include a set of one or more MR images generated based on a second set of MR data obtained by imaging a patient using the MRI system. For example, the moving volume 604 may include MR images each of which corresponds to a different volumetric slice of the patient (e.g., the MR images may include multiple sagittal slices, multiple axial slices, or multiple coronal slices), and each of the images in the moving volume 604 may have a corresponding image included in reference volume 602. In some embodiments, the moving volume 604 may be used as an input of the first motion estimation network 610 and the first estimated parameter resampler (EPR) 614, as described below.

In some embodiments, first motion estimation network 610 may be a neural network configured to take two sets of MR images (e.g., reference volume 602 and moving volume 604) as input and output estimated transformation parameters (e.g., first transformation parameters 612), which describe a transformation for aligning the moving volume 604 to the reference volume 602 (the misalignment being caused, for example, by patient movement during imaging).

In some embodiments, the first motion estimation network 610 may be a convolutional neural network having one or more convolutional layers, one or more transpose convolutional layers, one or more non-linearity layers, and/or one or more fully connected layers. In some embodiments, the network 610 may be a 2D convolutional neural network or a 3D convolutional neural network. An example architecture of network 610 is described herein including with reference to FIG. 7.

In some embodiments, the first transformation parameters 612 output by first motion estimation network 610 may include parameters of a rigid transformation for aligning the reference volume 602 and the moving volume 604 to one another. For example, the first transformation parameters 612 may include one or more translation parameters to describe translation along x-, y-, and/or z-directions. Alternatively or additionally, the first transformation parameters 612 may include rotation angles (e.g., Euler rotation angles) describing rotation about the x, y, and/or z axes.

Next, as shown in FIG. 6, the first transformation parameters 612 are used to transform the moving volume 604 to obtain an updated moving volume 606. This transformation may be performed by Estimated Parameter Resampler 614. For example, the first transformation parameters 612 may include one or more rotation and/or translation parameters, and the EPR 614 may transform the moving volume 604 by applying one or more rotations and/or translations defined by the parameters 612 to the moving volume 604.

In some embodiments, generating the updated moving volume 606 may also include interpolating one or more points within the first updated set of MR images of the updated moving volume 606. As an example, each MR image of the moving volume 604 is formed from an array of magnitude values, each magnitude value being associated with a pixel of the MR image. When a rotation translation is applied to an MR image, the magnitude values may no longer cleanly align with the pixel array of the updated MR image (e.g., the magnitude may correspond to a location "between" array locations, pixels at the edge of the image may be cut off or missing). Interpolation may therefore be used to assign magnitude values to each pixel of the array forming the updated MR image. Any suitable type of interpolation technique may be used, as aspects of the technology described herein are not limited in this respect.

Next, the reference volume 602 and the updated moving volume 606 are provided as input to the second motion estimation network 620. Second motion estimation network 620 may be configured to take in two sets of MR images (e.g., reference volume 602 and updated moving volume 606) and output estimated transformation parameters (e.g., transformation parameters 622) which describe an estimated magnitude and type of "motion" represented by the differences between reference volume 602 and updated moving volume 606.

In some embodiments, the network 620 may be a convolutional neural network having one or more convolutional layers, one or more transpose convolutional layers, one or more non-linearity layers, and/or one or more fully connected layers. In some embodiments, the network 610 may be a 2D convolutional neural network or a 3D convolutional neural network. In some embodiments, the second motion estimation network 620 may have the same architecture as the first motion estimation network 610, but with different parameter values since it is trained to perform a different task (correcting a much smaller misalignment than the first motion estimation network). In other embodiments, the second motion estimation network 620 may have a different architecture (e.g., different number of convolutional layers, different convolutional kernel size, different number of features, different non-linearity, and/or any other suitable difference).

As shown in FIG. 6, the second motion estimation network 620 outputs second transformation parameters 622. In some embodiments, the parameters 622 include parameters of a rigid transformation between reference volume 602 and updated moving volume 606. For example, the parameters 622 may include one or more translation parameters to describe translation along x-, y-, and/or z-directions. Alternatively or additionally, the first transformation parameters 612 may include rotation angles (e.g., Euler rotation angles) describing rotation about the x, y, and/or z axes.

In some embodiments, an output of the cascaded architecture 600 may include a final transformed volume (not pictured). In the example of cascaded architecture 600, as depicted in FIG. 6, the final transformed volume is generated after second EPR 624 resamples updated moving volume 606. The final transformed volume may include the cumulative transformations and interpolations as applied by the one or more motion estimation networks as the moving volume has been updated through cascaded architecture 600.

In some embodiments, the cascaded architecture 600 may alternatively or additionally output the transformation parameters (e.g., transformation parameters 614 and 622) determined by its constituent motion estimation networks. The transformations defined by these parameters may be composed, and the composed transformation may be applied to the moving volume 604, with an interpolation step optionally following, to obtain a volume that is aligned with reference volume 602.

As one non-limiting example, the transformation parameters $\{R_1, \ldots, R_n, c_1, \ldots, c_n\}$ may be used to generate a composed transformation according to $$T_{final} = T_n * T_{n-1} * \ldots * T_1$$

where $T_i = [R_i | c_i; 011]$ is a 4×4 transformation matrix and "*" is a matrix multiplication. The composed transformation, $T_{final}$, may then be applied to moving volume 604, with an interpolation step optionally following, to obtained a volume that is aligned with reference volume 602.

In some embodiments, the first motion estimation network 610 may be trained using a loss function based on error in the first transformation parameters 612. However, this approach suffers from multiple drawbacks (e.g., there are multiple transformation parameters that may achieve the same result and computing the error on a small number of parameters, for example 6, may not be sufficiently informative for training purposes). Instead, the inventors have recognized that the estimated transformation 612 may be used to resample the moving volume 604 and to compute the loss function for training the network 610 based on the image-domain error between the reference volume 602 and the resampled moving volume 604.

For example, in embodiments where the architecture 600 includes only the network 610, the loss function may be computed by resampling MR images of moving volume 604 based on the first transformation parameters 612. The resampling may be performed by first EPR 614. The loss function would then be given by:

$$L(\theta) = \|V_{ref} - EPR(NN(V_{mov}|\theta))\|_2$$

where $\theta$ is the network parameter to be optimized during training, $V_{ref}$ is the reference volume (e.g., reference volume 602), $V_{mov}$ is the moving volume (e.g., moving volume 604), and $NN(V_{mov}|\theta)$ is the output of the neural network (e.g., the output of first motion estimation network 610) for a specified $V_{mov}$ and $\theta$.

When the architecture 600 includes multiple (say n) motion estimation networks (as is the case for FIG. 6), a different loss function may be used as described below, the loss function, $L_n(\theta)$ may be used, which is calculated based on the resampling performed by the EPRs (e.g., first EPR 614 and EPR 624) according to:

$$L_n(\theta) = \|V_{ref} - EPR(NN_n(\ldots(EPR(NN_2(EPR(NN_1(V_{mov}|\theta)))) \ldots ))\|_2$$

where $\theta$ is the network parameter to be optimized during training, $V_{ref}$ is the reference volume (e.g., reference volume 602), $V_{mov}$ is the moving volume (e.g., moving volume 604), and $NN_n(V_{mov}|\theta)$ is the output of the $n^{th}$ motion estimation network.

Figure 7:
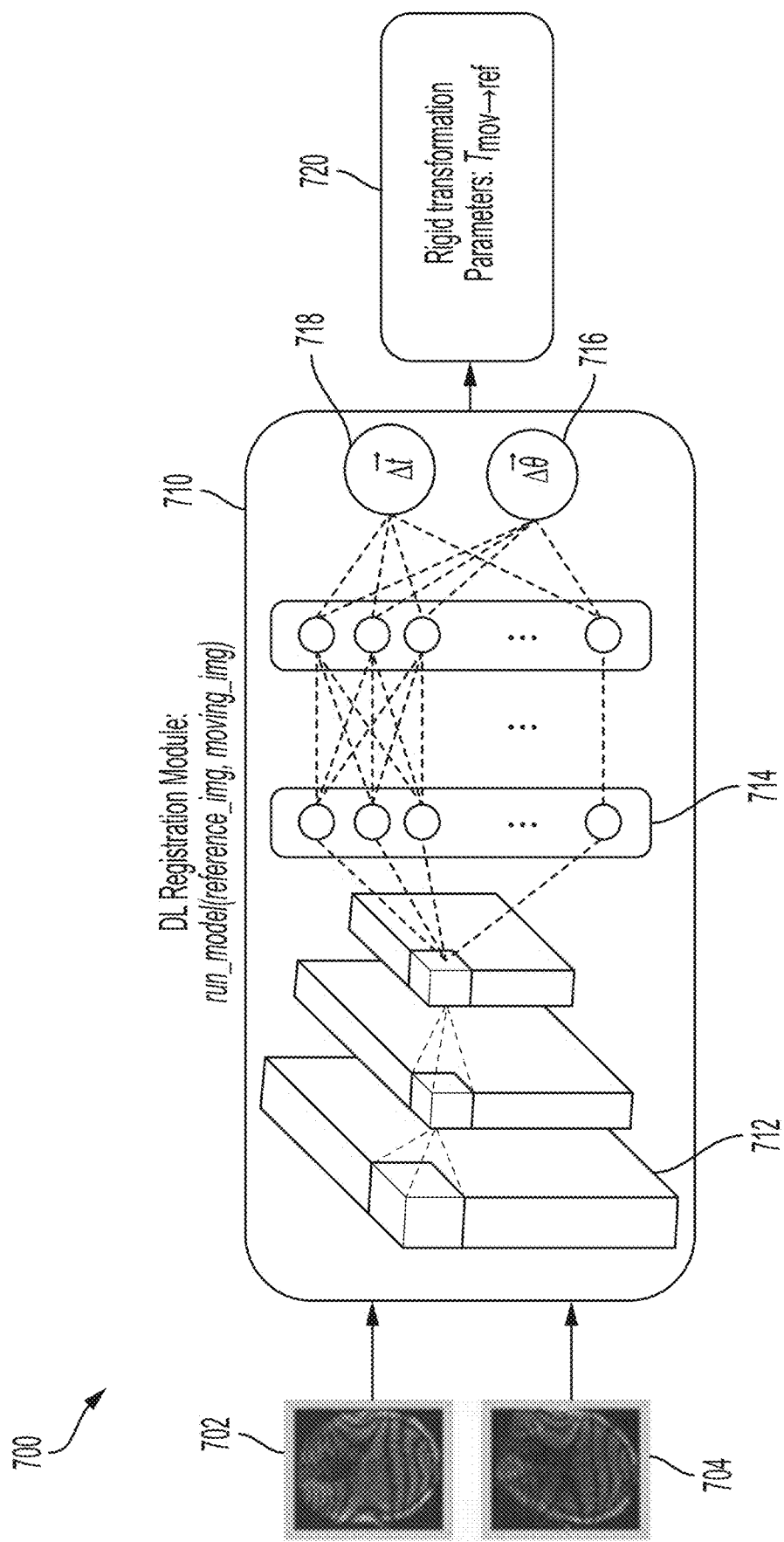
FIG. 7 is a diagram of the architecture of an illustrative neural network for aligning one or more MR images, in accordance with some embodiments of the technology described herein.

FIG. 7 is a diagram 700 of the architecture of an illustrative neural network 710 for aligning one or more MR images, in accordance with some embodiments of the technology described herein. Neural network 710 may be used as one or more of the motion estimation networks of cascaded architecture 600, as described in connection with FIG. 6.

In some embodiments, neural network 710 may be configured a first set of MR images 702 and a second set of MR images 704. For example, in embodiments where motion estimation network 710 is used as first motion estimation network 610 of cascaded architecture 600, the first set of MR images 702 may be reference volume 602 and the second set of MR images 704 may be moving volume 604. As another example, in embodiments where neural network 710 is used as a subsequent motion estimation network (e.g., second motion estimation network 620), the first set of MR images 702 may be reference volume 602 and the second set of MR images 704 may be an updated moving volume (e.g., updated moving volume 606) generated by an EPR (e.g., EPR 615).

In some embodiments, neural network 710 may be a convolutional neural network comprising one or more convolutional layers 712. For example, convolutional layers 712 may be two-dimensional (2D) convolutional layers. In such embodiments, neural network 710 may be configured to process individual, 2D MR images (e.g., representing a single volumetric slice). The processing of an entire imaging volume may be performed a slice at a time. Alternately, in some embodiments, convolutional layers 712 may comprise three-dimensional (3D) convolutional layers. In such embodiments, neural network 710 may be configured to simultaneously process multiple MR images representing an entire imaging volume.

In some embodiments, one or more fully connected layers 714 may be applied to the output of convolutional layers 712. In some embodiments, the output of convolutional layers 712 may be reshaped into a one-dimensional (1D) vector before the application of the one or more fully connected layers 714. Additionally, in some embodiments, a dropout layer (not shown) may be included after one or more (or each) of the fully connected layers 714.

Although not expressly shown in FIG. 7, a non-linearity layer (e.g., a rectified linear unit or ReLU, sigmoid, etc.) may be applied after any of the one or more layers shown in the neural network 710. For example, a non-linearity layer may be applied after one or more (or each) of the convolutional layers 712. Additionally or alternately, a non-linearity layer may be applied after one or more (or each) of the fully connected layers 714.

In some embodiments, neural network 710 may be implemented as a 3D convolutional network having the following architecture:

1. 3D Convolution, kernel size=3×3, stride=1, 8 features, ReLU
2. 3D Convolution, kernel size=3×3, stride=1, 8 features, ReLU
3. 3D Convolution, kernel size=3×3, stride=1, 8 features, ReLU
4. 3D Convolution, kernel size=3×3, stride=2, 8 features, ReLU
5. 3D Convolution, kernel size=3×3, stride=1, 16 features, ReLU
6. 3D Convolution, kernel size=3×3, stride=1, 16 features, ReLU
7. 3D Convolution, kernel size=3×3, stride=1, 16 features, ReLU
8. 3D Convolution, kernel size=3×3, stride=2, 16 features, ReLU
9. 3D Convolution, kernel size=3×3, stride=1, 32 features, ReLU
10. 3D Convolution, kernel size=3×3, stride=1, 32 features, ReLU
11. 3D Convolution, kernel size=3×3, stride=1, 32 features, ReLU
12. 3D Convolution, kernel size=3×3, stride=2, 32 features, ReLU
13. 3D Convolution, kernel size=3×3, stride=1, 64 features, ReLU
14. 3D Convolution, kernel size=3×3, stride=1, 64 features, ReLU
15. 3D Convolution, kernel size=3×3, stride=1, 64 features, ReLU
16. Reshape the volume to a 1D vector
17. Fully Connected Layer to 256 features, RELU
18. Dropout Layer
19. Fully Connected Layer to 256 features, RELU
20. Dropout Layer
21. Fully Connected Layer to 256 features It may be appreciated that the above neural network architecture is by way of example only, and that neural network 710 may have any other suitable architecture, as aspects of the technology described herein are not limited in this respect.

In some embodiments, the fully connected layers may determine relative values of rotation, $\Delta \vec{\theta}$, and relative values of translation, $\Delta \vec{t}$, between the first set of MR images 702 and the second set of MR images 704. The relative values of rotation, $\Delta \vec{t}$, may comprise estimated rotation angles (e.g., Euler angles) describing rotation of the motion-corrupted set of MR images 704 about the x, y, and/or z axes relative to the reference set of MR images 702. The relative values of translation, $\Delta \vec{t}$, may comprise estimated translation values (e.g., distances) of the second set of MR images 704 along x-, y-, and/or z-directions relative to the first set of MR images 702.

In some embodiments, motion estimation network 700 may use the determined relative values of rotation, $\Delta \vec{\theta}$, and the determined relative values of translation, $\Delta \vec{t}$, to estimate rigid transformation parameters 720. Rigid transformation parameters 720 may describe a rigid transformation that maps the second set of MR images 704 to the first set of MR images 702. The motion estimation network 700 may, in some embodiments, output rigid transformation parameters 720 as a set of transformation parameters (e.g., values of rotation angles, values of translations). In some embodiments, the motion estimation network 700 may output rigid transformation parameters 720 as a composed transformation function.

Figure 8A:
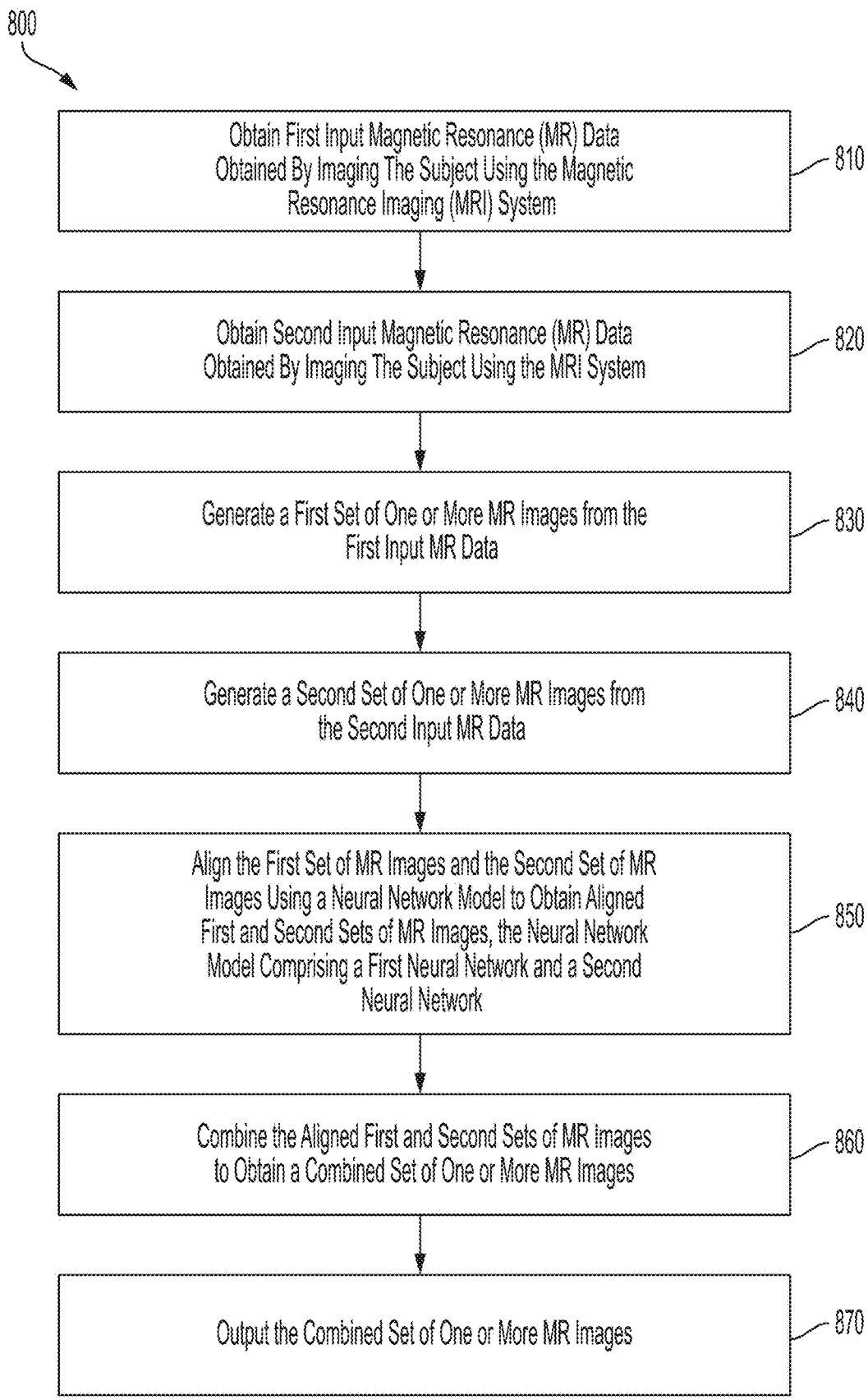
FIG. 8A is a flowchart of an illustrative process 800 for aligning one or more MR images, in accordance with some embodiments of the technology described herein.

FIG. 8A is a flowchart of an illustrative process 800 for aligning one or more MR images, in accordance with some embodiments of the technology described herein. Process 800 may be executed using any suitable computing device. For example, in some embodiments, the process 800 may be performed by a computing device co-located (e.g., in the same room) with an MRI system that obtained the MR data by imaging a subject (or object). As another example, in some embodiments, the process 800 may be performed by one or more processors (e.g., one or more GPUs) located on the MRI system that obtained the MR data. Alternately, in some embodiments, the process 800 may be performed by one or more processors located remotely from the MRI system (e.g., as part of a cloud computing environment) that obtained the input MR data.

Process 800 begins at act 810, where first input MR data is obtained. In some embodiments, the first input MR data had been previously obtained by an MRI system and stored for subsequent analysis, so that it is accessed at act 810. In other embodiments, the first input MR data may be obtained by an MRI system (including any of the MRI systems described herein) as part of process 800.

At act 820, second input MR data is obtained. In some embodiments, the second input MR data had been previously obtained by the MRI system and stored for subsequent analysis, so that it is accessed at act 820. In other embodiments, the second input MR data may be obtained by an MRI system (including any of the MRI systems described herein) as part of process 800.

In some embodiments, first input MR data and second input MR data may be obtained by the MRI system as repetitions of similar or same MR imaging protocols. For example, first input MR data and second input MR data may correspond, in some embodiments, to first and second MR imaging instances of the same imaging volume and/or slice. Patient motion may cause the contents of first and second input MR data to be misaligned in the image domain (e.g., post-reconstruction).

After obtaining the first and second input MR data, a first set of one or more MR images and a second set of one or more MR images may be generated from the first input MR data in act 830 and from the second input MR data in act 840, respectively, in accordance with some embodiments of the technology described herein. The first and second sets of MR images may be generated, for example, by reconstructing the first and second input MR data to transform the first and second input MR data from the spatial frequency domain to the image domain. The reconstruction may be performed in any suitable way, including linear and non-linear methods. For example, when the spatial frequency domain data is spaced on a Cartesian grid, the data may be transformed using an inverse 2D Fourier transformation (e.g., using the inverse 2D fast Fourier transform). As another example, when the spatial frequency domain data is under-sampled, the data may be transformed using an inverse non-uniform Fourier transformation, using a neural network model (e.g., reconstruction neural network 212), using compressed sensing and/or any other suitable methods, as aspects of the technology described herein are not limited in this respect.

Next, process 800 moves to act 850, in which the first set of MR images and the second set of MR images are aligned using a neural network model to obtain aligned first and second sets of MR images, in accordance with some embodiments of the technology described herein. The neural network model may be applied in the image domain and may have any suitable architecture, including any of the architectures described herein. In some embodiments, the processing at act 850 may be performed, as described herein including with reference to cascaded architecture 600 and/or neural network 710. In some embodiments, the neural network model may comprise multiple neural networks (e.g., as in first motion estimation network 610 and second motion estimation network 620 of cascaded architecture 600).

Figure 8B:
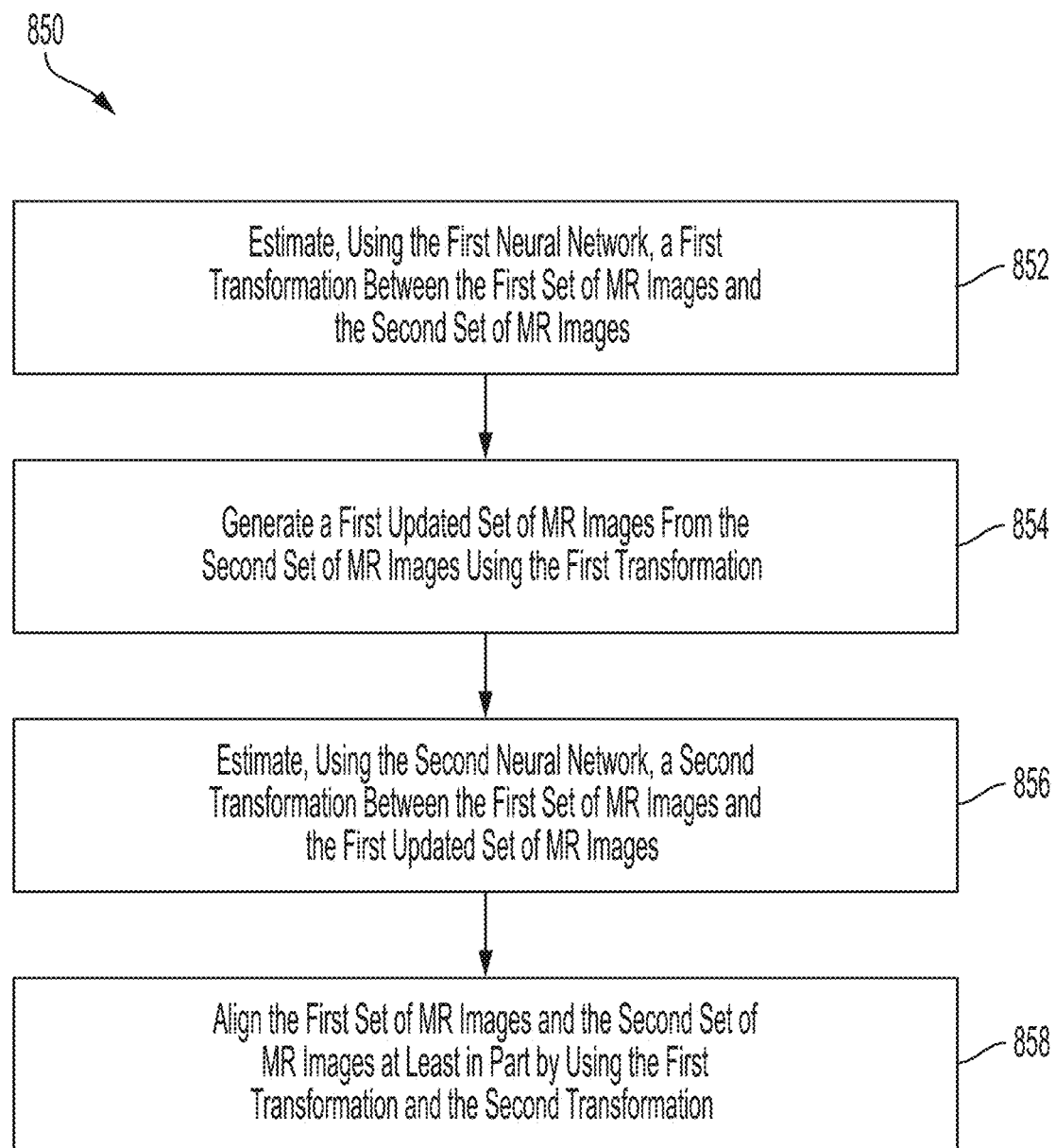
FIG. 8B is a flowchart of an illustrative implementation of act 850 of process 800 of FIG. 8B, in accordance with some embodiments of the technology described herein.

In some embodiments, act 850 of process 800 may include one or more additional acts to align the first set of MR images with the second set of MR images, as described by the flowchart of FIG. 8B. In some embodiments, a first transformation between the first set of MR images and the second set of MR images may be estimated using a first neural network in act 852. The processing at act 852 may be performed by a neural network having any suitable neural network architecture, including any of the architectures described herein. In some embodiments, the processing at act 852 may be performed as described herein, including with reference to neural network 710.

In some embodiments, the estimated first transformation may be any suitable transformation describing a transformation between the first and second sets of MR images, including any of the transformations described herein. For example, the first transformation may be a rigid transformation. In some embodiments, the first transformation may describe one or more translations (e.g., along any or each of the x-, y-, and/or z-directions) and/or may describe one or more rotations (e.g., about any or each of the x, y, and/or z axes). In other embodiments, the first transformation may be an affine or non-rigid transformation.

After completing act 852, process 800 moves to act 854, where a first updated set of MR images is generated from the second set of MR images using the first transformation. In some embodiments, the first updated set of MR images may be generated by applying the first transformation (e.g., any one of a number of translation and/or rotations) to the second set of MR images. In some embodiments, generating the first updated set of MR images may include interpolating one or more pixel values of the first updated set of MR images.

Next, process 800 moves to act 856, where a second transformation between the first set of MR images and the first updated set of MR images is estimated using the second neural network. The processing at act 856 may be performed by any suitable neural network architecture, including any of the architectures described herein. In some embodiments, the processing at act 856 may be performed in any way described herein, including with reference to neural network 710.

In some embodiments, the estimated second transformation may be any suitable transformation describing a transformation between the first set of MR images and the first updated set of MR images, including any of the transformations described herein. For example, the first transformation may be a rigid transformation. In some embodiments, the first transformation may describe one or more translations (e.g., along any or each of the x-, y-, and/or z-directions) and/or may describe one or more rotations (e.g., about any or each of the x, y, and/or z axes). In some embodiments, the second transformation may be configured to correct any misalignment remaining after the application of the first transformation to the second set of MR images.

Thereafter, process 800 moves to act 858, where the first set of MR images and the second set of MR images are aligned at least in part by using the first transformation and the second transformation. In some embodiments, the first set of MR images and the second set of MR images are aligned by generating a second set of updated MR images after estimating the second transformation. For example, the second transformation may be applied to the first updated set of MR images to generate a second set of updated MR images. In some embodiments, generating the second set of updated MR images may include interpolating one or more pixel values of the second set of updated MR images.

In some embodiments, the first set of MR images and the second set of MR images may be aligned by applying a composed transformation to the second set of MR images. For example, the neural network model may output one or more transformation parameters (e.g., of the first transformation, second transformation, and/or any other transformation) which may be used to generated a composed transformation, as described herein in connection with FIG. 6.

After acts 852-858 of act 850, process 800 moves to act 860, as shown in FIG. 8A, where the aligned first and second sets of MR images are combined to obtain a combined set of one or more MR images. In some embodiments, the aligned first and second sets of MR images may be combined by averaging images of the first and second sets of MR images. For example, images corresponding to a same slice of the imaging volume may be averaged to increase SNR in the resulting MR image. In some embodiments, the averaging may comprise a weighted average. After act 860 completes, process 800 moves to act 870 where the combined set of MR images is output (e.g., saved for subsequent access, transmitted to a recipient over a network, displayed to a user of the MRI system, etc.).

In some embodiments, the above-described networks and methods may be implemented as a part of a data processing pipeline, such as the example pipeline 900 of FIG. 9. In some embodiments, the pipeline 900 may receive a deep learning model 902 and MR images 904 as inputs. The deep learning model 902 may be any deep learning model configured to perform motion estimation and/or correction, as described herein. For example, the deep learning model may include any of the motion estimation networks described with reference to FIG. 6 or neural network 710. In some embodiments, the deep learning model 902 may be implemented in pipeline 900 as deep learning module 906.

In some embodiments, the input MR images 904 may be any related MR images (e.g., series of MR images representing the same imaging volume, series of MR images representing the same slice). In some embodiments, the input MR images 904 may have been previously obtained by an MRI system and stored for subsequent analysis, so that the input MR images 904 are accessed for input into pipeline 900. In other embodiments, the input MR images may be obtained by an MRI system (including any of the MRI systems described herein) including one or more processors to implement pipeline 900.

In some embodiments, pipeline 900 may select, using any suitable method, a first set of MR images from the input MR images 904 to be the set of reference MR images 908. The pipeline 900 may provide the set of reference MR images 908 and the remaining MR images of the input MR images 904 to the deep learning module 906 for processing.

In some embodiments, the deep learning module 906 may align the remaining MR images of the input MR images 904 to the reference MR images 908. The deep learning module 906 may implement any suitable alignment method to align the remaining MR images of the input MR images 904 with the reference MR images 908. For example, the deep learning module 906 may implement process 800 to align the images, as described in connection with FIGS. 8A and 8B.

The deep learning module may output one or more transformations 910 based on the reference MR images 908 and the remaining MR images of the input MR images 904, in some embodiments. The transformations 910 may be output as transformation parameters or as a composed transformation. In some embodiments, the transformations 910 may be any suitable transformation as described herein. For example, the transformations may be rigid transformations. In some embodiments, the transformation may describe one or more translations (e.g., along any or each of the x-, y-, and/or z-directions) and/or may describe one or more rotations (e.g., about any or each of the x, y, and/or z axes).

In some embodiments, the remaining MR images of the input MR images 904 may be resampled by estimated parameter resampler 912 based on transformations 910. Resampler 912 may use the transformations to transform the input MR images 902 (e.g., as described with reference to EPR 614).

In some embodiments, the pipeline 900 may evaluate at junction 914 whether the transformations 910 represent estimated motion that should be corrected. Some transformations 910 may not be a result of patient motion. For example, the partial volume effect, may result in small estimated transformations 910 that are not due to patient motion but are an artefact of the MR imaging process. In some embodiments, pipeline 900 may evaluate whether transformations 910 are above a certain threshold value. For example, pipeline 900 may evaluate whether a translation is above a translation threshold value (e.g., a translation of one pixel, a translation of two pixels, or any suitable threshold value) and/or whether a rotation is above a rotation threshold value (e.g., a rotation of one degree, a rotation of two degrees, or any suitable threshold value). If the transformations 910 are not greater than the threshold values, pipeline 900 may not correct the remaining MR images of the input MR images 904.

In some embodiments, pipeline 900 may output registered MR images 916. Registered MR images 916 may include reference MR image 908 and transformed remaining MR images of the input MR images 904. Transformed remaining MR images of the input MR images 904 may be transformed as a part of deep learning module 906, in some embodiments. Alternately, one or more transformations based on transformations 910 may be applied to remaining MR images of the input MR images 904 in order to obtain transformed remaining MR images of the input MR images 904.

Turning to FIG. 10, additional aspects of training neural networks configured to perform motion estimation and/or correction are described, in accordance with some embodiments of the technology described herein. It may, in some instances, be difficult to acquire large scale real motion-corrupted data for training of any of the neural network models described herein. Accordingly, in some embodiments, it may be desirable to generate synthetic training data including reference MR images and synthetic motion-corrupted MR images based on existing datasets 1002 of MR images. An illustrative process 1000 for generating such synthetic training dataset is described in connection with FIG. 10 herein.

Process 1000 may be executed using any suitable computing device. For example, in some embodiments, the process 1000 may be performed by a computing device co-located (e.g., in the same room) with an MRI system. As another example, in some embodiments, the process 1000 may be performed by one or more processors located remotely from the MRI system (e.g., as part of a cloud computing environment).

To generate such synthetic training datasets, a volume may be selected and loaded in act 1004 from dataset 1002. In some embodiments, only a magnitude portion of the volume may be loaded. After loading the selected volume in act 1004, a random affine transformation matrix T may be sampled in act 1006. In some embodiments, the random affine transformation matrix T may be sampled from a number of affine transformation matrices (e.g., stored in a database) or the random affine transformation matrix T may be randomly generated using any suitable random generation method.

In some embodiments, the sampled random affine transformation matrix T may then be applied to the loaded volume in act 1008. The transformed volume may be stored as a reference volume.

After generating the reference volume in act 1008, the process 1000 may proceed to acts 1010-1016 to generate the moving volume. In act 1010, a random rotation matrix R and a random translation vector c may be sampled. In some embodiments, the rotational matrix R and the random translation vector c may be sampled from a number of rotation matrices and translation vectors (e.g., stored in a database), or the random rotational matrix R and the random translation vector c may be randomly generated using any suitable random generation method. In act 1012, the sampled rotation matrix R and translation vector c may be applied to the reference volume to generate a moving volume.

To better train the neural network model, it may be desirable to include synthetic noise in the synthetic training data (e.g., to simulate non-ideal MR imaging conditions). In act 1014, Gaussian noise may be sampled in act 1014. The Gaussian noise may be selected to match the volume size of the loaded volume. Alternatively or additionally, in some embodiments, noise may be added to the reference volume and the moving volume by undersampling a percentage of the MR data in k-space. In act 1016, the Gaussian noise may be added to the reference volume and the moving volume to form the synthetic training data pair for use by the neural network model.

In some embodiments, additional non-rigid transformations (not pictured) may be applied to the moving volume to simulate pulse sequence-specific deformations that may be encountered by the neural network. Examples of such non-rigid transformations include dilation of the volume and/or shearing of the volume.

Figure 11A:
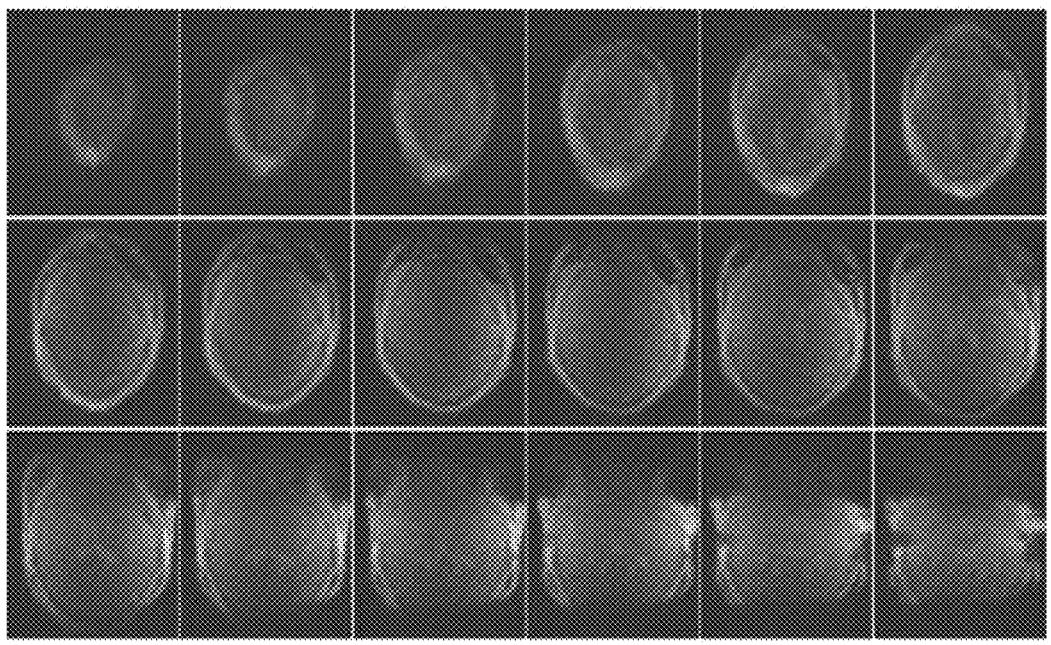
FIG. 11A illustrates example motion-corrupted MR images of a patient's brain.
Figure 11B:
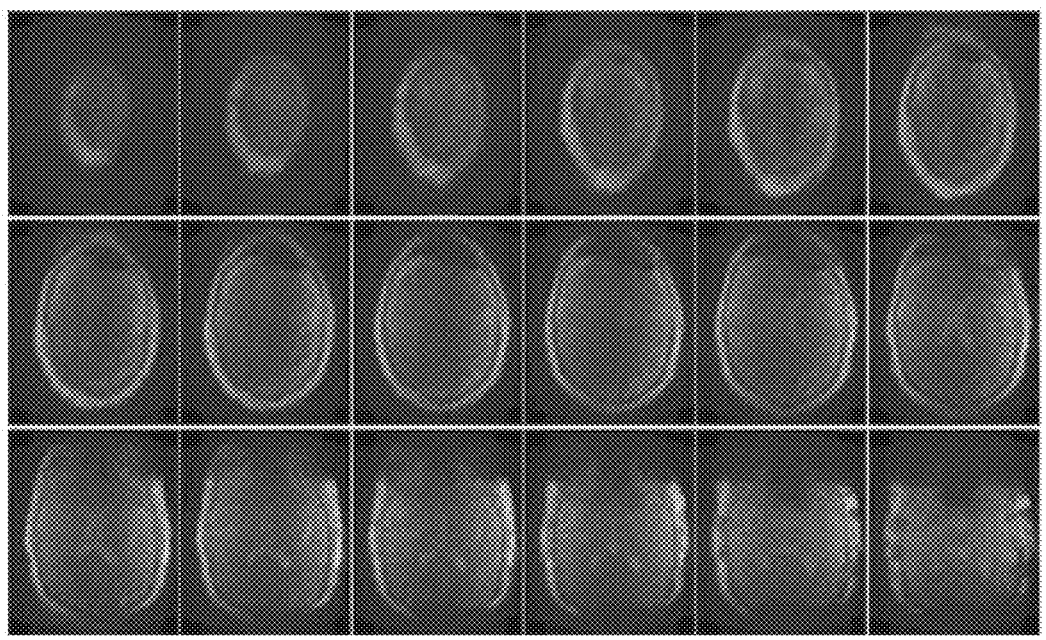
FIG. 11B illustrates the result of applying the neural network techniques described herein to correct for motion in the MR images of FIG. 11A, in accordance with some embodiments of the technology described herein.
Figure 12A:
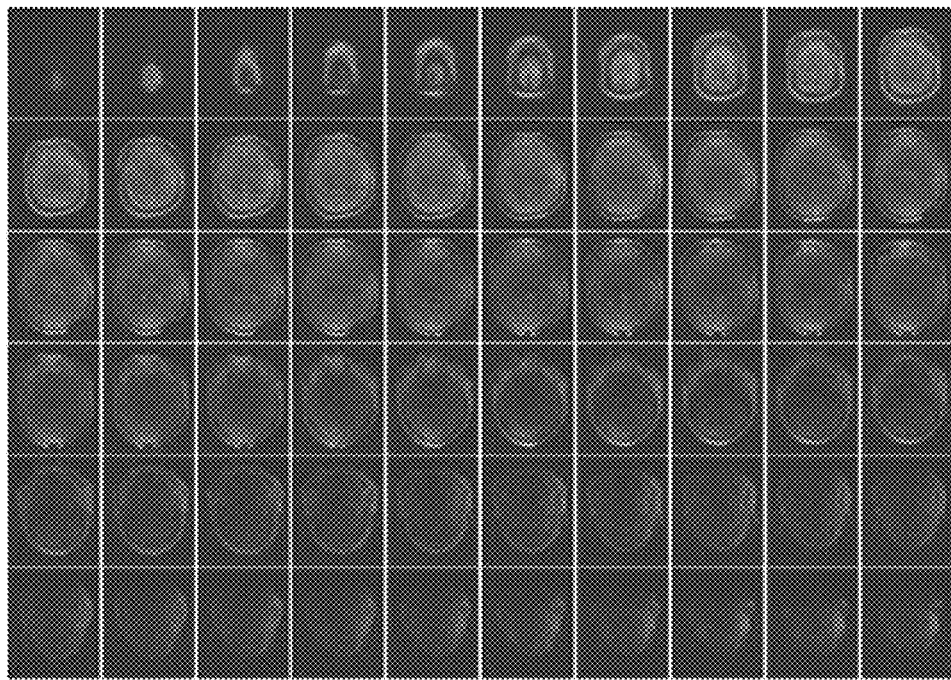
FIG. 12A illustrates another example of motion-corrupted MR images of a patient's brain.
Figure 12B:
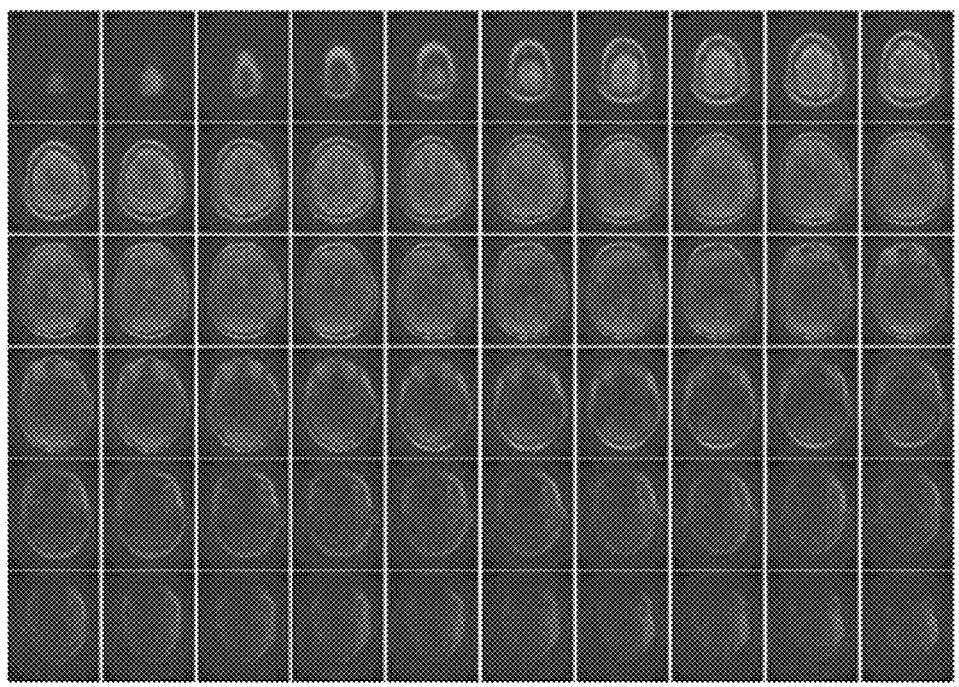
FIG. 12B illustrates the result of applying the neural network techniques described herein to correct for motion in the MR images of FIG. 12A, in accordance with some embodiments of the technology described herein.
Figure 13B:
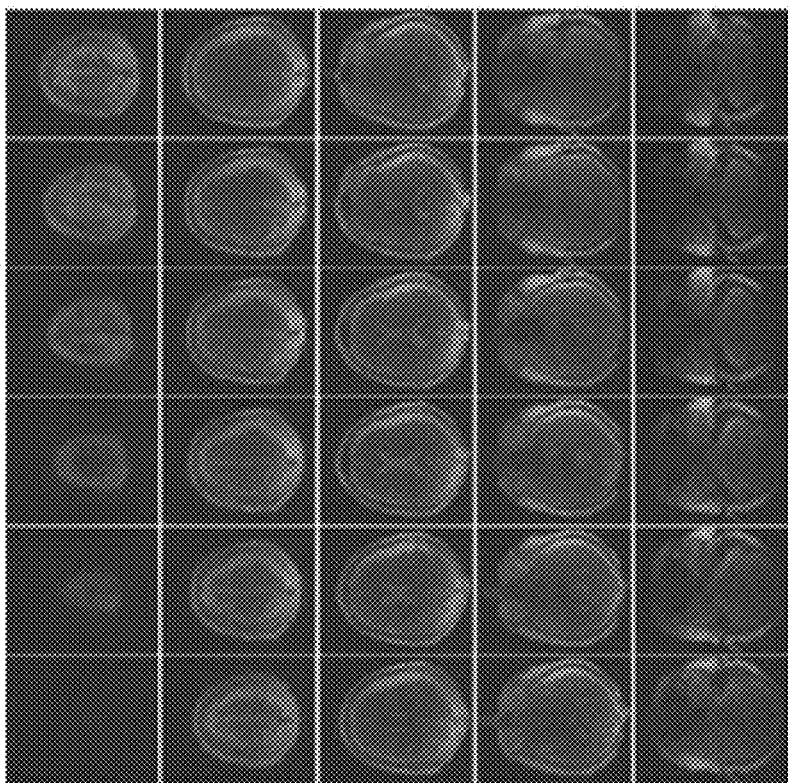
FIG. 13B illustrates the result of applying the neural network techniques described herein to correct for motion in the MR images of FIG. 13A, in accordance with some embodiments of the technology described herein.
Figure 13A:
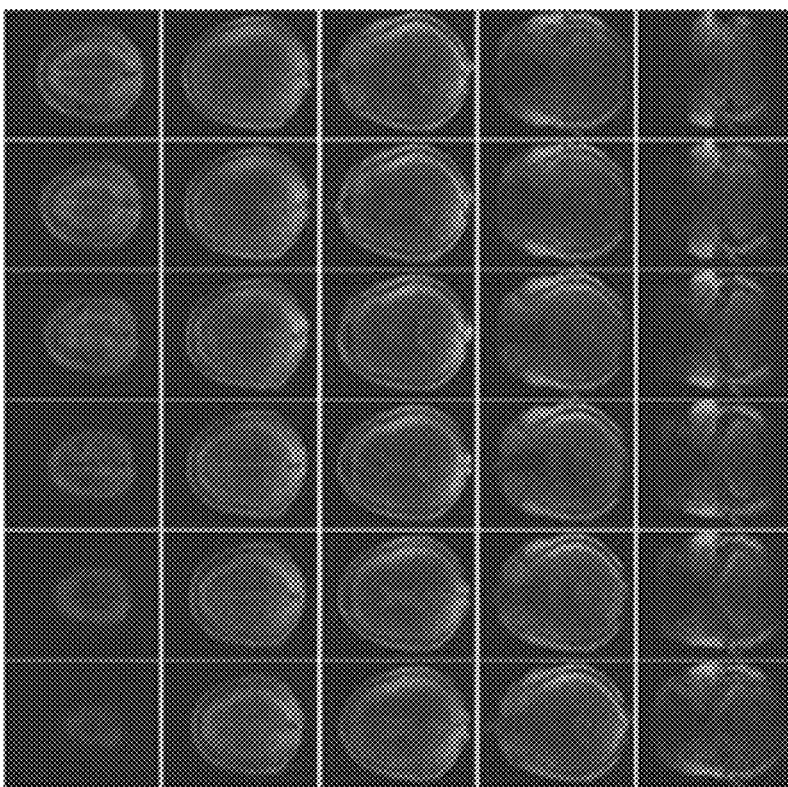
FIG. 13A illustrates motion-corrupted MR images, the motion occurring along the z-direction (out of the plane of the images).

FIGS. 11A, 12A, and 13A show examples of motion-corrupted MR images of different patients' brains. FIGS. 11A, 12A, and 13A were all acquired using a balanced steady-state free precession (bSSFP) pulse sequence using a low-field MRI system, as described herein. FIGS. 11B, 12B, and 13B show corresponding examples of motion-corrected MR images, the motion correction being performed using motion estimation and correction methods as described herein.

Figure 14B:
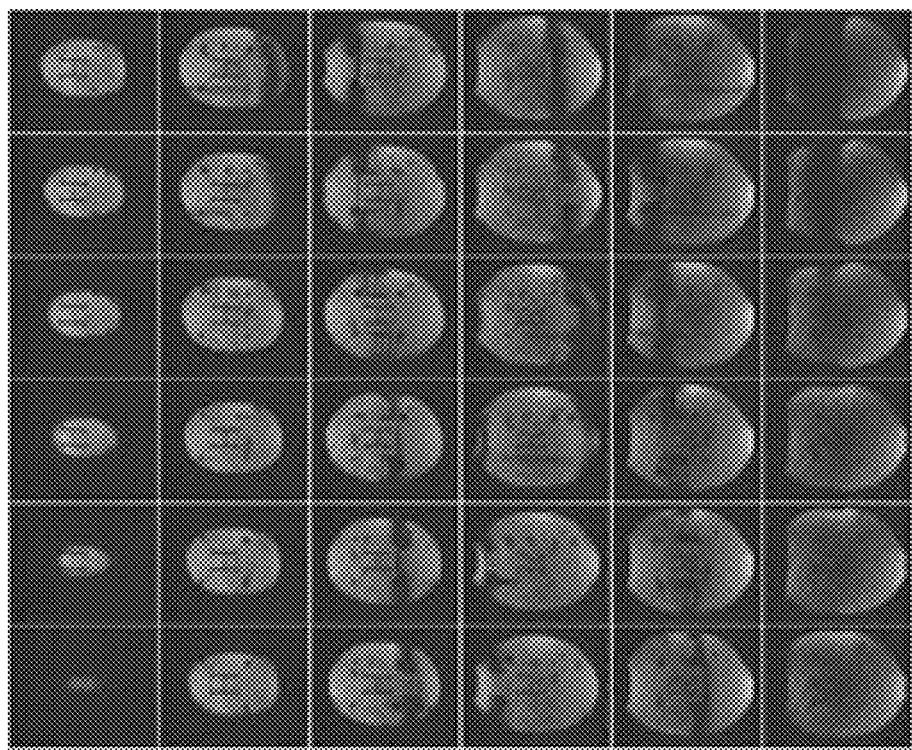
FIG. 14B illustrates the result of applying the neural network techniques described herein to the MR images of FIG. 14A, which shows that no motion is detected, no correction in performed, in accordance with some embodiments of the technology described herein.
Figure 14A:
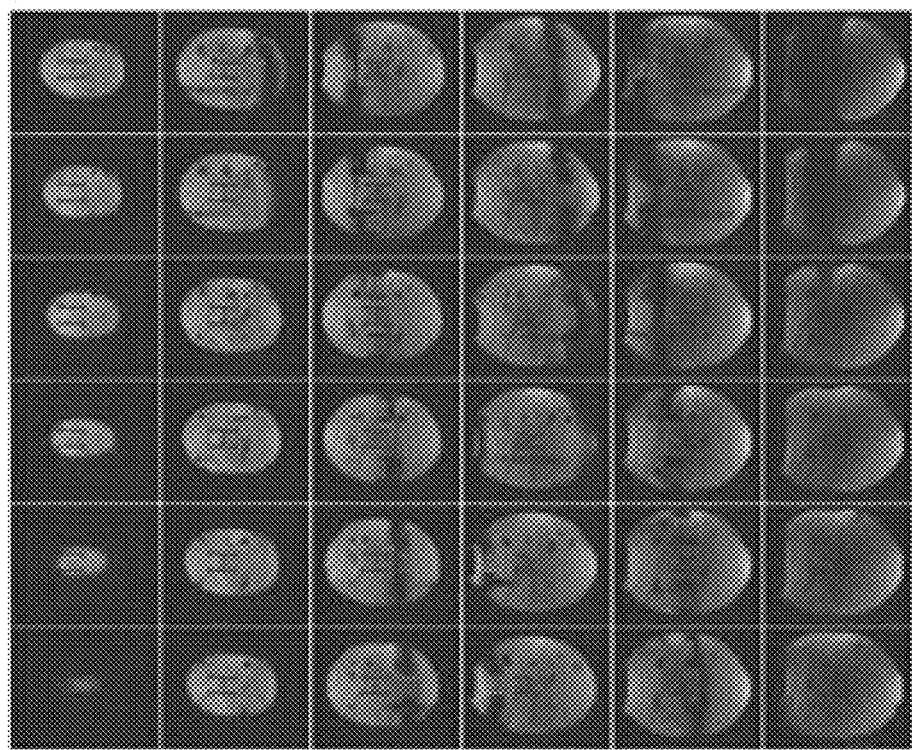
FIG. 14A illustrates MR images having no motion-corruption.

FIGS. 14A and 14B show an example of MR images of a phantom unaffected by motion. The MR images of FIG. 14B have been evaluated using the motion estimation and correction method as described herein, though as no motion was detected by the neural network model, no correction to the MR images was performed.

Self Ensembling

The inventors have developed techniques for improving non-linear MR reconstruction methods using self-ensembling. For example, in the context of MR image reconstruction using neural network models, self-ensembling may reduce or remove errors introduced by the neural network model in each MR image without requiring that additional training of the neural network model be performed.

The idea behind self ensembling is to create one or more variants of the input MR data (prior to reconstruction) by applying one or more invertible functions to the input MR data. Then the original input MR data and its variant(s) are reconstructed, inverse(s) of the invertible function(s) are applied to the reconstructed variant(s), and the resulting images are averaged.

The self-ensembling techniques described herein may suppress (e.g., reduce or eliminate) any errors introduced through the neural network reconstruction, which may result in higher-quality, higher SNR images. The self-ensembling techniques described herein are not limited to being applied in embodiments where neural networks are used to perform image reconstruction and may be applied in the context of any non-linear MR reconstruction method (e.g., compressed sensing).

Accordingly, the inventors have developed techniques for self-ensembling of MR data. Some embodiments provide for systems and methods for generating MR images of a subject from MR data obtained by an MRI system. The method comprises: (1) obtaining input MR data obtained by imaging the subject using the MRI system; (2) generating a plurality of transformed input MR data instances by applying a respective first plurality of transformations to the input MR data; (3) generating a plurality of MR images from the plurality of transformed input MR data instances and the input MR data using a non-linear MR image reconstruction technique; (4) generating an ensembled MR image from the plurality of MR images at least in part by: (a) applying a second plurality of transformations (e.g., to mitigate the effects of the first plurality of transformations in the image domain) to the plurality of MR images to obtain a plurality of transformed MR images; and (b) combining the plurality of transformed MR images to obtain the ensembled MR image; and (5) outputting the ensembled MR image. In some embodiments, a software program may perform the above-described acts. Alternately, one or more of these acts may be implemented using hardware. Accordingly, the MR image generation techniques described herein may be implemented using hardware, software, or any suitable combination.

In some embodiments, applying the first plurality of transformations to the input MR data comprises applying one or more of a selection of transformations in the spatial frequency domain. For example, the first plurality of transformations may include any one of a constant phase shift transformation, a linear phase shift transformation, a complex conjugation transformation, a rotation transformation, a transpose transformation, and/or a reflection transformation. Applying the first plurality of transformations to the input MR data may generate a plurality of transformed input MR data instances for use in self-ensembling the input MR data.

In some embodiments, using the non-linear MR image reconstruction technique comprises applying a neural network model to the transformed input MR data instances to obtain the plurality of MR images. The non-linear MR image reconstruction technique may be any suitable neural network model configured to perform MR image reconstruction. For example, the neural network model may be reconstruction neural network 212, as described in connection with FIGS. 2A and 2C.

In some embodiments, using the non-linear MR image reconstruction technique comprises using a compressed sensing (CS) technique. The non-linear MR image reconstruction technique may be any suitable CS technique configured to perform MR image reconstruction. For example, the CS technique may be any one of an iterative soft thresholding algorithm (ISTA), a sub-band adaptive iterative soft thresholding algorithm (SISTA), fast iterative soft thresholding algorithm (FISTA), energy preserving sampling (ePRESS), exponential wavelet transform (EWT), exponential wavelet transform iterative soft thresholding algorithm (EWT-ISTA), exponential wavelet iterative shrinkage thresholding algorithm (EWISTA), exponential wavelet iterative shrinkage thresholding algorithm with random shift (EWISTARS), and/or any other suitable CS techniques.

In some embodiments, applying the second plurality of transformations to the plurality of MR images comprises applying the second plurality of transformations to the plurality of MR images in an image domain. The second plurality of transformations may be selected to suppress (reduce and/or eliminate) the transformation effects of the applied first plurality of transformations in the spatial frequency domain. For example, if a linear phase shift is first applied in the spatial frequency domain, a pixel shift may be applied thereafter in the image domain to mitigate the effects of the first transformation in the spatial frequency domain. Other examples of transformation pairs include: (1) a constant phase shift in the spatial frequency domain and a constant phase shift in the image domain; (2) a conjugation of data in the spatial frequency domain and a reflection in the image domain; and (3) a rotation in the spatial frequency domain and a rotation in the image domain.

In some embodiments, combining the plurality of transformed MR images to obtain the ensembled MR image comprises computing the ensembled MR image as a weighted average of the plurality of transformed MR images. For example, the weight value of the weighted average may be determined based at least in part on the total number of varied model parameters and/or the total number of transformation functions applied to the input MR data. Alternately, the weight value of the weighted average may be based on which transformations are applied to the input MR data.

It may be desirable, in some embodiments, to remove the effects of adjacent subject anatomy slices from a reconstructed image of a single subject anatomy slice. Accordingly, the inventors have developed methods for subtracting the contribution of a neighboring slice from a given slice as a part of a self-ensembling technique. In some embodiments, where the input MR data comprises a first spatial frequency MR data ($y_i$) for generating an image for a first subject anatomy slice and second spatial frequency MR data ($y_{i+1}$) for generating an image for a second subject anatomy slice, generating the plurality of transformed input MR data instances comprises generating a first transformed input MR data instance ($y_i^{+1}$) by adding the second spatial frequency MR data to the first spatial frequency MR data. Generating the plurality of MR images comprises generating a first MR image ($x_i^{+1}$) from the first transformed data instance ($y_i^{+1}$) and generating a second MR image ($x_{i+1}$) from the second MR spatial frequency data ($y_{i+1}$). Generating the ensembled MR image then comprises subtracting the second MR image from the first MR image ($x_i^{+1} - x_{i+1}$).

In some embodiments, the input MR data may comprise multiple MR data instances, and it may be desirable to remove the effects of multiple adjacent subject anatomy slices from a reconstructed MR image of a single subject anatomy slice. In such embodiments, the input MR data may comprise first spatial frequency MR data for generating an image for a first subject anatomy slice and second spatial frequency MR data for generating one or more images for one or more other subject anatomy slices. Generating the plurality of transformed input MR data instances may then comprise generating a first transformed input MR data instance by combining the first spatial frequency MR data and the second spatial frequency MR data. Additionally, generating the plurality of MR images may comprise generating a first MR image from the first transformed input MR data instance and generating one or more second MR images from the second spatial frequency MR data. Generating the ensembled MR image may then comprise subtracting the one or more second MR images from the first MR image.

Figure 15:
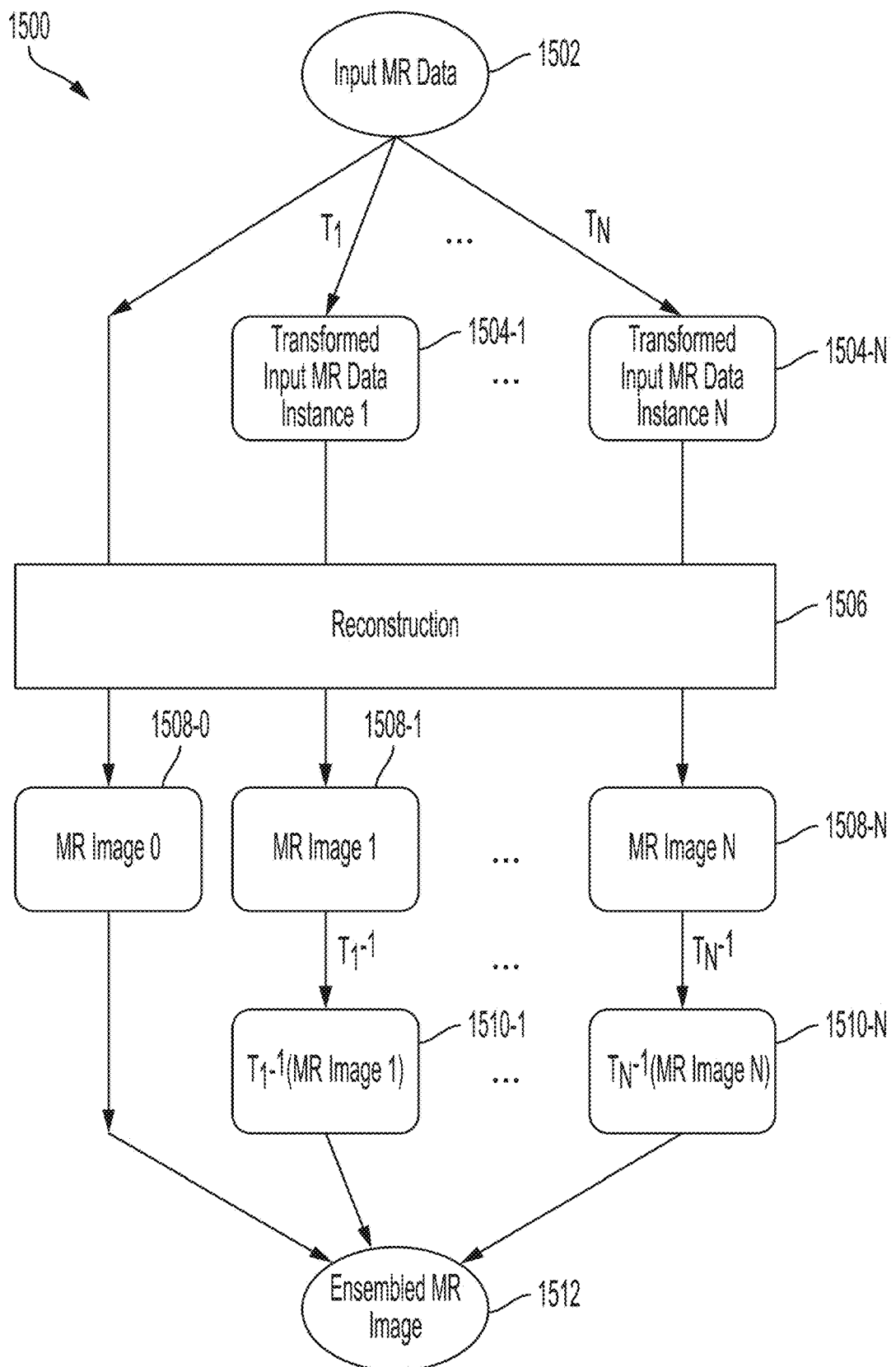
FIG. 15 is a diagram illustrating a self-ensembling approach to non-linear MR image reconstruction, in accordance with some embodiments of the technology described herein.

FIG. 15 is a diagram 1500 illustrating a self-ensembling approach to non-linear MR image reconstruction, in accordance with some embodiments of the technology described herein. The self-ensembling technique may be executed by any suitable computing device. For example, in some embodiments, the self-ensembling technique may be performed by a computing device co-located (e.g., in the same room) with an MRI system that obtained the MR data by imaging a subject (or object). As another example, in some embodiments, the self-ensembling technique may be performed by one or more processors located on the MRI system that obtained the MR data. Alternately, in some embodiments, the self-ensembling technique may be performed by one or more processors located remotely from the MRI system (e.g., as part of a cloud computing environment) that obtained the input MR data.

The self-ensembling technique begins with an instance of input MR data 1502, in some embodiments. The input MR data 1502 may be obtained by an MRI system (including any MRI systems as described herein) using any suitable pulse sequence. Any suitable pre-processing may be performed to input MR data 1502 prior to self-ensembling. The input MR data 1502 may represent a single corresponding MR image in the image domain (e.g., the input MR data 1502 may represent a single MR data gathering instance). In some embodiments, the input MR data 1502 may represent a single anatomy slice of the imaged subject (or object).

The input MR data 1502 may be transformed by transformations $T_1 \ldots T_N$ to form transformed input MR data instances 1504-1 through 1504-N, in some embodiments. Transformations $T_1 \ldots T_N$ may be any suitable transformation function configured to alter the input MR data 1502. For example, transformations $T_1 \ldots T_N$ may be any one of a non-limiting group of transformations, including linear phase shift transformations, constant phase shift transformations, complex conjugation transformations, rotation transformations, transpose transformations, and/or reflection transformations. In some embodiments, the transformations $T_1 \ldots T_N$ may include the identity transformation. Alternatively, an instance of the input MR data 1502 may be preserved (e.g., no transformation may be applied to the $0^{th}$ instance of input MR data 1502 prior to MR image reconstruction).

In some embodiments, the transformed input MR data instances 1504-1 through 1504-N may be reconstructed to form a plurality of MR images 1508-0 through 1508-N. The MR image reconstruction may be performed by a non-linear MR image reconstruction process 1506, represented by:

$$x = f(y)$$

where y is the MR data in the spatial frequency domain, $f(\cdot)$ is the non-linear reconstruction function, and x is the reconstructed MR image in the image domain.

The non-linear MR image reconstruction process 1506 may be any suitable non-linear MR image reconstruction technique. In some embodiments, the non-linear MR image reconstruction process 1506 may be a neural network model configured to perform MR image reconstruction. For example, the neural network model may be reconstruction neural network 212, as described in connection with FIGS. 2A and 2C. Alternatively, in some embodiments, the non-linear MR image reconstruction process 1506 may be any suitable CS technique, examples of which are described herein.

In some embodiments, reverse transformations $T_1^{-1} \ldots T_N^{-1}$ may be applied to the plurality of MR images 1508-0 through 1508-N to form transformed MR images 1508-0 through 1508-N. In some embodiments, the reverse transformations may include the identity transformation, which may be applied to MR image 1508-0. Alternatively, MR image 1508-0 may be preserved (e.g., no reverse transformation may be applied to MR image 1508-0 prior to ensembling).

It is to be appreciated that because a non-linear MR reconstruction technique is employed between the transformations $T_1 \ldots T_N$ performed in the spatial frequency domain and the reverse transformations $T_1^{-1} \ldots T_N^{-1}$ performed in the imaging domain, that the reverse transformations $T_1^{-1} \ldots T_N^{-1}$ are not, strictly, inverse transformations of transformations $T_1 \ldots T_N$. Rather, reverse transformations $T_1^{-1} \ldots T_N^{-1}$ are selected to at least partially reverse and/or mitigate the effects of transformations $T_1 \ldots T_N$ in the image domain. For example, if a linear phase shift is first applied in the spatial frequency domain, a pixel shift may be applied thereafter in the image domain to mitigate the effects of the first transformation in the spatial frequency domain. Other examples of transformation pairs include: (1) a constant phase shift in the spatial frequency domain and a constant phase shift in the image domain; (2) a conjugation of data in the spatial frequency domain and a reflection in the image domain; and (3) a rotation in the spatial frequency domain and a rotation in the image domain.

After obtaining a transformed MR images 1508-0 through 1508-N, an ensembled MR image 1512 may be formed, in some embodiments. The ensembled MR image 1512 may be represented mathematically as:

$$x_{self\text{-}ensemble} = \Sigma_i^N w_i T_i^{-1} f(T_i y)$$

where N is the total number of transformation functions $T_i$, and $w_i$ is the weight for the given reconstruction. In some embodiments, the weight $w_i$ may be based on the total number of transformation functions (e.g., $w_i = 1/N$). Alternatively, the weight $w_i$ may be based on the particular transformation functions applied.

When the non-linear MR image reconstruction process 1506 is performed by using a neural network model, additional parameters, $\theta$, may be varied, such that the MR image reconstruction may be mathematically described by:

$$x = f(y|\theta)$$

and the ensembled MR image 1512 may be represented mathematically $$x_{self\text{-}ensemble} = \Sigma_j^M \Sigma_i^N w_{ij} T_i^{-1} f(T_i y|\theta_j)$$

where M is the total number of varied model parameters, $\theta$, and with $w_{ij}$ is the weight for the given reconstruction. In some embodiments, the weight $w_{ij}$ may be based on the total number of transformation functions and the total number of varied model parameters (e.g., $w_{ij} = 1/NM$). Alternatively, the weight $w_{ij}$ may be based on the particular transformation functions applied.

In some embodiments, it may be desirable to reduce or eliminate noise introduced into an MR image of a particular subject anatomy slice by one or more neighboring subject anatomy slices. Such noise contributions may be addressed within the context of self-ensembling, as described herein, by using a "Mix-Up" technique and introducing the following transformation function to a given first input MR data, $y_i$:

$$y_i^{+1} = T(y_i) = y_i + y_{i+1}$$

where $y_{i+1}$ is a subject anatomy slice proximate to slice $y_i$.

The non-linear MR image reconstruction process 1506 may then be mathematically described as, for any non-linear reconstruction f(y):

$$x_i^{+1} = f(y_i^{+1}), x_{i+1} = f(y_{i+1})$$

or, for a neural network model with additional parameters, $\theta$:

$$x_i^{+1} = f(y_i^{+1}|\theta), x_{i+1} = f(y_{i+1}|\theta)$$

After MR image reconstruction, reverse transformations may be applied to the reconstructed MR images to subtract the contribution of the one or more adjacent subject anatomy slices:

$$x_i^1 = T^{-1}(x_i^{+1}) = x_i^{+1} - x_{i+1}$$

In some embodiments, one may generate many images, $x_i^1$, using any suitable number of adjacent subject anatomy slices (e.g., slices $y_{i+1} \ldots y_{i+n}$), which may be added to slice $y_i$ as a part of transform $T(y_i)$. In such embodiments, the final ensembled image may be obtained by:

$$x_{self\text{-}ensemble} = \Sigma_j^N x_i^j.$$

Figure 16:
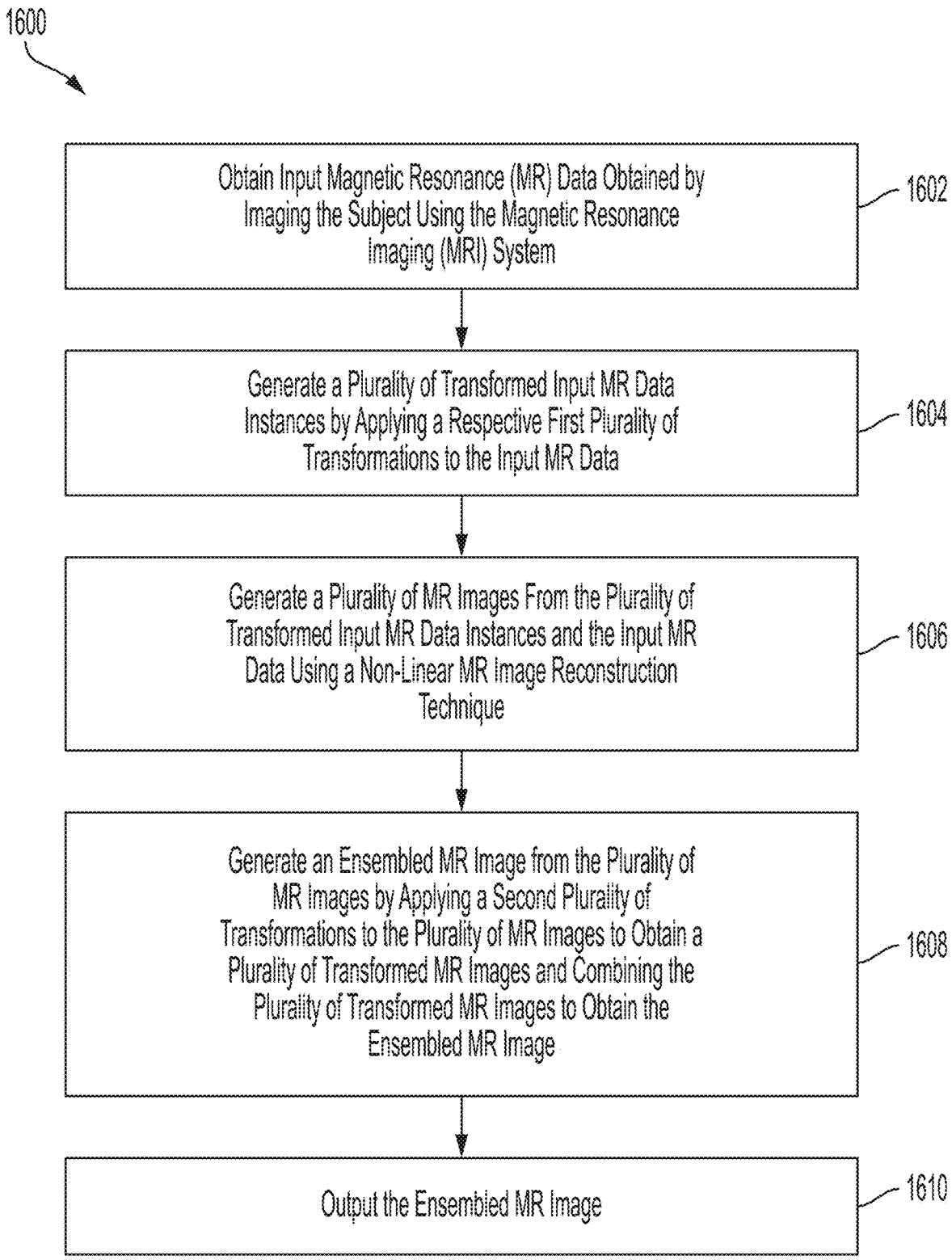
FIG. 16 is a flowchart of an illustrative process 1600 for performing non-linear MR image reconstruction using self ensembling, in accordance with some embodiments of the technology described herein.

FIG. 16 is a flowchart of an illustrative process 1600 for performing non-linear MR image reconstruction using self ensembling, in accordance with some embodiments of the technology described herein. Process 1600 may be executed using any suitable computing device. For example, in some embodiments, the process 1600 may be performed by a computing device co-located (e.g., in the same room) with an MRI system that obtained the MR data by imaging a subject (or object). As another example, in some embodiments, the process 1600 may be performed by one or more processors located on the MRI system that obtained the MR data. Alternately, in some embodiments, the process 1600 may be performed by one or more processors located remotely from the MRI system (e.g., as part of a cloud computing environment) that obtained the input MR data.

Process 1600 begins at act 1602, where input MR data in obtained. In some embodiments, the input MR data had been previously obtained by an MRI system and stored for subsequent analysis, so that it is accessed at act 1602. In other embodiments, the input MR data may be obtained by an MRI system (including any of the MRI systems described herein) as part of process 1600.

In some embodiments, one or more pre-processing steps may be performed prior to moving to act 1604, where a plurality of transformed input MR data is generated by applying a respective first plurality of transformations to the input data. The transformations of the respective first plurality of transformations may be any suitable transformations in the spatial frequency domain configured to alter the input MR data. For example, the transformations of the respective first plurality of transformations may be the transformations $T_1 \ldots T_N$ as described in connection with FIG. 15 herein.

After act 1604, the process 1600 may move to act 1606, where a plurality of MR images may be generated from the plurality of transformed input MR data instances and the input MR data using a non-linear MR image reconstruction technique. The non-linear MR image reconstruction technique used to generate the plurality of MR images may be any suitable non-linear MR image reconstruction technique, as described herein. In some embodiments, the non-linear MR image reconstruction process 1506 may be a neural network model configured to perform MR image reconstruction. For example, the neural network model may be reconstruction neural network 212, as described in connection with FIGS. 2A and 2C. Alternatively, in some embodiments, the non-linear MR image reconstruction process 1506 may be any suitable CS technique, as described herein.

After act 1606, the process 1600 may move to act 1608, where an ensembled MR image may be generated from the plurality of MR images, in some embodiments. The ensembled MR image may be generated at least in part by applying a second plurality of transformations to the plurality of MR images to obtain a plurality of transformed images. The second plurality of transformations may include any suitable transformations to reverse and/or mitigate the effects of the first plurality of transformations in the image domain, as described herein. The ensembled MR image may also be generated at least in part by combining the plurality of transformed MR images to obtain the ensembled MR image, in some embodiments. Combining the plurality of transformed MR images to obtain the ensembled MR image may comprise, for example, performing an average or a weighted average (e.g., adding images weighted by positive and/or negative weights), as described herein.

After act 1608, the process 1600 may move to act 1610, where the ensembled MR image may be output. The ensembled MR image may be output using any suitable method. For example, the ensembled MR image may be output by being saved for subsequent access, transmitted to a recipient over a network, and/or displayed to a user of the MRI system.

Figures 17A, 17B:
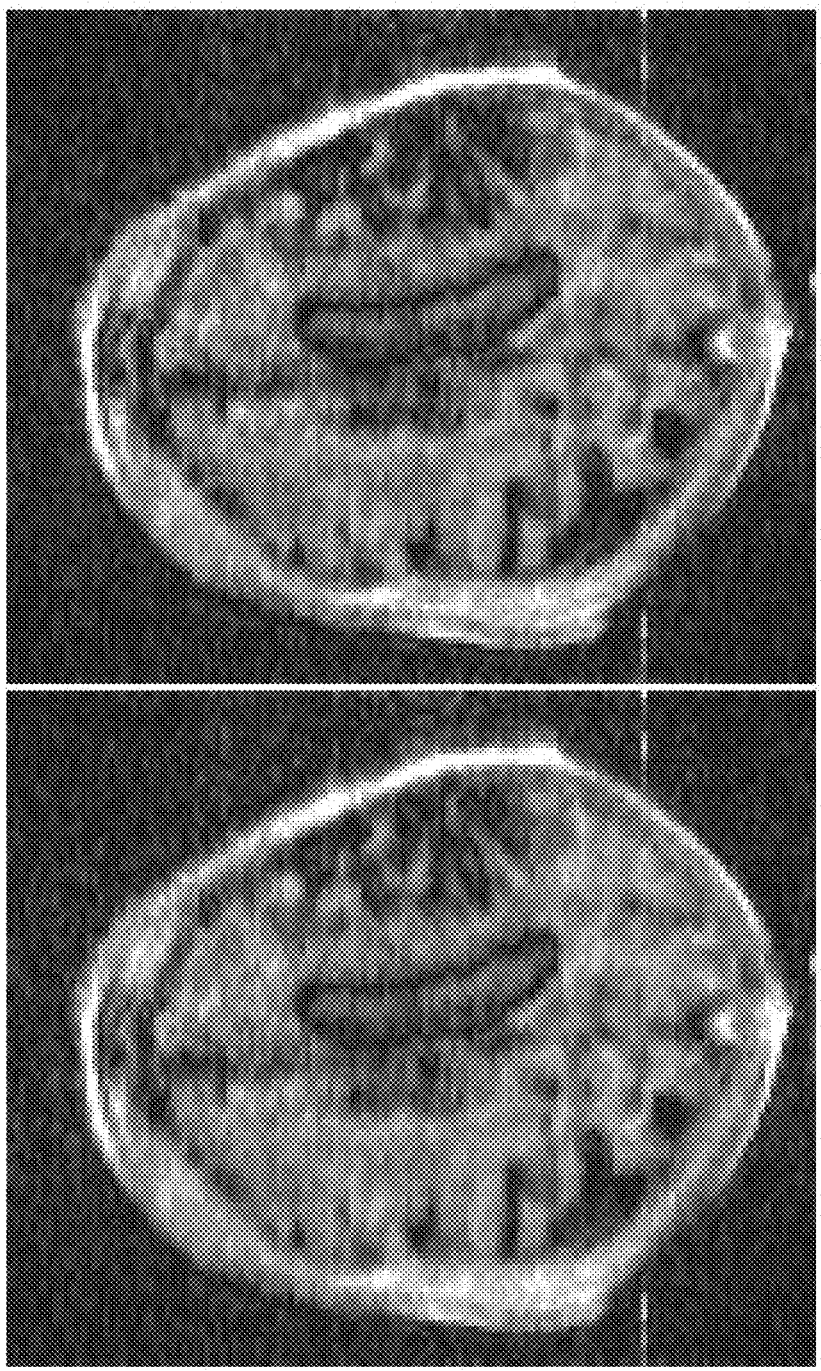
FIGS. 17A and 17B show example MR images of a subject's brain obtained without self-ensembling and with self-ensembling, respectively, in accordance with some embodiments of the technology described herein.

FIGS. 17A and 17B show example MR images of a subject's brain obtained without self-ensembling and with self-ensembling, respectively. The Mix-Up self-ensembling technique is used to produce FIG. 17B, which results in an MR image having sharper contrast as compared to the image reconstruction of FIG. 17A obtained without self ensembling.

Figures 18A, 18B:
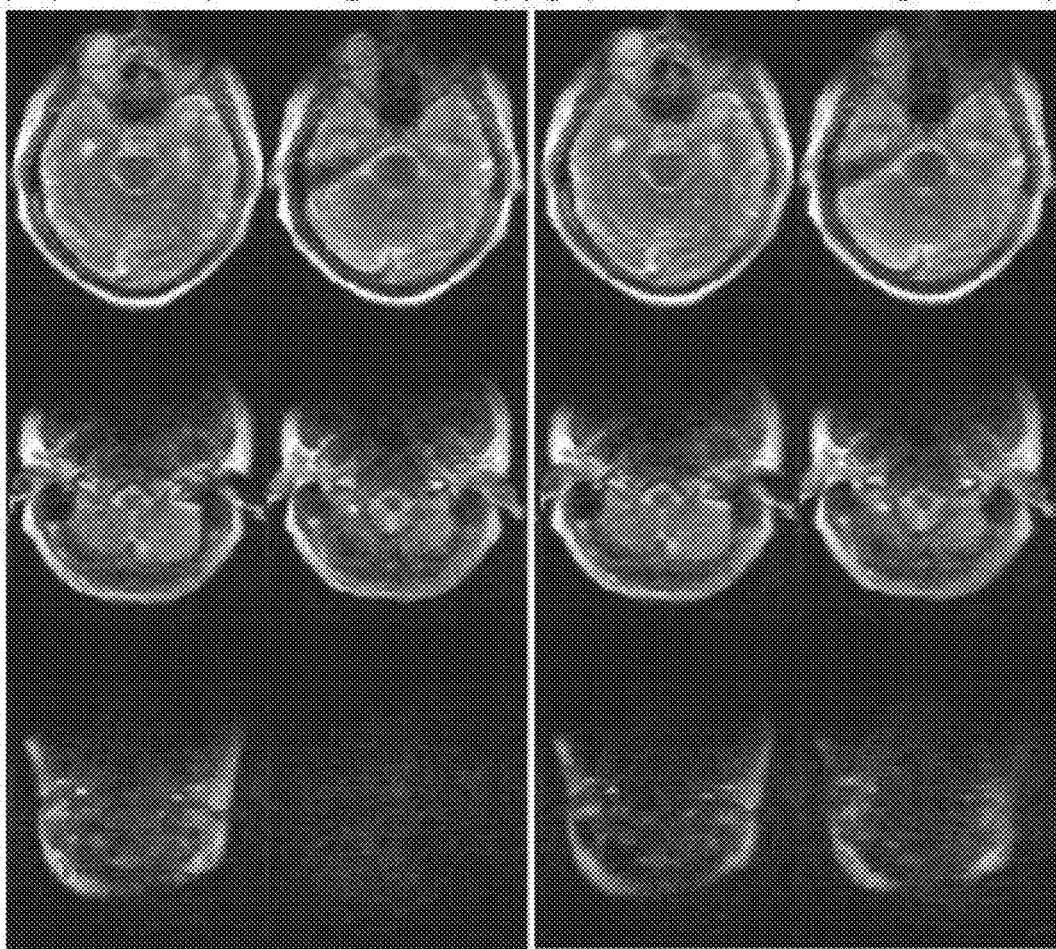
FIGS. 18A and 18B show example MR images of a subject's brain obtained (by different RF coils) without self-ensembling and with self-ensembling, respectively, in accordance with some embodiments of the technology described herein.

FIGS. 18A and 18B show example MR images of a subject's brain obtained (e.g., by different RF coils) without self-ensembling and with self-ensembling, respectively. The self-ensembling technique used to produce FIG. 18B is performed using geometrical data augmentation. In some such embodiments, the transformations used in self-ensembling may include a complex conjugation transformation in the spatial frequency domain and a reflection in the image domain. The example of FIG. 18B employed the following example transformations in the spatial frequency domain:

$T_0$=identity function
$T_1$=complex conjugation and the following transformations in the image domain:

$T_0^{-1}$=reverse identity function
$T_1^{-1}$=reflection to perform the following self-ensembling:

$x_{self\text{-}ensemble} = \Sigma_i^2 0.5 T_i^{-1} f(T_i y | \theta)$.

Figures 19A, 19B:
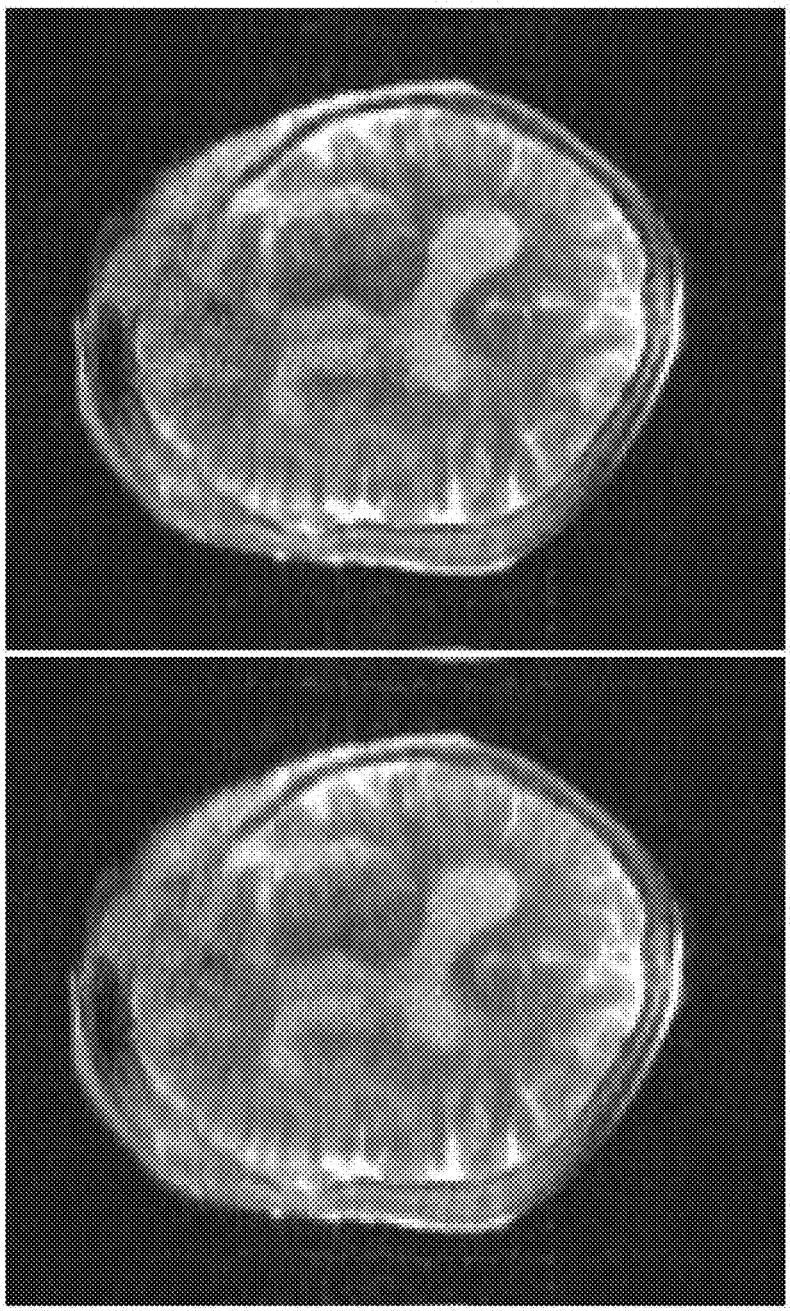
FIGS. 19A and 19B show example MR images of a subject's brain obtained without self-ensembling and with self-ensembling, respectively, in accordance with some embodiments of the technology described herein.

FIGS. 19A and 19B show example MR images of a subject's brain obtained without self-ensembling and with self-ensembling, respectively. The self-ensembling technique used to produce FIG. 19B includes the Mix-Up technique and geometrical data augmentation, as described herein. As may be observed from FIGS. 18A-B and 19A-B, self-ensembling produces sharper reconstructions having a higher contrast.

Coil Estimation

As described herein, in some embodiments, an MRI system may include multiple RF coils configured to detect MR data while the MRI system is imaging a subject. In such embodiments, the MR data obtained from each of the multiple RF coils may be combined to generate one or more images of the subject.

For example, in some embodiments, multiple MR images may be generated from spatial frequency data collected by a respective plurality of RF coils, and the multiple MR images may be combined to generate a single image of the subject. This is sometimes termed "parallel imaging". For example, starting with $N_{coil}$ MR images: $x_i, \ldots, x_{N_{coil}}$, these images may be combined using the following weighted combination, for each pixel location r in the image x(r):

$$x = \sum_{i=1}^{N_{coil}} \frac{s_i^* x_i}{\sum_{j=1}^{N_{coil}} s_j^* s_j}$$

where $(\cdot)^*$ denotes complex conjugation, where $S_j$ represents the profile of the jth RF coil, and where the index r is suppressed for clarity. The coil profile $S_j$ for the jth RF coil may indicate the sensitivity of the jth coil to MR signals at various locations in the field of view. For this reason, a coil profile may sometimes be termed a coil sensitivity profile. In some embodiments, a coil profile may be specified at a per-pixel or per-voxel level, each entry indicative of the sensitivity of a coil to MR signals emitted from that pixel or voxel. The sensitivity of a coil may be a higher for a pixel/voxel closer to the coil than for a pixel/voxel in a region far from the coil.

In situations where the noise correlation L is known (e.g., is an $N_{coil} \times N_{coil}$ matrix), the individual images, one per coil, may be combined according to the following equation in matrix form (again pixel-wise for each r):

$x = (\hat{S}^H L^{-1} \hat{S})^{-1} \hat{S}^H L^{-1} \hat{x}$ where $\hat{x}=[x_1, \ldots, x_{N_{coil}}]$, $\hat{S}=[S_1, \ldots, S_{N_{coil}}]$ for each pixel location.

Parallel imaging is a popular reconstruction technique because the resulting combined image has a higher signal-to-noise ratio than the constituent RF coil images. When the RF coil profiles are known in advance, then the combination equations described above are optimal estimates of the combined image in a least-squares sense (or in the maximum likelihood sense under a Gaussian noise assumption). The above equations can be used when the RF coil profiles are known. When the RF coil profiles are not known, not the images may be computed according to a residual sum of squares (RSS) technique, but this results in a lower-quality and lower-SNR image.

Accordingly, in some embodiments, the inventors have developed a neural network model (e.g., the neural network model shown in FIG. 20B) for estimating the sensitivity profile of an RF coil from data collected by the RF coil. The sensitivity profiles estimated by the neural network may be used to combine images obtained during parallel imaging with multiple RF coils to obtain combined images of a subject. The resulting neural-network based parallel imaging technique developed by the inventors outperforms both conventional parallel imaging based on residual sum of squares estimates of coil sensitivity and the adaptive reconstruction technique described in D. O. Walsh, A. F. Gmitro, and M. W. Marcellin, "Adaptive Reconstruction of Phased Array MR Imagery," Magnetic Resonance in Medicine 42:682-690 (2000).

Accordingly, some embodiments provide for a method for generating magnetic resonance (MR) images from MR data obtained by an MRI system comprising a plurality of RF coils (e.g., 8, 16, 32, etc.) configured to detect RF signals. The method includes: (A) obtaining a plurality of input MR datasets (e.g., 8, 16, 32, etc.) obtained by the MRI system while imaging a subject, each of the plurality of input MR datasets comprising spatial frequency data and obtained using a respective RF coil in the plurality of RF coils; (B) generating a respective plurality of MR images from the plurality of input MR datasets by using an MR image reconstruction technique (e.g., using a neural network, compressed sensing, a non-uniform Fourier transformation, a Fourier transformation, etc.); (C) estimating, using a neural network model, a plurality of RF coil profiles corresponding to the plurality of RF coils; (D) generating an MR image of the subject using the plurality of MR images and the plurality of RF coil profiles; and (E) outputting the generated MR image.

In some embodiments, generating the MR image of the subject using the plurality of MR images and the plurality of RF coil profiles comprises generating the MR image of the subject as a weighted combination of the plurality of MR images, each of the plurality of MR images being weighted by a respective RF coil profile in the plurality of RF coil profiles. In some embodiments, the plurality of MR images comprises a first MR image generated from a first input MR dataset obtained using a first RF coil of the plurality of RF coils, and wherein generating the MR image of the subject comprises weighting different pixels of the first MR image using different values of a first RF coil profile among the plurality of RF coil profiles, the first RF coil profile being associated with the first RF coil.

In some embodiments, the neural network may be a convolutional neural network. The neural network may be a 2D or a 3D convolutional neural network. The neural network may include one or more convolutional layers, one or more non-linearity layers (e.g., rectified linear unit layers), and/or one or more fully connected layers. In some embodiments, the neural network's input may be (e.g., complex-valued) input obtained from MR measurements detected by an RF coil (e.g., not just the magnitude of the reconstructed image, but both the magnitude and the phase) and the output may be the sensitivity profile for the RF coil.

Figure 20A:
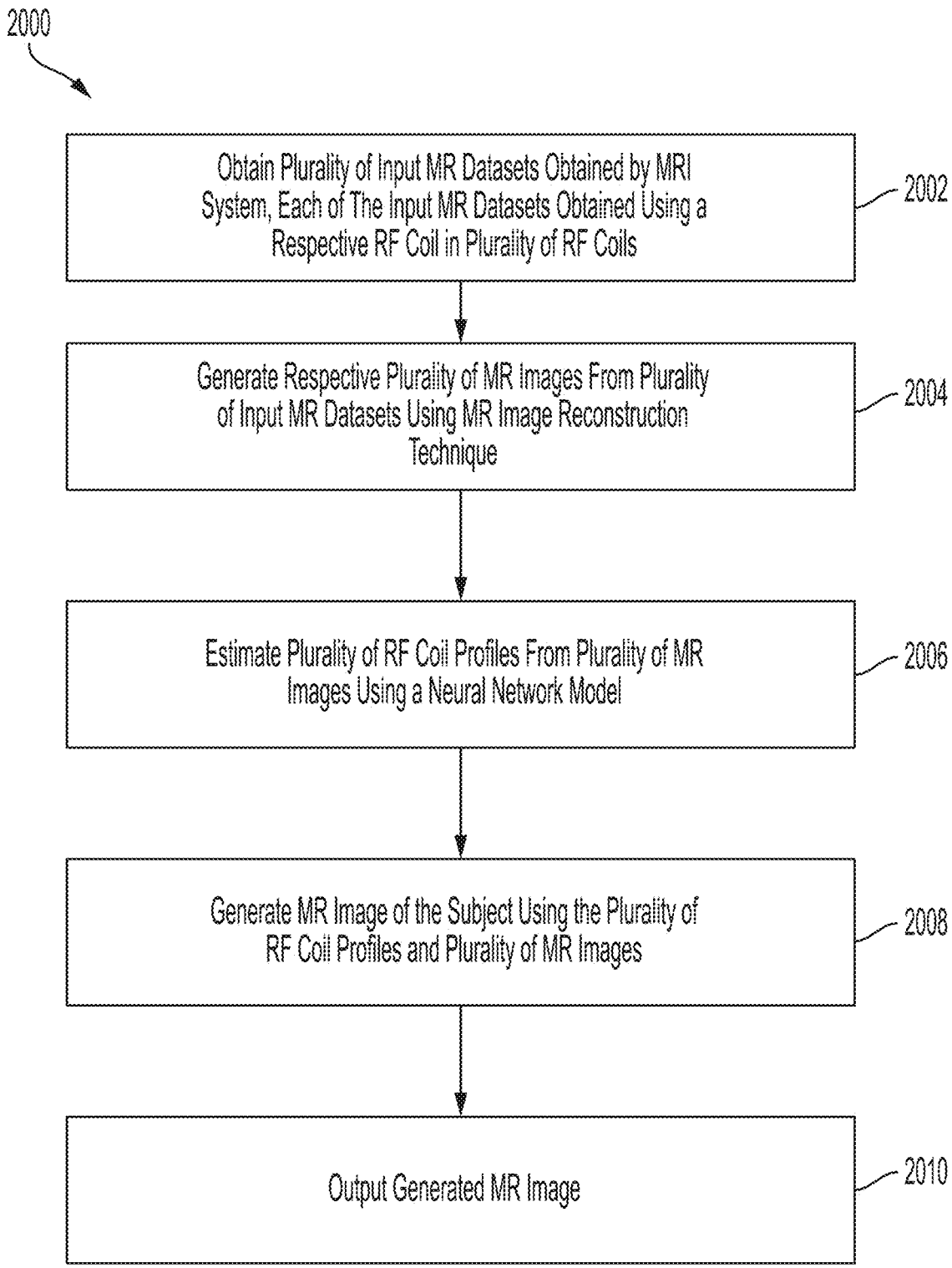
FIG. 20A is a flowchart of an illustrative process 2000 for generating an MR image from input MR spatial frequency data collected by multiple RF coils, the process including estimate RF coil profiles using a neural network, in accordance with some embodiments of the technology described herein.
Figure 20B:
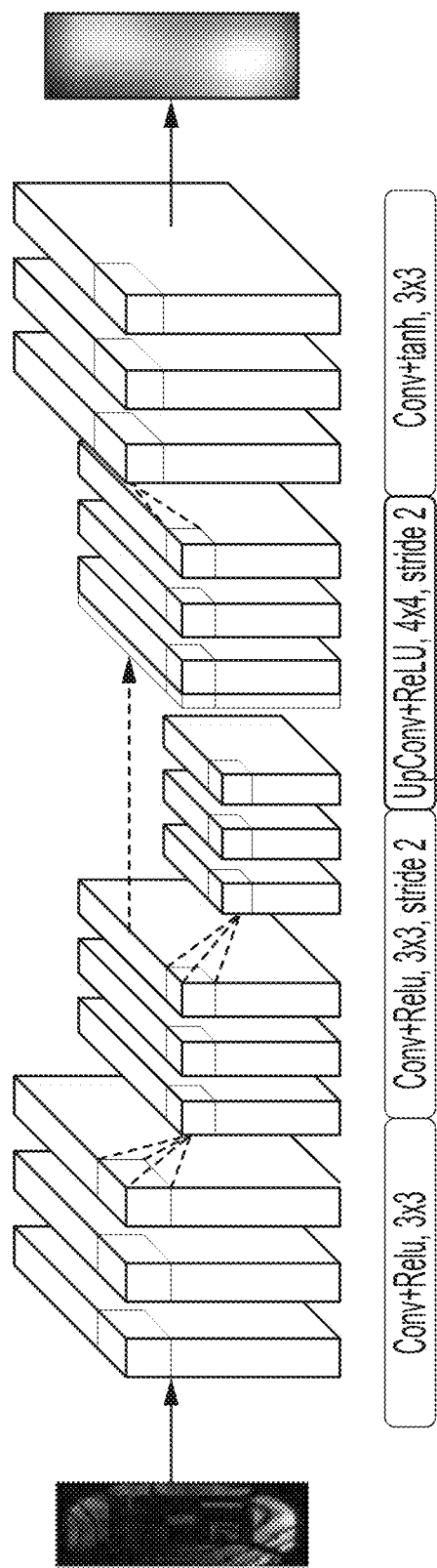
FIG. 20B is an illustrate example architecture of a neural network for estimating RF coil profiles, in accordance with some embodiments of the technology described herein.

An illustrative example of a neural network architecture that may be used for estimating coil profiles, in some embodiments, is shown in FIG. 20B. This is a 2D convolutional neural network having the following layers and associated parameters:

Layer 1: 2D convolution, kernel size=3×3, stride=1, 64 features, ReLU
Layer 2: 2D convolution, kernel size=3×3, stride=1, 64 features, ReLU
Layer 3: 2D convolution, kernel size=3×3, stride=2, 64 features, ReLU
Layer 4: 2D convolution, kernel size=3×3, stride=1, 128 features, ReLU
Layer 5: 2D convolution, kernel size=3×3, stride=1, 128 features, ReLU
Layer 6: 2D convolution, kernel size=3×3, stride=2, 128 features, ReLU
Layer 7: 2D convolution, kernel size=3×3, stride=1, 256 features, ReLU
Layer 8: 2D convolution, kernel size=3×3, stride=1, 256 features, ReLU
Layer 9: 2D convolution, kernel size=3×3, stride=1, 256 features, ReLU
Layer 10: 2D transposed convolution, kernel size=4×4, stride=2, 64 features, ReLU
Concatenate output from Layer 6 and Layer 10
Layer 12: 2D convolution, kernel size=3×3, stride=1, 64 features, ReLU
Layer 13: 2D convolution, kernel size=3×3, stride=1, 64 features, ReLU
Layer 14: 2D transposed convolution, kernel size=4×4, stride=2, 64 features, ReLU
Layer 15: 2D convolution, kernel size=3×3, stride=1, 64 features, ReLU
Layer 16: 2D convolution, kernel size=3×3, stride=1, 64 features, ReLU
Layer 17: 2D convolution, kernel size=3×3, stride=1, 64 features, Tanh A neural network, like the network of FIG. 20B, for estimating coil profiles may be trained in any of numerous ways. In some embodiments, training the neural network may comprise generating training data by simulating complex phase for various MR images and training the neural network to predict the coil profile from complex-valued image data. In some embodiments, the neural network may take as input individual coil reconstructions and produce the corresponding estimated coil profile $S_{rec-i}=f_{cnn}(x_{rec-i}|\theta)$, or take all $N_{coil}$ input and produce $N_{coil}$ sensitivity profiles jointly. Given the dataset $\mathcal{D}$ that contains the coil weighted images $x_1, \ldots, x_{N_{coil}}$ and the ground truth sensitivity maps $S_1, \ldots S_{N_{coil}}$, the network can be trained using the following loss function:

$$\mathcal{L}(\theta) = \sum_{j=1}^{|\mathcal{D}|} \sum_{i=1}^{N_{coil}} \left\| S_i^{(j)} - S_{rec-i}^{(j)} \right\|_2$$

Alternatively, in some embodiments, a neural network may be trained to directly obtain a coil combination. Let $f_{cnn}(\cdot|\theta)$ express a convolutional neural network, where the input to the network is $N_{coil}$ reconstructed images $x_{rec-1}, \ldots, x_{rec-N_{coil}}$. The network output is a complex-valued combined image $x_{combined}$. In such a situation, the loss function can be expressed as:

$$\mathcal{L}(\theta) = \sum_{j=1}^{|\mathcal{D}|} \left\| x^{(j)} - x_{combined}^{(j)} \right\|_2$$

In this alternative approach, the sensitivity profile is implicitly learnt, and the network will perform optimal combination based on the data.

In some embodiments, training data for training a neural network for estimating coil profiles may be generated synthetically from a dataset of existing MR scans. For example, in some embodiments, an MR image x may be loaded from a dataset and random phase may be added to this image to obtain a complex-valued image (since only magnitudes are typically available in existing datasets). Complex-valued coil profiles $S_i$ for $N_{coil}$ coils may be synthesized next. For example, the sensitivity values for particular pixels/voxels may be sampled according to a Gaussian distribution and random phase may be added. Next, Gaussian noise $e_i$ may be added (potentially with a simulated noise correlation matrix) to obtain simulated coil images $x_i$ according to:

$x_i = S_i x + e_i$ for $i=1 \ldots N_{coil}$.

The resulting images $x_i$ may be transformed to the spatial frequency domain and, optionally, undersampled to simulate the type of sampling trajectories that might be expected to be used in practice. This simulation process may be repeated for any suitable number of images from the data set (of e.g., brain scans or any other type of MR scans).

FIG. 20A is a flowchart of an illustrative process 2000 for generating an MR image from input MR spatial frequency data collected by multiple RF coils, in accordance with some embodiments of the technology described herein. Process 2000 may be performed by any suitable computing device(s). For example, process 2000 may be performed by one or more processors (e.g., central processing units and/or graphics processing units) part of the MRI system and/or by one or more processors external to the MRI system (e.g., computers in an adjoining room, computers elsewhere in a medical facility, and/or on the cloud).

Process 2000 begins at act 2002, where a plurality of input MR datasets previously obtained by an MRI system are accessed. The MRI system includes multiple RF coils (say "N" coils, without loss of generality), and each of the plurality of input MR data sets includes data collected by a respective RF coil from among the multiple RF coils.

Next, process 2000 proceeds to act 2004, where a plurality of MR images are generated from the plurality of input datasets obtained at act 2002 using an MR image reconstruction technique. Any suitable MR image reconstruction technique may be used. For example, the reconstruction may be performed using any neural network reconstruction technique described herein (e.g., using neural network 212). As another example, the reconstruction may be performed using compressed sensing and/or any other suitable type of non-linear reconstruction technique. As yet another example, the reconstruction may be performed using a uniform or a non-uniform Fourier transformation. The plurality of MR images may include both magnitude and phase information (they may be complex-valued).

Next, at act 2006, estimates of the plurality of RF coil profiles are generated by providing the plurality of MR images as input to a neural network model. In some embodiments, the estimates of the RF coil profiles may be generated jointly—the plurality of MR images generated at act 2004 are simultaneously provided as input to the neural network model. In other embodiments, the estimates of the RF coil profiles may be generated separately—a profile for a particular RF coil may be generated by applying a neural network to an image generated from data collected by the particular RF coil. Examples of neural network models that may be applied at act 2006 are described herein including with reference to FIG. 20B. In some embodiments, the output of the neural network may be smoothed (e.g., using a median or Gaussian filter) prior to being used at act 2008.

Next, at act 2008, the plurality of MR images are combined to generate an image of the subject using the RF coil profiles generated at act 2006. This may be done in any suitable way. For example, the combined image of the subject may be generated as a weighted combination of the plurality of MR images, each of the plurality of MR images being weighted by a respective RF coil profile in the plurality of RF coil profiles. The weighting may be computed according to:

$$x = \sum_{i=1}^{N_{coil}} \frac{s_i^* x_i}{\sum_{j=1}^{N_{coil}} s_j^* s_j}$$

where the RF coil profiles $S_j$ are estimated using the neural network at act 2006 of process 2000.

After the combined image is computed at act 2008, the combined image is output at act 2010 (e.g., to a screen, saved to a memory, sent to another computing device, etc.).

Figure 20C:
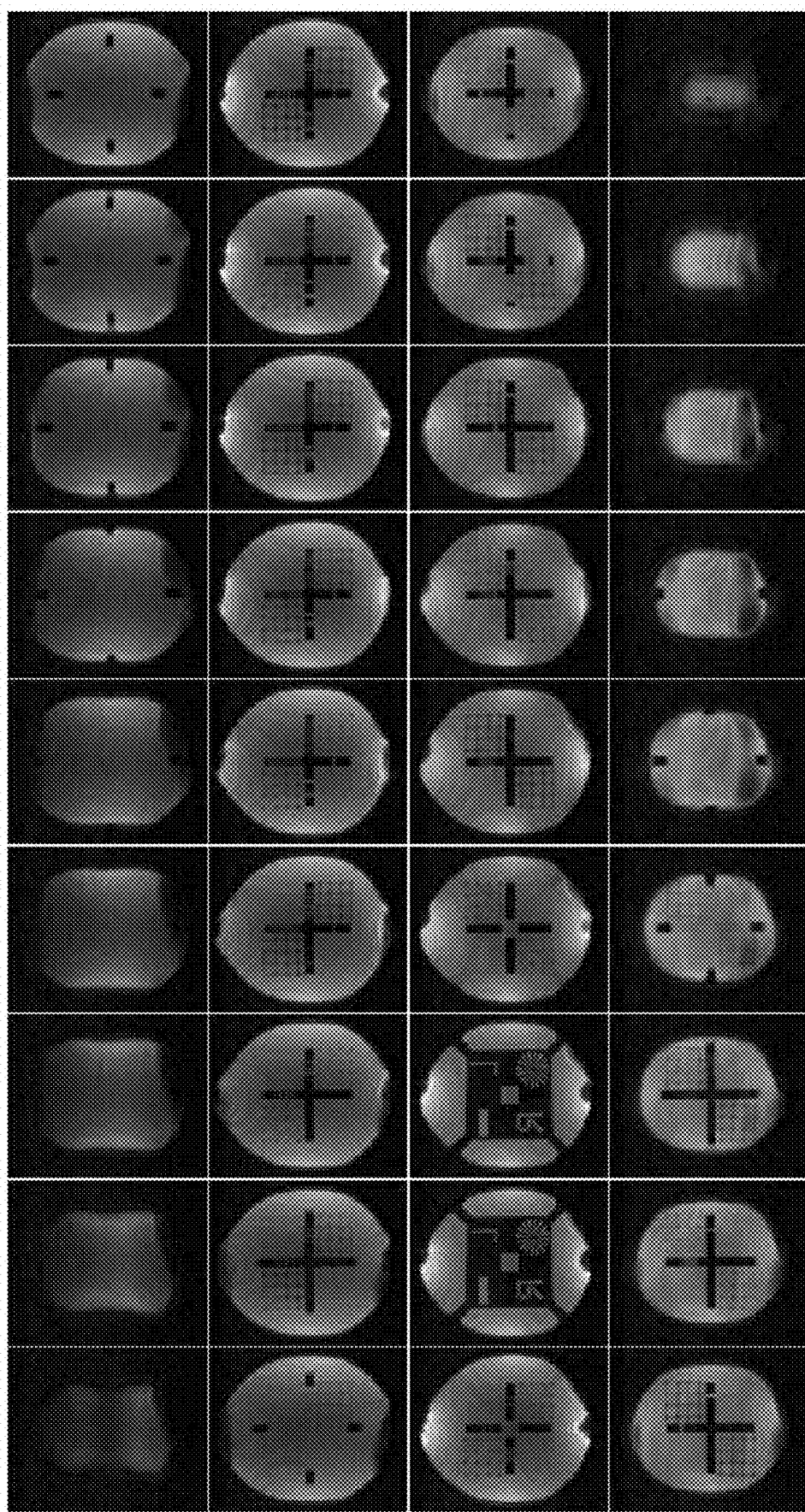
FIGS. 20C, 20D, 20E, 20F, 20G, and 20H illustrate performance of the neural network coil profile estimation techniques described herein relative to conventional parallel imaging techniques.
Figure 20D:
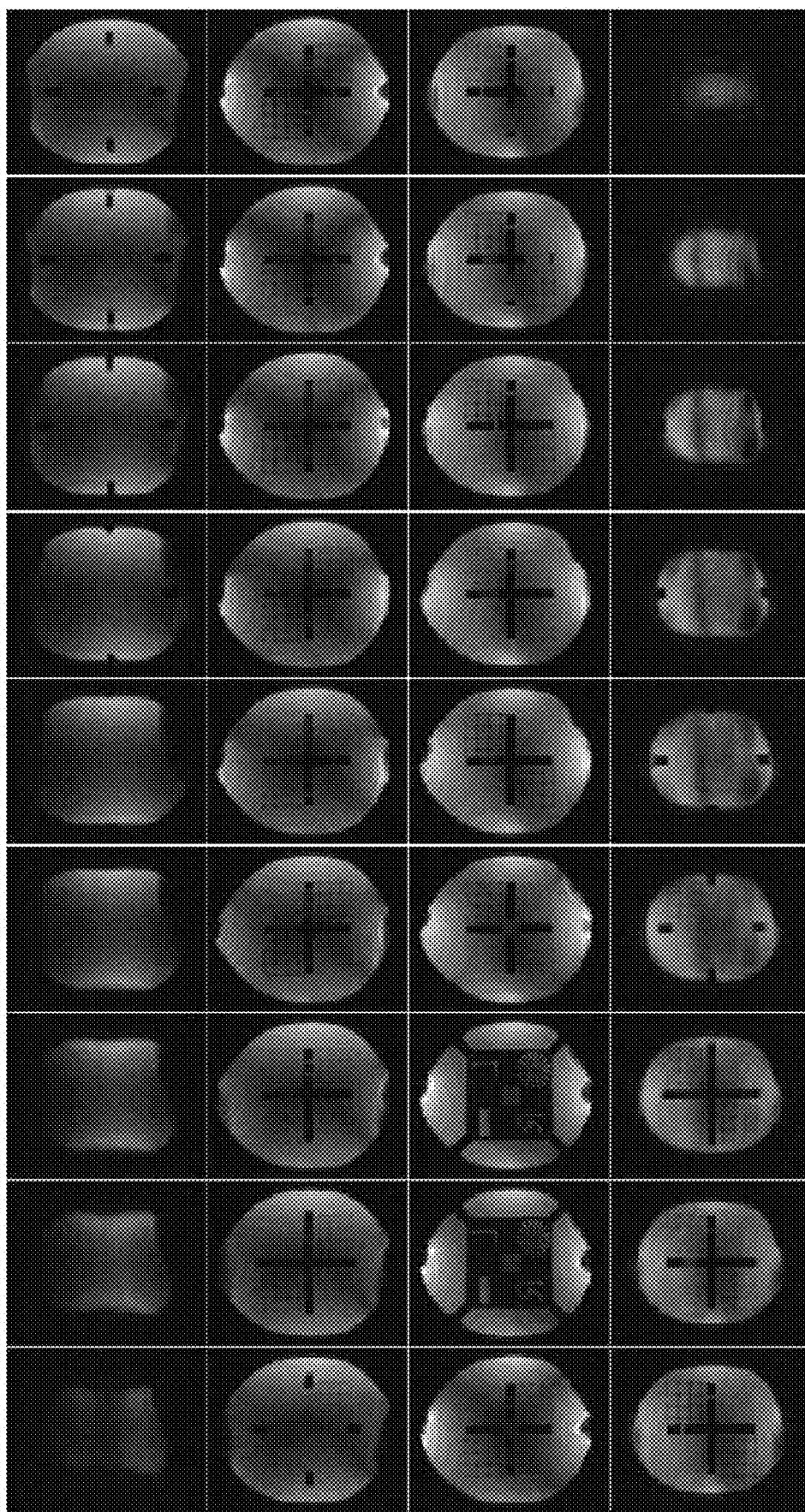
Figure 20E:
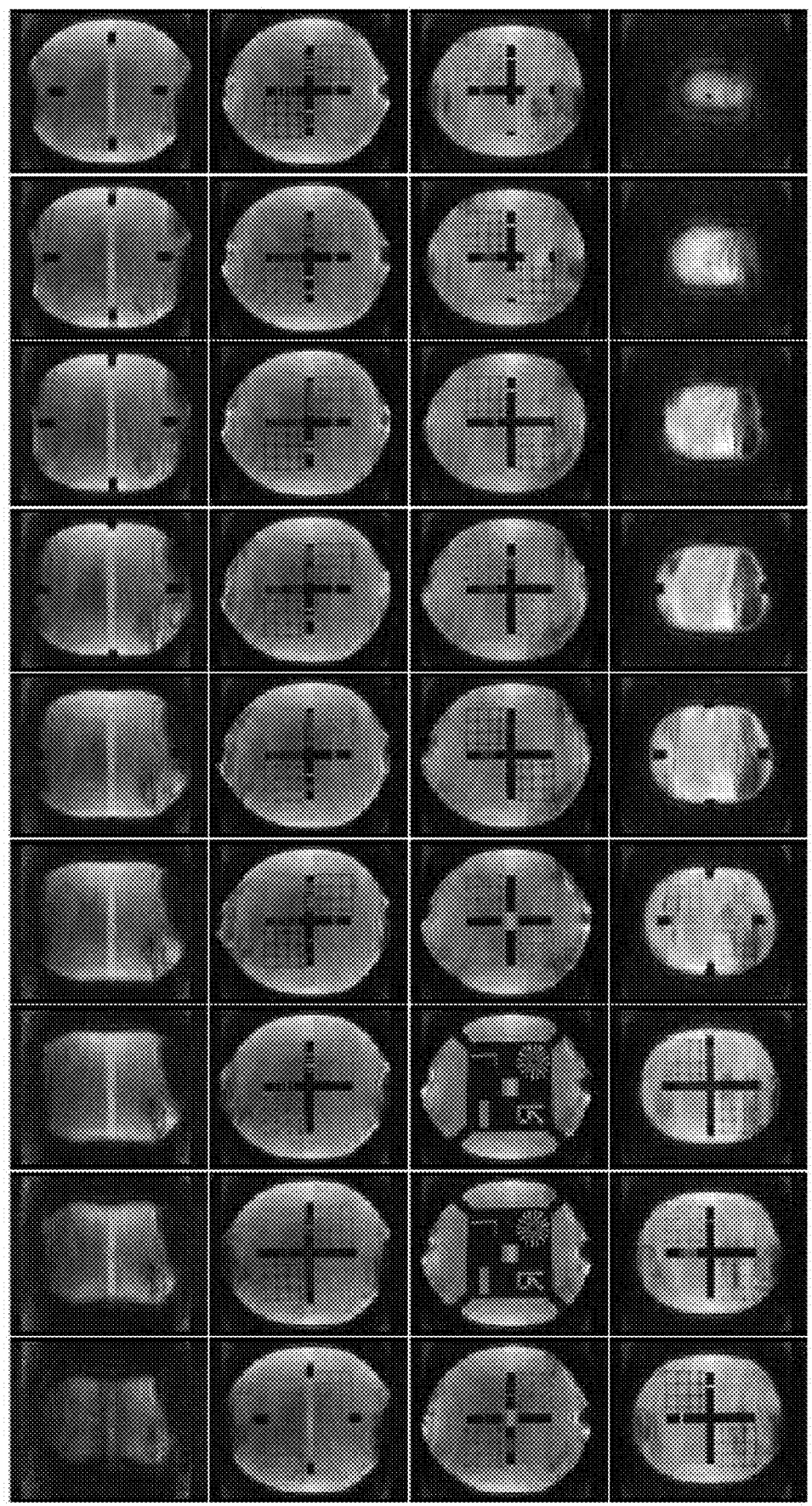
Figure 20F:
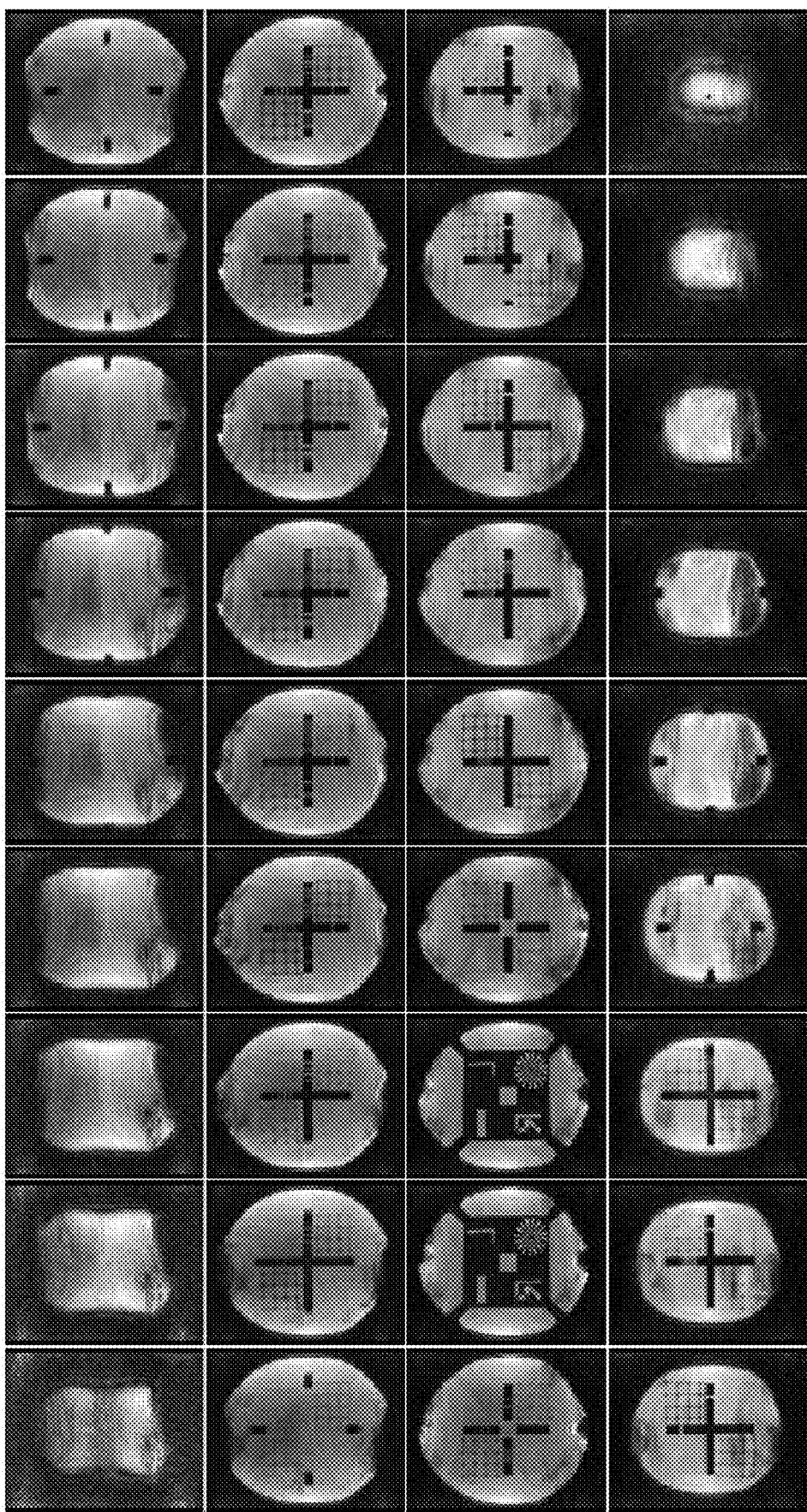

FIGS. 20C-20H illustrate performance of the neural network coil profile estimation techniques described herein. FIGS. 20C and 20D show reconstructions a phantom imaged using multiple RF coils using conventional the residual sum of squares and adaptive approaches (of D. O. Walsh, A. F. Gmitro, and M. W. Marcellin). FIGS. 20E and 20F show results obtained using the neural network techniques described herein. Both FIGS. 20E and 20F show results obtained by estimating individual RF coil profiles using the neural network of FIG. 20B, with the results of FIG. 20F differing only in that the output of the neural network was smoothed prior to the combination of the images. The higher SNR and quality of the resulting images in FIGS. 20E and 20F (as compared to the results shown in FIGS. 20C and 20D) are readily apparent.

Figure 20G:
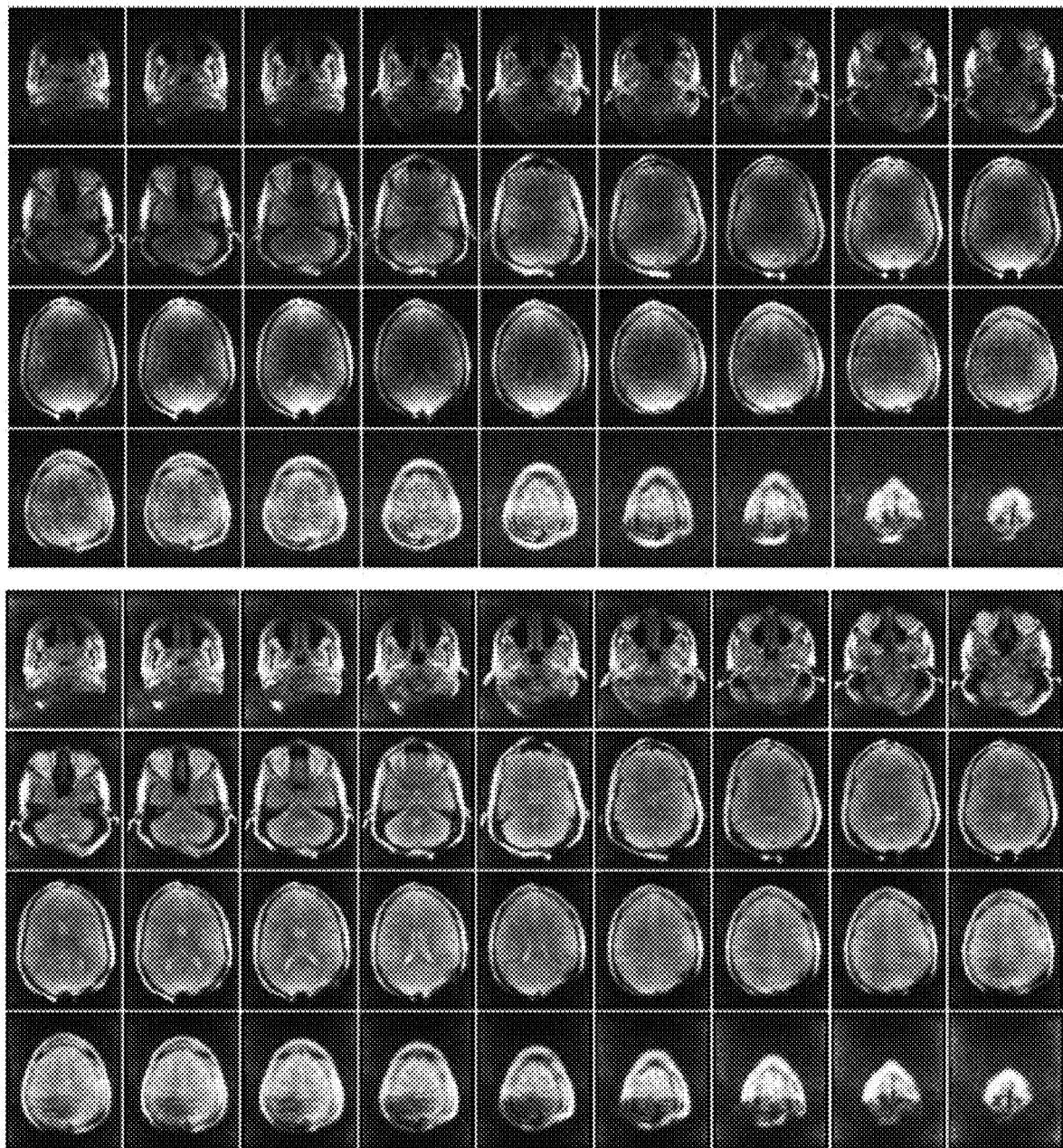

FIG. 20G (top) shows images of a patient's brain obtained using parallel imaging and the conventional residual sum of squares technique, which are of lower quality and have lower SNR than the images shown in the bottom half of FIG. 20G, which were obtained using the neural network techniques described herein.

Figure 20H:
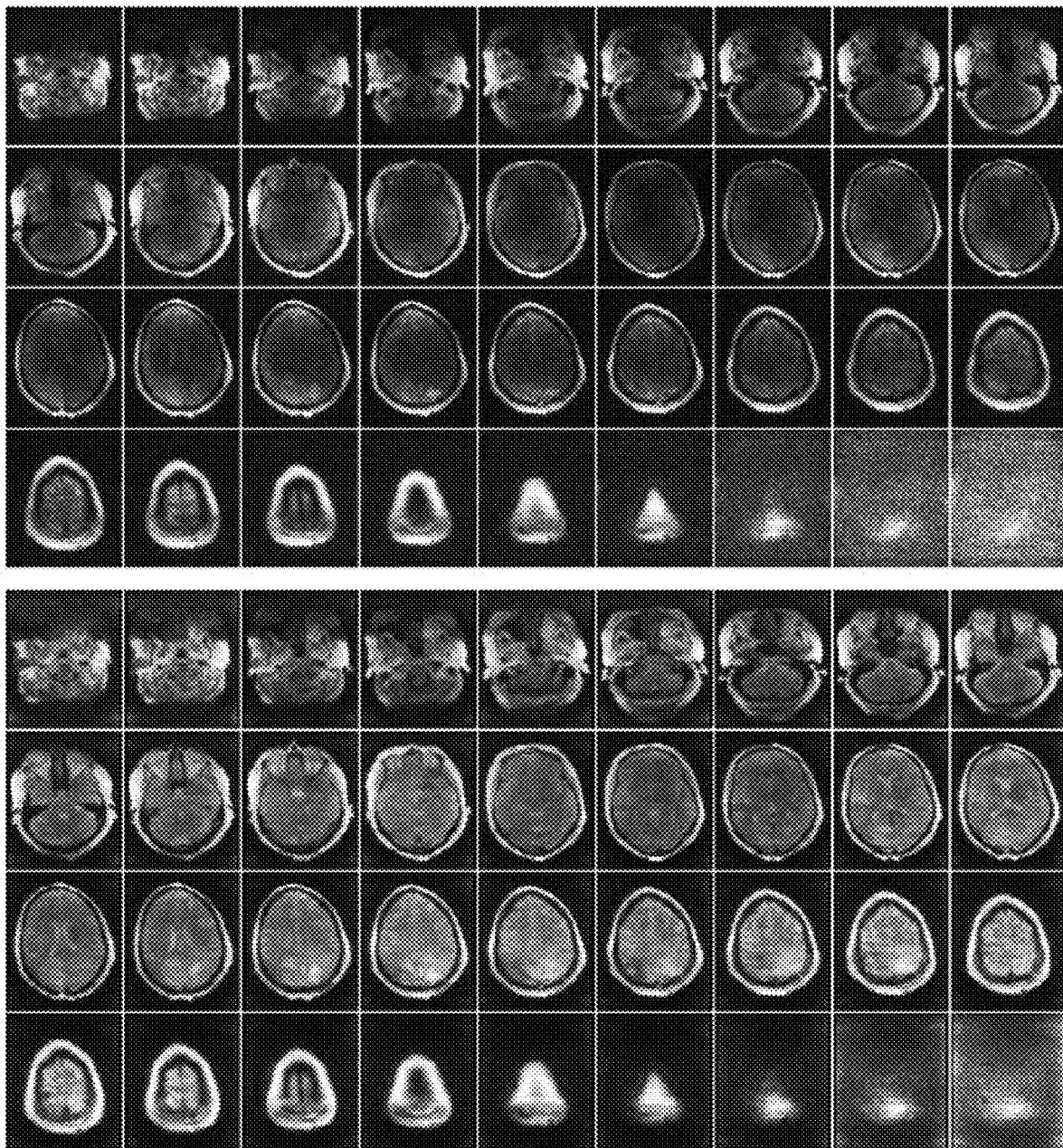

FIG. 20H (top) shows images of another patient's brain obtained using parallel imaging and the conventional residual sum of squares technique, which are of lower quality and have lower SNR than the images shown in the bottom half of FIG. 20H, which were obtained using the neural network techniques described herein.

Coil Compression

In some of the embodiments in which multiple RF coils are used to collect MR data in parallel (parallel imaging), the data may be transformed as though it were observed by a smaller number of virtual RF coils, with the data "observed" by the virtual RF coils being derived from the data actually observed by the physical RF coils part of the MRI system.

For example, in some embodiments, if the MRI system collects data using 16 RF coils, the collected data may be transformed using a linear transformation A as though it were observed by 8 virtual RF coils. As a specific non-limiting example, suppose each of the 16 RF coils were to collect 100 measurements, then measurements may be organized in a 16×100 matrix M of data. In turn, the linear transformation A may be a 8×16 matrix, such that when it is applied to the data (by computing the matrix product AM), the resulting data for the virtual coils is an 8×100 matrix of data in which at each of 100 time points, eight data points corresponding to eight virtual RF coils are to be used for further processing instead of 16 data points corresponding to 16 physical RF coils.

There are numerous benefits to performing such a transformation, which is sometimes termed "geometric coil compression." Generally, one benefit is that geometric coil compression will transform the data so that the signals from the dominant RF coils are emphasized in subsequent processing. Moreover, the inventors have recognized that geometric coil compression has particular benefits when used in conjunction with the neural network techniques described herein. First, using coil compression to reduce the input data to a fixed number of virtual RF coils allows the neural networks described herein to be trained independently of the number of physical RF coils in the MRI system in which the neural networks will be deployed. In this way, neural networks trained for processing data from M virtual RF coils may be deployed in any MRI system that has M or more physical RF coils. This also provides flexibility if one or more RF coils in an MRI system is taken offline.

Second, RF coil compression allows for improved training of neural networks because each of the virtual RF channels contains more information than the physical RF channels would have, which makes it easier for the neural network training algorithms to extract information for estimating neural network rates, resulting in faster training (e.g., fewer iterations thereby reducing computational resources required for training) and improved performance. Reducing the number of channels also reduces the overall number of parameters to be estimated in the neural network models described herein, which also improves training performance.

Accordingly, in some embodiments, the neural network models described herein may be trained to process data that has been coil compressed. In this way, when a neural network (e.g., the reconstruction neural network 212 or any other neural network described herein) is deployed to process MR data collected by multiple RF coils, the collected data is first coil compressed (e.g., by a suitable transformation A) and then provided to the neural network.

In some embodiments, the linear transformation A (sometimes termed the coil compression matrix) may be found as follows. Let three-dimensional (3D) k-space be indexed by each location $k=[k_x, k_y, k_z]^T$, and let a multi-coil k-space value be given by $v(k)=[v_1(k), v_2(k) \ldots, v_{N_{coil}}(k)]$, where $N_{coil}$ represents the number of physical RF coils in an MRI system (e.g., 4, 8, 16, 32, 64, 128, any number of coils between 16 and 64, any number of coils between 32 and 128, or any other suitable number or range within these ranges). Let the coil compression matrix be a complex-valued $M \times N_{coil}$ matrix $A \in \mathbb{C}^{M \times N_{coil}}$ such that $v'=Av$, and $v$ is the corresponding k-space data represented as M virtual coils. In some embodiments, the coil compression matrix A may be determined according to:

$$\min{}_A \|(A^H A - I) v(k)\|^2 \text{ s.t. } AA^H = I.$$

Figure 21:
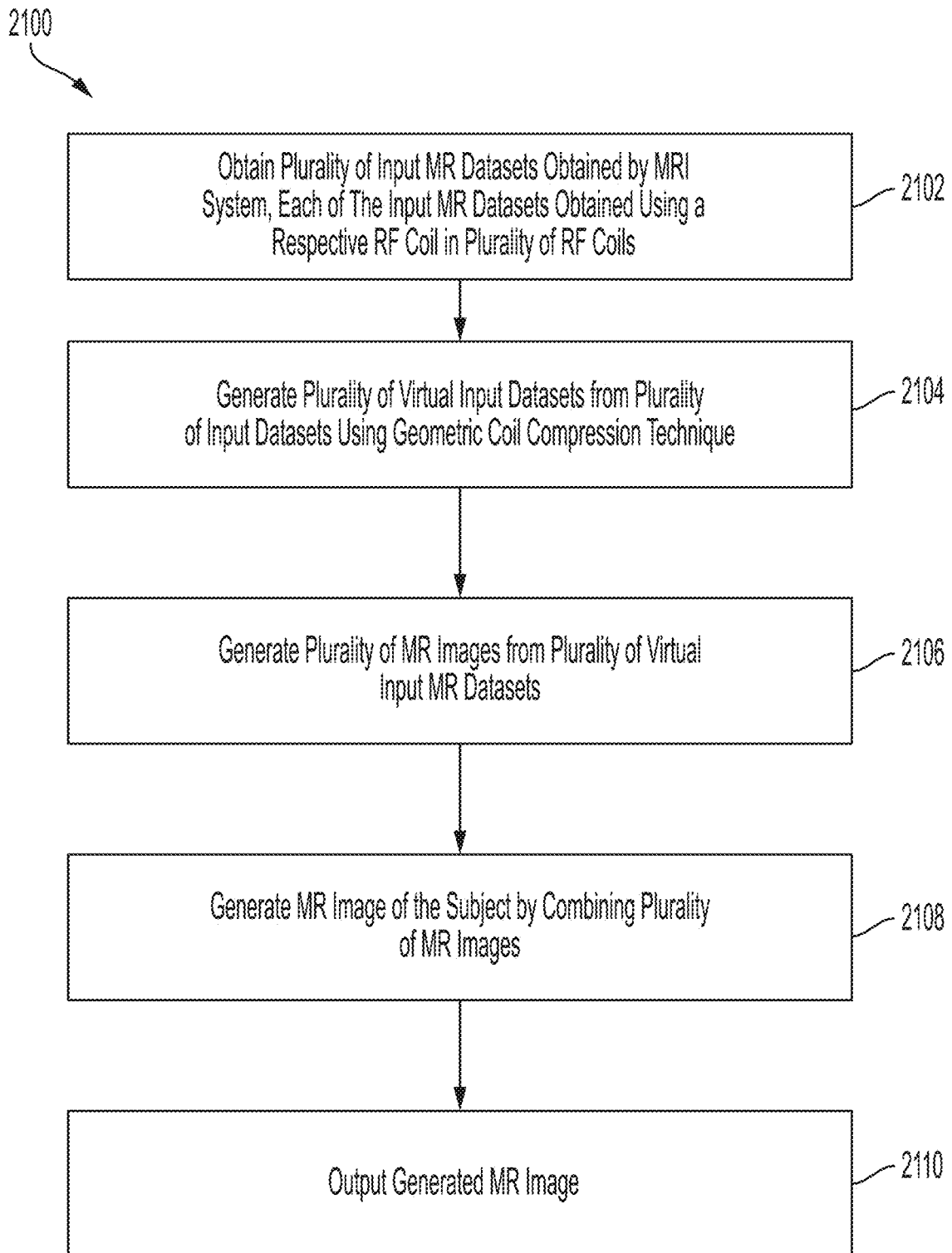
FIG. 21 is a flowchart of an illustrative process 2100 for generating an MR image using geometric coil compression from data obtained by multiple physical RF coils, in accordance with some embodiments of the technology described herein.

In some embodiments, the process of 2000 generating an MR image from input MR spatial frequency data collected by multiple coils may be adapted to utilize the geometric coil compression techniques described herein. An illustrative example is described next with reference to FIG. 21, which is a flowchart of an illustrative process 2100 for generating an MR image using geometric coil compression from data obtained by multiple physical RF coils, in accordance with some embodiments of the technology described herein. Process 2100 may be performed by any suitable computing device(s). For example, process 2100 may be performed by one or more processors (e.g., central processing units and/or graphics processing units) part of the MRI system and/or by one or more processors external to the MRI system (e.g., computers in an adjoining room, computers elsewhere in a medical facility, and/or on the cloud).

Process 2100 begins at act 2102, where a plurality of input MR datasets previously obtained by an MRI system are accessed. The MRI system includes multiple RF coils (say "N" coils, without loss of generality), and each of the plurality of input MR data sets includes data collected by a respective RF coil from among the multiple RF coils.

Next, process 2100 proceeds to act 2104, where geometric coil compression is performed on the data accessed at act 2102. Applying geometric coil compression to the plurality of input MR datasets generates a respective plurality of virtual input data sets. In some embodiments, generating the virtual input data sets involves: (1) determining the coil compression matrix A; and (2) applying the coil compression matrix A to the plurality of input MR data sets to obtained the respective plurality of virtual input MR datasets. In some embodiments, determining the coil compression matrix A may involve determining the coil compression matrix from the data in the plurality of input MR datasets. The determining may be performed using an optimization such as, for example, $(\min{}_A \|(A^H A - I) v(k)\|^2 \text{ s.t. } AA^H = I$.

In some embodiments, the geometric coil compression may reduce the number of channels by a factor of 2 (e.g., from 16 physical RF coils to 8 virtual RF coils or fewer, from 32 physical RF coils to 16 virtual RF coils or fewer, etc.), by a factor of 4 (e.g., from 32 physical RF coils to 8 virtual RF coils or fewer), or by any other suitable factor, as aspects of the technology described herein are not limited in this respect.

Next, process 2100 proceeds to act 2106, where a plurality of MR images is generated from the plurality of virtual input MR data. This may be performed using any suitable reconstruction technique. For example, the reconstruction may be performed using any neural network reconstruction technique described herein (e.g., using neural network 212). As another example, the reconstruction may be performed using compressed sensing and/or any other suitable type of non-linear reconstruction technique. As yet another example, the reconstruction may be performed using a uniform or a non-uniform Fourier transformation.

Next, at act 2108, the plurality of MR images are combined to generate an image of the subject. This may be done in any suitable way including in any of the ways described with respect to act 2008 of process 2000. The generated image is then output at act 2110.

Pre-Whitening

The inventors have appreciated that, when MR data are being collected in parallel by multiple RF coils ("parallel imaging"), different RF coils may detect different amounts and/or types of noise. As a result, the received noise may be unevenly distributed among the multiple receive channels. For example, even if the noise were uncorrelated and uniformly distributed among k-space locations, there may nonetheless be noise level differences between the individual RF coils, and the noise detected by one RF coil may be correlated with the noise detected by another RF coil. Left uncorrected, such level differences and correlations may lead to a reduction of image quality and SNR.

Accordingly, in some embodiments, the relationship of noise signals received by multiple receive coils may be represented by an N×N matrix, where N is the number of coils, expressed as $\Psi_{ij} = \langle \eta_i, \eta_j^H \rangle$, where $\eta_i$ is the noise component of the $i^{th}$ signal. This matrix will not be he identity matrix due to correlation among the noise signals received using different RF coils and/or relatively different amounts of noise observed by the different RF coils. In some embodiments, specific values of such a matrix may be obtained during a calibration stage when the RF coils measure noise levels without a subject being imaged so that no MR signal is present. Any suitable correlation estimation technique may be used in this regard, as aspects of the technology described herein are not limited in this respect.

Accordingly, given the matrix $\Psi_{ij}$, in some embodiments, a pre-whitening matrix W may be estimated from the matrix $\Psi_{ij}$ and subsequently applied to the input data prior to the data being processed by the neural network algorithms described herein. In particular, some embodiments involve determining the pre-whitening matrix W such that $v_{pw} = Wv$, where $v$ is the original k-space measurement, $v_{pw}$ is the prewhitened k-space measurement, and so that W satisfies $W^T W = \Psi^{-1}$. Applying W to the input data allows for the received signals to be decorrelated, which in turn improves the quality and SNR of the images obtained from these data.

The pre-whitening matrix W may be estimated in any suitable way. For example, in some embodiments, W may be determined using zero-phase component analysis (ZCA) according to: $W=\Psi^{-1/2}$. As another example, in some embodiments, W may be determined using principal components analysis (PCA) according to: $W=\Gamma^{-1}U^T$, where $\Psi=U\Gamma^{-1/2}U^T$ is the singular value decomposition (SVD) of $\Psi$. As yet another example, in some embodiments, W may be determined used the Cholesky decomposition according to: $W=L^{-1}$, where $LL^H=\Psi$ is the Cholesky decomposition.

k-Space Weighting

The inventors have appreciated that the neural network techniques described herein may be improved if the input MR spatial frequency data were weighted in the spatial frequency domain (k-space). In particular, the inventors have appreciated that weighting input MR spatial frequency data in k-space prior to reconstruction may improve the quality of the reconstruction. Accordingly, in some embodiments, the input MR spatial frequency data may be weighted in k-space prior to or as part of reconstruction.

In some embodiments, the input MR spatial frequency data may be weighted by using a weighting function known in advance. For example, individual input MR spatial frequency data points may be weighted based on their distances to the k-space origin (e.g., points closer to the origin of k-space are given greater weight or points closer to the origin of k-space are given less weight). As another example, input MR spatial frequency data may be weighted using a weighting function based on the wavelet transform given by:

$$\psi_s(w) = \frac{1}{\sqrt{2^s}} \frac{i2^s w}{2} \left( \frac{\sin(2^s w)/4}{2^s w/4} \right)^2 \exp\left( -i\frac{2^s w}{2} \right)$$

where w is a frequency, which can be |k| for n-dimensional k-space data, and s is a scale, which may be determined based on the image resolution, k-space grid size, and/or the degree to which the data is undersampled in k-space.

Additionally or alternatively, the k-space weighting may be learned. In some embodiments, for example, the neural network (e.g., reconstruction neural network 212) may include a layer for weighting the input data non-uniformly in the spatial frequency domain. The weights of this neural network layer may be learned during training, and the loss function used for training the neural network may include one or more terms to guide the type of weighting that is to be learned (e.g., to weight more near the k-space origin, away from the k-space origin, near a particular region of k-space, or in any other suitable way). In this way, the weighting may not only be learned (resulting in improved performance relative to known weightings that are fixed in advance), but also may be learned jointly with other parameters of the neural networks described herein, further improving overall reconstruction performance.

Example MRI Systems

Some embodiments of the technology described herein may be implemented using portable low-field MRI systems, aspects of which are described below with reference to FIGS. 22, 23, 24A-B, and 25A-B. Some aspects of such portable low-field MRI systems are further described in U.S. Pat. No. 10,222,434, filed on Jan. 24, 2018, titled "Portable Magnetic Resonance Imaging Methods and Apparatus," which is incorporated by reference in its entirety herein.

Figure 22:
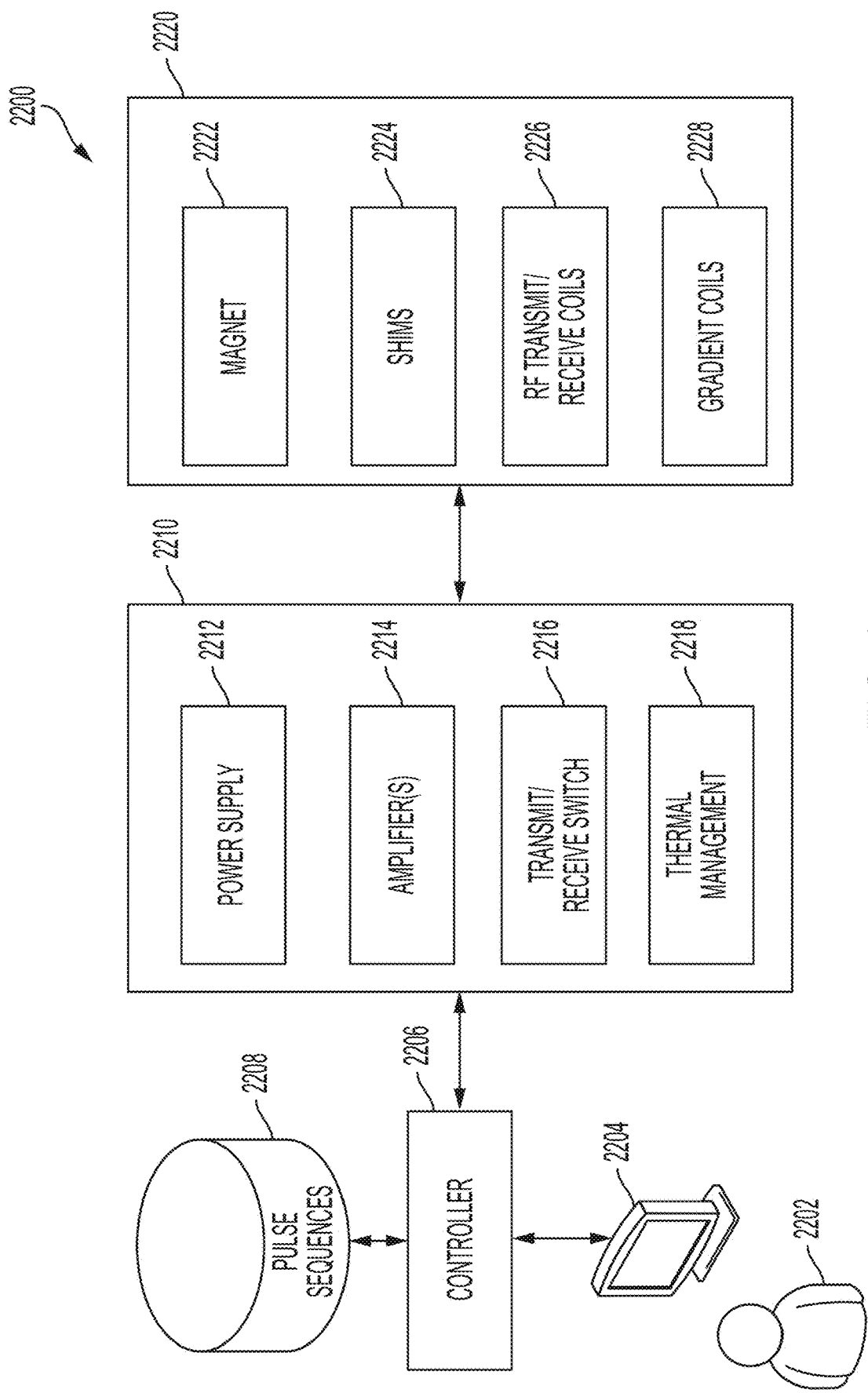
FIG. 22 is a schematic illustration of a low-field MRI system, in accordance with some embodiments of the technology described herein.

FIG. 22 is a block diagram of example components of a MRI system 2200. In the illustrative example of FIG. 22, MRI system 2200 comprises workstation 2204, controller 2206, pulse sequences store 2208, power management system 2210, and magnetic components 2220. It should be appreciated that system 2200 is illustrative and that an MRI system may have one or more other components of any suitable type in addition to or instead of the components illustrated in FIG. 22.

As illustrated in FIG. 22, magnetic components 2220 comprise $B_0$ magnet 2222, shims 2224, RF transmit and receive coils 2226, and gradient coils 2228. $B_0$ magnet 2222 may be used to generate, at least in part, the main magnetic field $B_0$. $B_0$ magnet 2222 may be any suitable type of magnet that can generate a main magnetic field, and may include one or more $B_0$ coils, correction coils, pole pieces, etc. In some embodiments, $B_0$ magnet 2222 may be a permanent magnet. For example, in some embodiments, $B_0$ magnet 222 may comprise multiple permanent magnet pieces organized in a bi-planar arrangement of concentric permanent magnet rings as described herein including with reference to FIG. 23. In some embodiments, $B_0$ magnet 2222 may be an electromagnet. In some embodiments, In some embodiments, $B_0$ magnet 2222 may be a hybrid magnet comprising one or more permanent magnets and one or more electromagnets.

In some embodiments, shims 2224 may be used to contribute magnetic field(s) to improve the homogeneity of the $B_0$ field generated by magnet 2222. In some embodiments, shims 2224 may be permanent magnet shims. In some embodiments, shims 2224 may be electromagnetic and may comprise one or more shim coils configured to generate a shimming magnetic field. In some embodiments, gradient coils 2228 may be arranged to provide gradient fields and, for example, may be arranged to generate gradients in the magnetic field in three substantially orthogonal directions (X, Y, Z) to localize where MR signals are induced. In some embodiments, one or more magnetics components 2220 (e.g., shims 2224 and/or gradient coils 2228) may be fabricated using the laminate techniques.

In some embodiments, RF transmit and receive coils 2226 may comprise one or multiple transmit coils that may be used to generate RF pulses to induce a magnetic field Bi. The transmit/receive coil(s) may be configured to generate any suitable type of RF pulses configured to excite an MR response in a subject and detect the resulting MR signals emitted. RF transmit and receive coils 2226 may include one or multiple transmit coils and one or multiple receive coils. The configuration of the transmit/receive coils varies with implementation and may include a single coil for both transmitting and receiving, separate coils for transmitting and receiving, multiple coils for transmitting and/or receiving, or any combination to achieve single channel or parallel MRI systems.

In some embodiments, RF transmit and receive coils 2226 include multiple RF coils, which allow the MRI system 2200 to concurrently receive MR signals on multiple channels. In some embodiments, the MR signals received by multiple RF coils may be processed and combined using the techniques described herein including with reference to FIGS. 20 and 21.

Power management system 2210 includes electronics to provide operating power to one or more components of the low-field MRI system 2200. For example, power management system 2210 may include one or more power supplies, gradient power amplifiers, transmit coil amplifiers, and/or any other suitable power electronics needed to provide suitable operating power to energize and operate components of the low-field MRI system 2200.

As illustrated in FIG. 22, power management system 2210 comprises power supply 2212, amplifier(s) 2214, transmit/receive switch 2216, and thermal management components 2218. Power supply 2212 includes electronics to provide operating power to magnetic components 2220 of the low-field MRI system 2200. For example, in some embodiments, power supply 2212 may include electronics to provide operating power to one or more $B_0$ coils (e.g., $B_0$ magnet 2222 when it is an electromagnet) to produce the main magnetic field for the low-field MRI system, one or more shims 2224, and/or one or more gradient coils 1628. In some embodiments, power supply 2212 may be a unipolar, continuous wave (CW) power supply. Transmit/receive switch 2216 may be used to select whether RF transmit coils or RF receive coils are being operated.

In some embodiments, amplifier(s) 2214 may include one or more RF receive (Rx) pre-amplifiers that amplify MR signals detected by RF receive coil(s) (e.g., coils 2224), RF transmit (Tx) amplifier(s) configured to provide power to RF transmit coil(s) (e.g., coils 2226), gradient power amplifier(s) configured to provide power to gradient coil(s) (e.g., gradient coils 2228), and/or shim amplifier(s) configured to provide power to shim coil(s) (e.g., shims 2224 in embodiments where shims 2224 include one or more shim coils).

In some embodiments, thermal management components 2218 provide cooling for components of low-field MRI system 2200 and may be configured to do so by facilitating the transfer of thermal energy generated by one or more components of the low-field MRI system 2200 away from those components. Thermal management components 2218 may include components to perform water-based or air-based cooling, which may be integrated with or arranged in close proximity to MRI components that generate heat including, but not limited to, $B_0$ coils, gradient coils, shim coils, and/or transmit/receive coils.

As illustrated in FIG. 22, low-field MRI system 2200 includes controller 2206 (also referred to as a console) having control electronics to send instructions to and receive information from power management system 2210. Controller 2206 may be configured to implement one or more pulse sequences, which are used to determine the instructions sent to power management system 2210 to operate the magnetic components 2220 according to a desired sequence. For example, controller 2206 may be configured to control the power management system 2210 to operate the magnetic components 2220 in accordance with a balanced steady-state free precession (bSSFP) pulse sequence, a low-field gradient echo pulse sequence, a low-field spin echo pulse sequence, a low-field inversion recovery pulse sequence, arterial spin labeling, diffusion weighted imaging (DWI), and/or any other suitable pulse sequence.

In some embodiments, controller 2206 may be configured to implement a pulse sequence by obtaining information about the pulse sequence from pulse sequences repository 2208, which stores information for each of one or more pulse sequences. Information stored by pulse sequences repository 2208 for a particular pulse sequence may be any suitable information that allows controller 2206 to implement the particular pulse sequence. For example, information stored in pulse sequences repository 2208 for a pulse sequence may include one or more parameters for operating magnetics components 2220 in accordance with the pulse sequence (e.g., parameters for operating the RF transmit and receive coils 2226, parameters for operating gradient coils 2228, etc.), one or more parameters for operating power management system 2210 in accordance with the pulse sequence, one or more programs comprising instructions that, when executed by controller 2206, cause controller 2206 to control system 2200 to operate in accordance with the pulse sequence, and/or any other suitable information. Information stored in pulse sequences repository 2208 may be stored on one or more non-transitory storage media.

As illustrated in FIG. 22, in some embodiments, controller 2206 may interact with computing device 2204 programmed to process received MR data (which, in some embodiments, may be spatial frequency domain MR data). For example, computing device 2204 may process received MR data to generate one or more MR images using any suitable image reconstruction process(es) including using any of the techniques described herein that make use of neural network models to generate MR images from spatial frequency MR data. For example, computing device 2204 may perform any of the processes described herein with reference to FIGS. 2D, 2D, 8A-8B, 16, 20, and 21. Controller 2206 may provide information about one or more pulse sequences to computing device 2204 for the processing of data by the computing device. For example, controller 2206 may provide information about one or more pulse sequences to computing device 2204 and the computing device may perform an image reconstruction process based, at least in part, on the provided information.

In some embodiments, computing device 2204 may be any electronic device(s) configured to process acquired MR data and generate image(s) of the subject being imaged. However, the inventors have appreciated that it would be advantageous for a portable MRI system to have sufficient onboard computing capability to perform neural network computations to generate MR images from input spatial frequency data because in many settings (e.g., hospitals), there is limited network bandwidth available for offloading spatial frequency MR data from the MRI machine for processing elsewhere (e.g., in the cloud). Accordingly, in some environments where the MRI system 2200 may be deployed, the inventors have recognized that it is advantageous for the MRI system to include hardware specialized for neural network calculations to perform some of the processes described herein.

Accordingly, in some embodiments, computing device 2204 may include one or multiple graphics processing units (GPU) configured to perform neural network calculations that are to be performed when the neural network models described herein (e.g., neural network model 204, pre-reconstruction neural network 210, reconstruction neural network 212, post reconstruction neural network 214, any of their constituent neural networks, and/or any other neural networks). In some such embodiments, computing device 2204 may be onboard (e.g., within the housing of the low-field MRI system 2200). Accordingly, in some embodiments, MRI system 2200 may include one or more GPU(s) and the GPU(s) may be onboard, for example by being housed within the same housing as one or more components of the power components 2210. Additionally or alternatively, computing device 2204 may include one or more hardware processors, FPGAs, and/or ASICs configured to process acquire MR data and generate image(s) of the subject being imaged.

In some embodiments, a user 2202 may interact with computing device 2204 to control aspects of the low-field MR system 2200 (e.g., program the system 2200 to operate in accordance with a particular pulse sequence, adjust one or more parameters of the system 2200, etc.) and/or view images obtained by the low-field MR system 2200.

Figure 23:
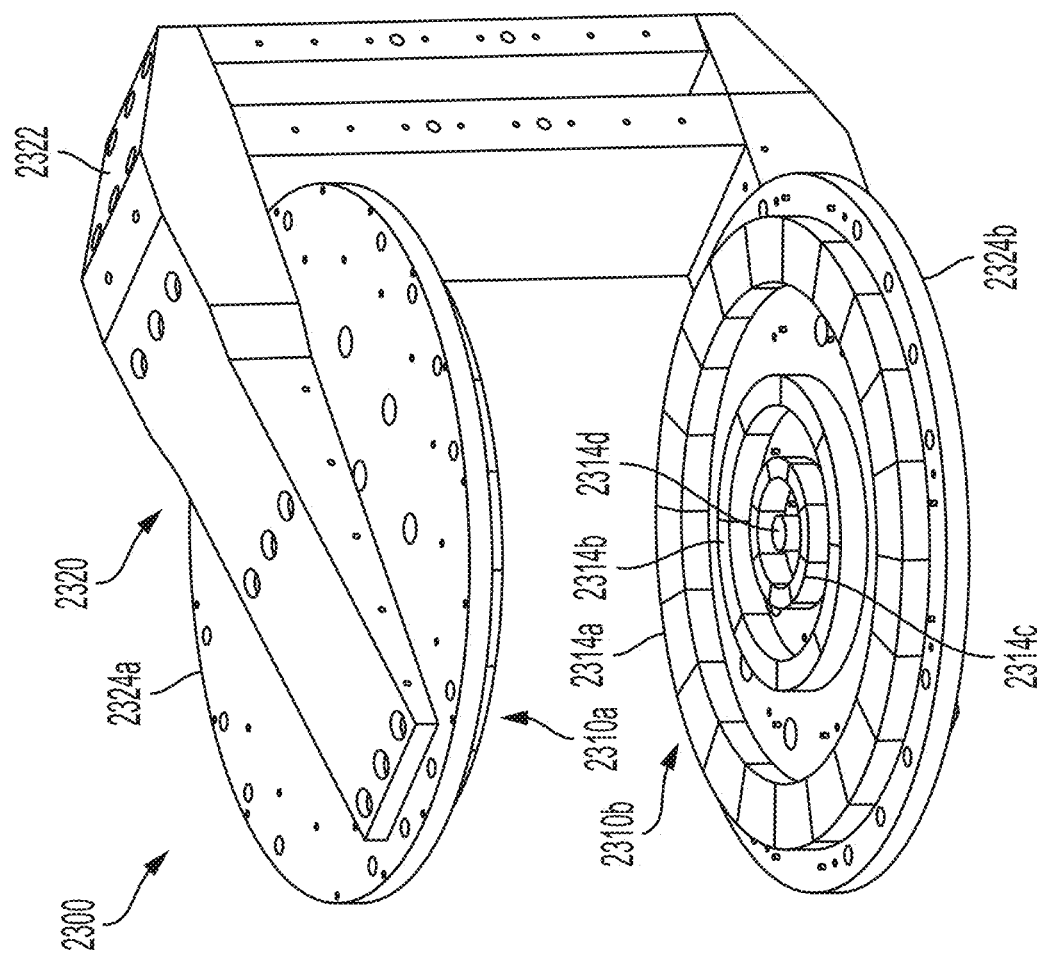
FIG. 23 illustrates a bi-planar permanent magnet configuration for a $B_0$ magnet that may be part of the low-field system of FIG. 22, in accordance with some embodiments of the technology described herein.

FIG. 23 illustrates bi-planar permanent magnet configurations for a $B_0$ magnet, in accordance with some embodiments of the technology described herein. FIG. 23 illustrates a permanent $B_0$ magnet 2300 formed by permanent magnets 2310a and 2310b arranged in a bi-planar geometry and a yoke 2320 that captures electromagnetic flux produced by the permanent magnets and transfers the flux to the opposing permanent magnet to increase the flux density between permanent magnets 2310a and 2310b. Each of permanent magnets 2310a and 2310b is formed from a plurality of concentric permanent magnet rings. As shown in FIG. 23, permanent magnet 2310b comprises an outer ring of permanent magnets 2314a, a middle ring of permanent magnets 2314b, an inner ring of permanent magnets 2314c, and a permanent magnet disk 2314d at the center. Though shown with four concentric permanent magnet rings, permanent magnet 2310b (and permanent magnet 2310a) may have any suitable number of permanent magnet rings. Permanent magnet 2310a may be formed substantially identically to permanent magnet 2310b and, for example, comprise the same set of permanent magnet rings as permanent magnet 2310b.

As shown in FIG. 23A, yoke 2320 comprises a frame 2322 and plates 2324a and 2324b. Plates 2324a and 2324b may capture magnetic flux generated by permanent magnets 2310a and 2310b and direct it to frame 2122 to be circulated via the magnetic return path of the yoke to increase the flux density in the field of view of the $B_0$ magnet. Yoke 2320 may be constructed of any desired ferromagnetic material, for example, low carbon steel, CoFe and/or silicon steel, etc. to provide the desired magnetic properties for the yoke.

Figure 24B:
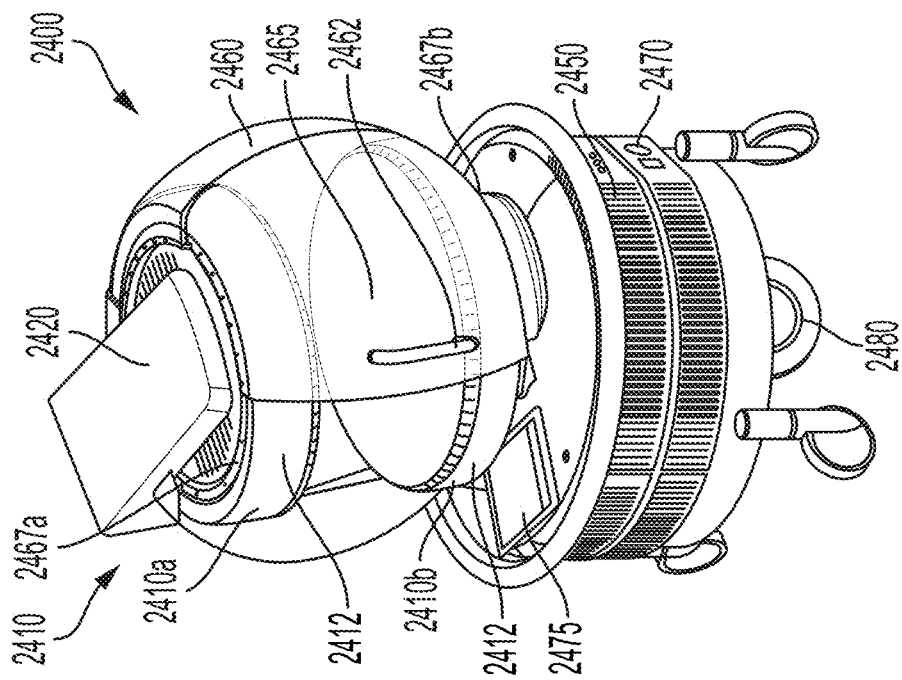
FIGS. 24A and 24B illustrate views of a portable MRI system, in accordance with some embodiments of the technology described herein.
Figure 24A:
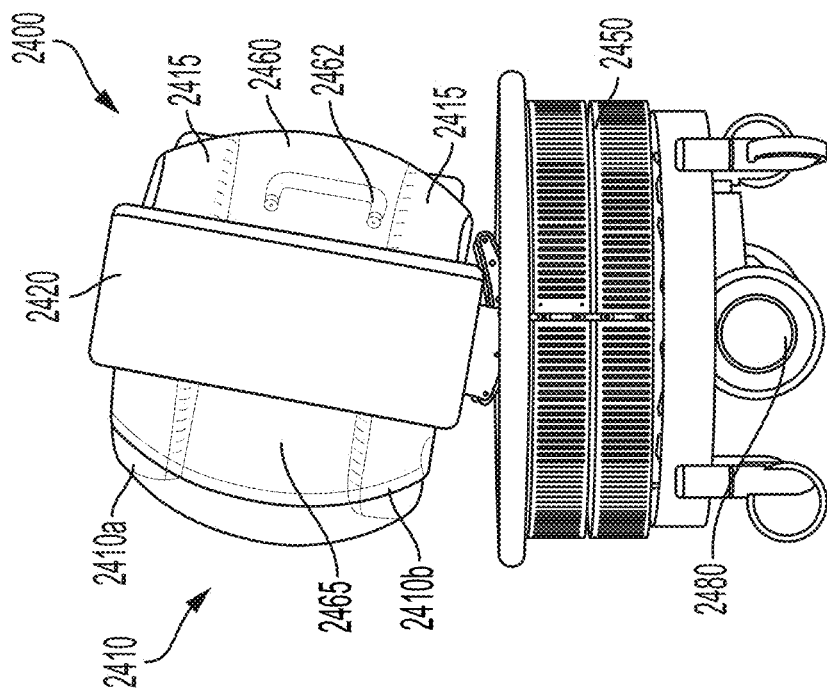

FIGS. 24A and 24B illustrate views of a portable MRI system 2400, in accordance with some embodiments of the technology described herein. Portable MRI system 2400 comprises a $B_0$ magnet 2410 formed in part by an upper magnet 2410a and a lower magnet 2410b having a yoke 2420 coupled thereto to increase the flux density within the imaging region. The $B_0$ magnet 2410 may be housed in magnet housing 2412 along with gradient coils 2415. The $B_0$ magnet 2410 may be the permanent magnet 2310a and 2310b described with reference to FIG. 23 and/or any other suitable type of magnet.

Illustrative portable MRI system 2400 further comprises a base 2450 housing the electronics that operates the MRI system. For example, base 2450 may house electronics including, but not limited to, one or more gradient power amplifiers, an on-system computer (e.g., including one or more GPUs to perform neural network calculations in accordance with some embodiments of the technology described herein), a power distribution unit, one or more power supplies, and/or any other power components configured to operate the MRI system using mains electricity (e.g., via a connection to a standard wall outlet and/or a large appliance outlet). For example, base 2470 may house low power components, such as those described herein, enabling at least in part the portable MRI system to be powered from readily available wall outlets. Accordingly, portable MRI system 2400 can be brought to the patient and plugged into a wall outlet in his or her vicinity.

Portable MRI system 2400 further comprises moveable slides 2460 that can be opened and closed and positioned in a variety of configurations. Slides 2460 include electromagnetic shielding 2465, which can be made from any suitable conductive or magnetic material, to form a moveable shield to attenuate electromagnetic noise in the operating environment of the portable MRI system to shield the imaging region from at least some electromagnetic noise.

In portable MRI system 2400 illustrated in FIGS. 24A and 24B, the moveable shields are configurable to provide shielding in different arrangements, which can be adjusted as needed to accommodate a patient, provide access to a patient, and/or in accordance with a given imaging protocol. For example, for an imaging procedure such as a brain scan, once the patient has been positioned, slides 2460 can be closed, for example, using handle 2462 to provide electromagnetic shielding 2465 around the imaging region except for the opening that accommodates the patient's upper torso. As another example, for an imaging procedure such as a knee scan, slides 2460 may be arranged to have openings on both sides to accommodate the patient's leg or legs. Accordingly, moveable shields allow the shielding to be configured in arrangements suitable for the imaging procedure and to facilitate positioning the patient appropriately within the imaging region. Electrical gaskets may be arranged to provide continuous shielding along the periphery of the moveable shield. For example, as shown in FIG. 24B, electrical gaskets 2467a and 2467b may be provided at the interface between slides 2460 and magnet housing to maintain to provide continuous shielding along this interface. In some embodiments, the electrical gaskets are beryllium fingers or beryllium-copper fingers, or the like (e.g., aluminum gaskets), that maintain electrical connection between shields 2465 and ground during and after slides 2460 are moved to desired positions about the imaging region.

To facilitate transportation, a motorized component 2480 is provide to allow portable MRI system to be driven from location to location, for example, using a control such as a joystick or other control mechanism provided on or remote from the MRI system. In this manner, portable MRI system 2400 can be transported to the patient and maneuvered to the bedside to perform imaging.

Figure 25A:
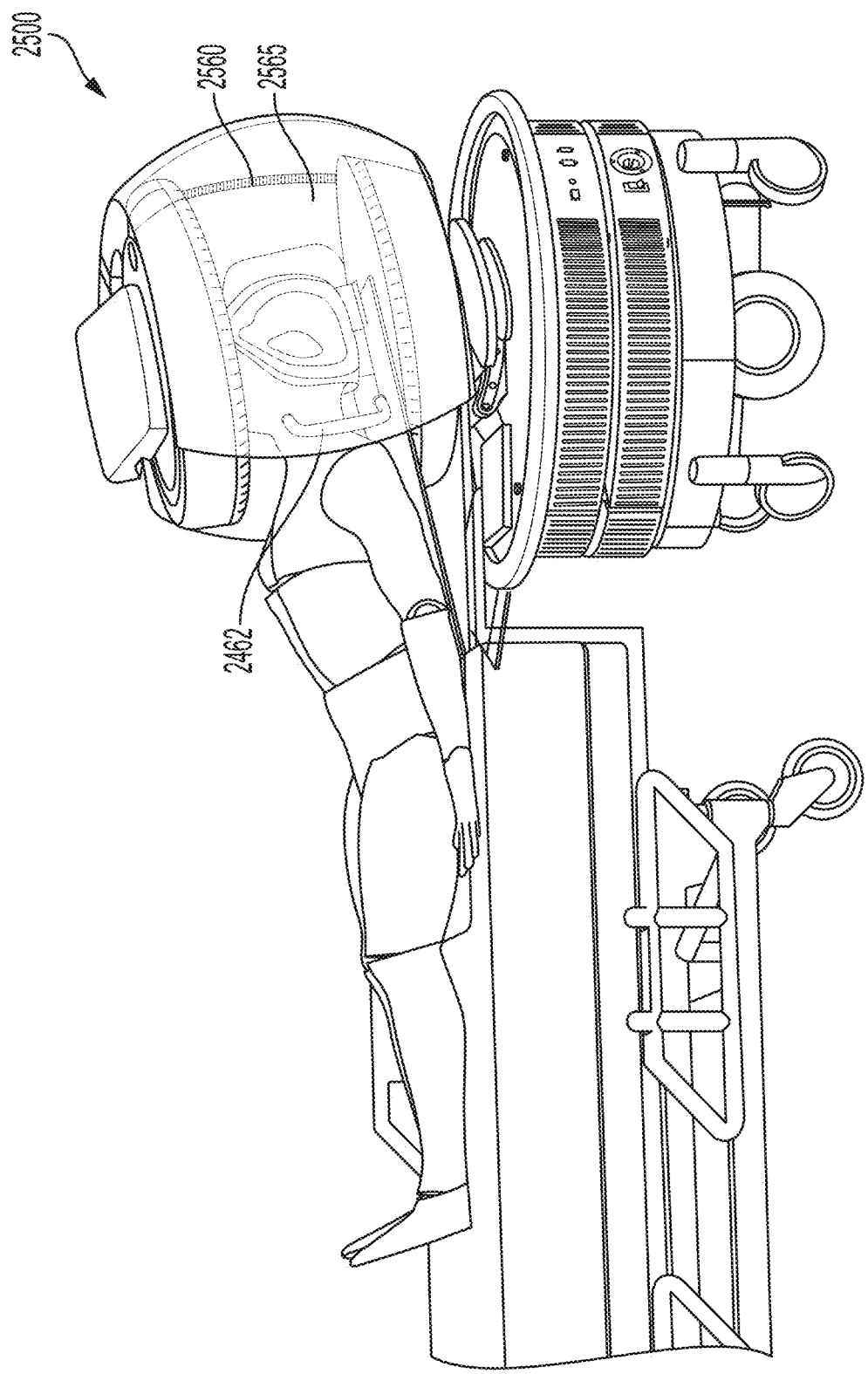
FIG. 25A illustrates a portable MRI system performing a scan of the head, in accordance with some embodiments of the technology described herein.
Figure 25B:
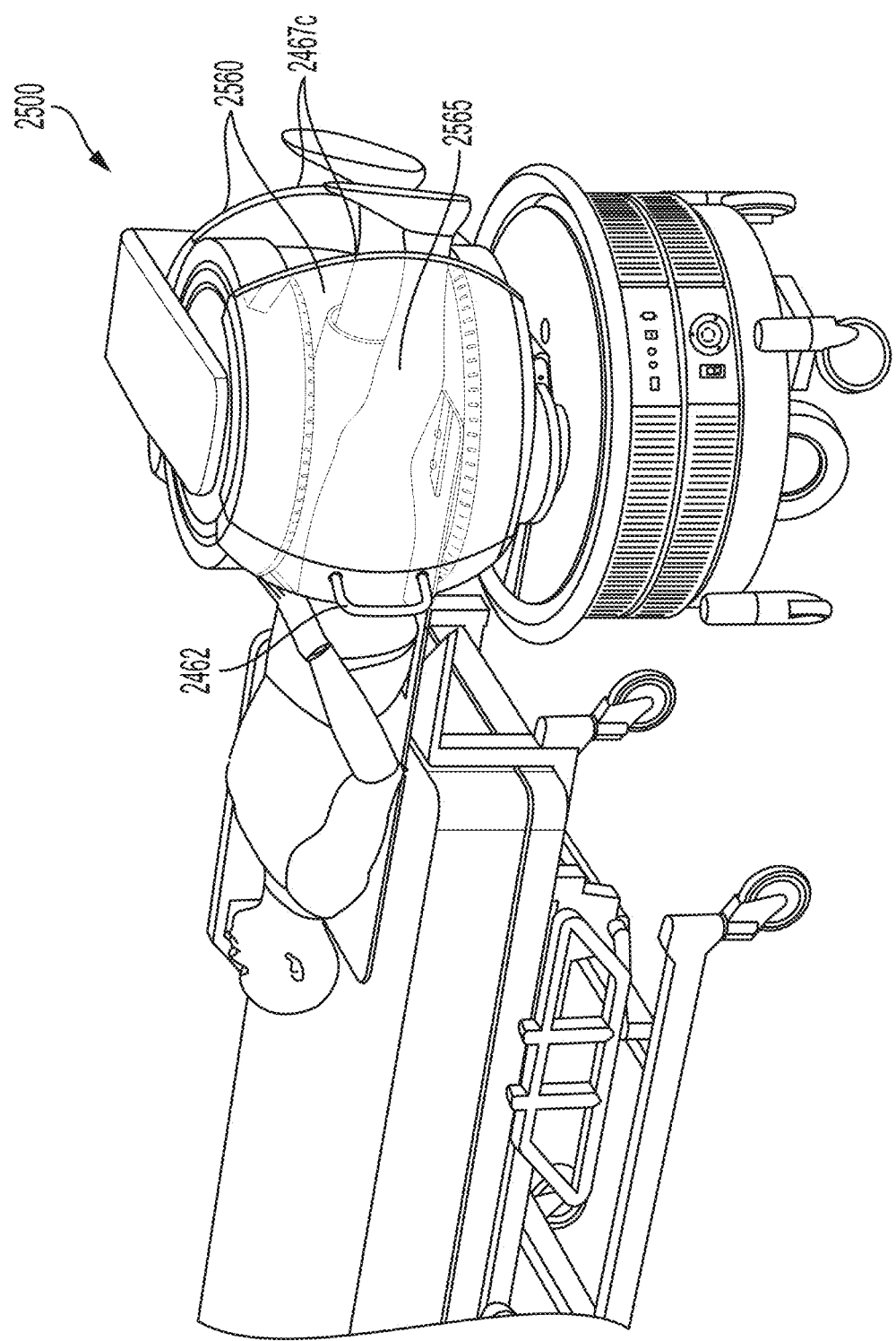
FIG. 25B illustrates a portable MRI system performing a scan of the knee, in accordance with some embodiments of the technology described herein.

FIG. 25A illustrates a portable MRI system 2500 that has been transported to a patient's bedside to perform a brain scan. FIG. 25B illustrates portable MRI system 2500 that has been transported to a patient's bedside to perform a scan of the patient's knee. As shown in FIG. 25B, shielding 2565 includes shields 2560 having electrical gaskets 2467c.

Figure 26:
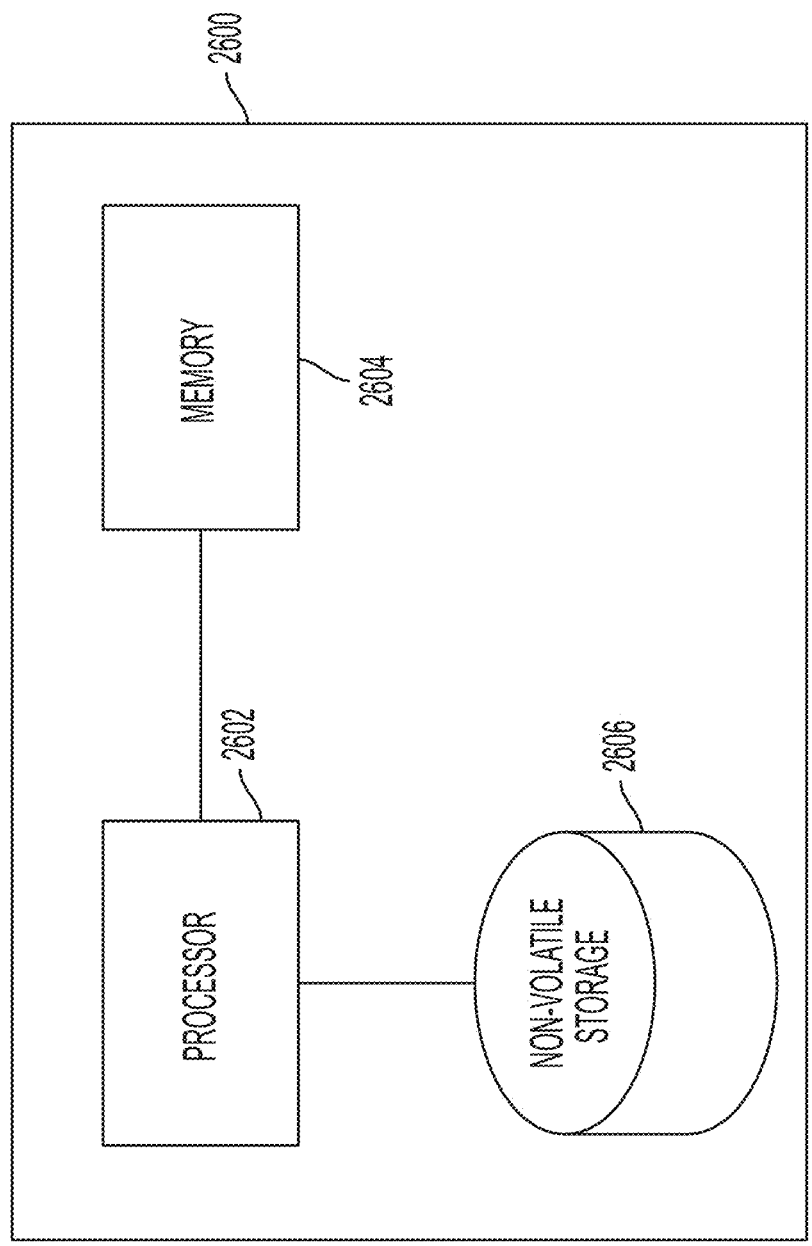
FIG. 26 is a diagram of an illustrative computer system on which embodiments described herein may be implemented.

FIG. 26 is a diagram of an illustrative computer system on which embodiments described herein may be implemented. An illustrative implementation of a computer system 2600 that may be used in connection with any of the embodiments of the disclosure provided herein is shown in FIG. 26. For example, the processes described with reference to FIGS. 2D, 8A-8B, 16, 20, and 21 may be implemented on and/or using computer system 2600. As another example, the computer system 2600 may be used to train and/or use any of the neural network statistical models described herein. The computer system 2600 may include one or more processors 2610 and one or more articles of manufacture that comprise non-transitory computer-readable storage media (e.g., memory 2620 and one or more non-volatile storage media 2630). The processor 2610 may control writing data to and reading data from the memory 2620 and the non-volatile storage device 2630 in any suitable manner, as the aspects of the disclosure provided herein are not limited in this respect. To perform any of the functionality described herein, the processor 2610 may execute one or more processor-executable instructions stored in one or more non-transitory computer-readable storage media (e.g., the memory 2620), which may serve as non-transitory computer-readable storage media storing processor-executable instructions for execution by the processor 2610.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "approximately" and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

What is claimed is:

1. A method for generating magnetic resonance (MR) images of a subject from MR data obtained by a magnetic resonance imaging (MRI) system, the method comprising:
    obtaining input MR data obtained by imaging the subject using the MRI system;
    generating a plurality of transformed input MR data instances by applying a respective first plurality of transformations to the input MR data;
    generating a plurality of MR images from the plurality of transformed input MR data instances and the input MR data using a non-linear MR image reconstruction technique;
    generating an ensembled MR image from the plurality of MR images at least in part by:
        applying a second plurality of transformations to the plurality of MR images to obtain a plurality of transformed MR images, wherein the second plurality of transformations are selected to reverse effects of applying the first plurality of transformations; and
        combining the plurality of transformed MR images to obtain the ensembled MR image; and
    outputting the ensembled MR image.

2. The method of claim 1, wherein using the non-linear MR image reconstruction technique comprises applying a neural network model to the transformed input MR data instances to obtain the plurality of MR images.

3. The method of claim 1, wherein using the non-linear MR image reconstruction technique comprises using a compressed sensing technique.

4. The method of claim 1, wherein applying a first plurality of transformations to the input MR data comprises applying one or more of a constant phase shift transformation, a linear phase shift transformation, a complex conjugation transformation, a rotation transformation, a transpose transformation, and/or a reflection transformation.

5. The method of claim 1, wherein:
    applying the first plurality of transformations to the input MR data comprises applying the first plurality of transformations to the input MR data in a spatial frequency domain;
    applying the second plurality of transformations to the plurality of MR images comprises applying the second plurality of transformations to the plurality of MR images in an image domain; and
    the second plurality of transformations are selected to reverse effects of applying the first plurality of transformations in the spatial frequency domain.

6. The method of claim 1, wherein the input MR data comprises first spatial frequency MR data ($y_i$) for generating an image for a first anatomy slice of a subject and second spatial frequency MR data ($y_{i+1}$) for generating an image for a second anatomy slice of the subject, and wherein:
    generating the plurality of transformed input MR data instances comprises generating a first transformed input MR data instance ($y_i^{+1}$) by adding the second spatial frequency MR data to the first spatial frequency MR data;
    generating the plurality of MR images comprises:
        generating a first MR image ($x_i^{+1}$) from the first transformed data instance ($y_i^{+1}$), and
        generating a second MR image ($x_{i+1}$) from the second MR spatial frequency data ($y_{i+1}$); and
    generating the ensembled MR image comprises:
        subtracting the second MR image from the first MR image ($x_i^{+1} - x_{i+1}$).

7. The method of claim 1, wherein the input MR data comprises first spatial frequency MR data for generating an image for a first anatomy slice of a subject and second spatial frequency MR data for generating one or more images for one or more other anatomy slices of the subject, and wherein:
    generating the plurality of transformed input MR data instances comprises generating a first transformed input MR data instance by combining the first spatial frequency MR data and the second spatial frequency MR data;
    generating the plurality of MR images comprises:
        generating a first MR image from the first transformed input MR data instance, and
        generating one or more second MR images from the second spatial frequency MR data; and
    generating the ensembled MR image comprises:
        subtracting the one or more second MR images from the first MR image.

8. The method of claim 1, wherein the first plurality of transformations includes a complex conjugation transformation and the second plurality of transformations includes a reflection transformation.

9. The method of claim 1, wherein combining the plurality of transformed MR images to obtain the ensembled MR image comprises computing the ensembled MR image as a weighted average of the plurality of transformed MR images.

10. At least one non-transitory computer-readable storage medium storing processor-executable instructions that, when executed by at least one processor, cause the at least one processor to perform a method for generating magnetic resonance (MR) images of a subject from MR data obtained by a magnetic resonance imaging (MRI) system, the method comprising:

obtaining input MR data obtained by imaging the subject using the MRI system;

generating a plurality of transformed input MR data instances by applying a respective first plurality of transformations to the input MR data;

generating a plurality of MR images from the plurality of transformed input MR data instances and the input MR data using a non-linear MR image reconstruction technique;

generating an ensembled MR image from the plurality of MR images at least in part by:

applying a second plurality of transformations to the plurality of MR images to obtain a plurality of transformed MR images, wherein the second plurality of transformations are selected to reverse effects of applying the first plurality of transformations; and combining the plurality of transformed MR images to obtain the ensembled MR image; and outputting the ensembled MR image.

11. The at least one non-transitory computer readable storage medium of claim 10, wherein using the non-linear MR image reconstruction technique comprises applying a neural network model to the transformed input MR data instances to obtain the plurality of MR images.

12. The at least one non-transitory computer readable storage medium of claim 10, wherein using the non-linear MR image reconstruction technique comprises using a compressed sensing technique.

13. The at least one non-transitory computer readable storage medium of claim 10, wherein applying a first plurality of transformations to the input MR data comprises applying one or more of a constant phase shift transformation, a linear phase shift transformation, a complex conjugation transformation, a rotation transformation, a transpose transformation, and/or a reflection transformation.

14. The at least one non-transitory computer readable storage medium of claim 10, wherein:

applying the first plurality of transformations to the input MR data comprises applying the first plurality of transformations to the input MR data in a spatial frequency domain;

applying the second plurality of transformations to the plurality of MR images comprises applying the second plurality of transformations to the plurality of MR images in an image domain; and the second plurality of transformations are selected to reverse effects of applying the first plurality of transformations in the spatial frequency domain.

15. The at least one non-transitory computer readable storage medium of claim 10, wherein the input MR data comprises first spatial frequency MR data ($y_i$) for generating an image for a first anatomy slice of a subject and second spatial frequency MR data ($y_{i+1}$) for generating an image for a second anatomy slice of the subject, and wherein:

generating the plurality of transformed input MR data instances comprises generating a first transformed input MR data instance ($y_i^{+1}$) by adding the second spatial frequency MR data to the first spatial frequency MR data;

generating the plurality of MR images comprises:

generating a first MR image ($x_i^{+1}$) from the first transformed data instance ($y_i^{+1}$), and generating a second MR image ($x_{i+1}$) from the second MR spatial frequency data ($y_{i+1}$); and generating the ensembled MR image comprises:

subtracting the second MR image from the first MR image ($x_i^{+1} - x_{i+1}$).

16. The at least one non-transitory computer readable storage medium of claim 10, wherein the input MR data comprises first spatial frequency MR data for generating an image for a first anatomy slice of a subject and second spatial frequency MR data for generating one or more images for one or more other anatomy slices of the subject, and wherein:

generating the plurality of transformed input MR data instances comprises generating a first transformed input MR data instance by combining the first spatial frequency MR data and the second spatial frequency MR data;

generating the plurality of MR images comprises:

generating a first MR image from the first transformed input MR data instance, and generating one or more second MR images from the second spatial frequency MR data; and generating the ensembled MR image comprises:

subtracting the one or more second MR images from the first MR image.

17. The at least one non-transitory computer readable storage medium of claim 10, wherein the first plurality of transformations includes a complex conjugation transformation and the second plurality of transformations includes a reflection transformation.

18. The at least one non-transitory computer readable storage medium of claim 10, wherein combining the plurality of transformed MR images to obtain the ensembled MR image comprises computing the ensembled MR image as a weighted average of the plurality of transformed MR images.

19. A magnetic resonance imaging (MRI) system configured to capture a magnetic resonance (MR) image, the MRI system comprising:

a magnetics system having a plurality of magnetics components to produce magnetic fields for performing MRI; and at least one processor configured to perform:

obtaining input MR data obtained by imaging a subject using the MRI system;

generating a plurality of transformed input MR data instances by applying a respective first plurality of transformations to the input MR data;

generating a plurality of MR images from the plurality of transformed input MR data instances and the input MR data using a non-linear MR image reconstruction technique;

generating an ensembled MR image from the plurality of MR images at least in part by:

applying a second plurality of transformations to the plurality of MR images to obtain a plurality of transformed MR images, wherein the second plurality of transformations are selected to reverse effects of applying the first plurality of transformations; and combining the plurality of transformed MR images to obtain the ensembled MR image; and outputting the ensembled MR image.

20. The MRI system of claim 19, wherein the plurality of magnetics components comprises at least one permanent $B_0$ magnet configured to generate a $B_0$ magnetic field, the at least one permanent $B_0$ magnet comprising a plurality of permanent magnet rings.

* * * * *